United States Patent
Trudeau et al.

(10) Patent No.: US 9,334,544 B2
(45) Date of Patent: *May 10, 2016

(54) CELLULASE COMPOSITIONS HAVING IMPROVED THERMOSTABILITY AND SYNERGY

(71) Applicant: CALIFORNIA INSTITUTE OF TECHNOLOGY, Pasadena, CA (US)

(72) Inventors: Devin L. Trudeau, Toronto (CA); Frances H. Arnold, La Canada, CA (US); Toni M. Lee, Orange, CA (US); Stephen L. Mayo, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/516,390

(22) Filed: Oct. 16, 2014

(65) Prior Publication Data

US 2015/0050701 A1    Feb. 19, 2015

Related U.S. Application Data

(63) Continuation-in-part of application No. 14/247,221, filed on Apr. 7, 2014.

(60) Provisional application No. 61/944,471, filed on Feb. 25, 2014, provisional application No. 61/809,144, filed on Apr. 5, 2013, provisional application No. 61/822,489, filed on May 13, 2013.

(51) Int. Cl.
| | | |
|---|---|---|
| *C12N 9/26* | (2006.01) | |
| *C12P 19/14* | (2006.01) | |
| *C12P 19/02* | (2006.01) | |
| *C12N 9/42* | (2006.01) | |

(52) U.S. Cl.
CPC ....... *C12Y 302/01004* (2013.01); *C12N 9/2437* (2013.01); *C12P 19/02* (2013.01); *C12P 19/14* (2013.01); *C12Y 302/01091* (2013.01); *Y02P 20/52* (2015.11)

(58) Field of Classification Search
None
See application file for complete search history.

(56) References Cited

PUBLICATIONS

Allen, Benjamin D. et al.; "Dramatic Performance Enhancements for the FASTER Optimization Algorithm"; 2006; Journal of Computational Chemistry; vol. 27; No. 10; pp. 1071-1075.
Altschul, Stephen F. et al.; "Gapped BLAST and PSI-BLAST: a new generation of protein database search programs"; 1997; Nucleic Acids Research; 25; pp. 3389-3402.
Baker, John O. et al.; "Hydrolysis of Cellulose Using Ternary Mixtures of Purified Cellulases"; 1998; Applied Biochemistry and Biotechnology; vol. 70-72; pp. 395-403.
Celik, Eda et al.; "Production of recombinant proteins by yeast cells"; 2012; Biotechnology Advances; 30; pp. 1108-1118.
Chica, Roberto A. et al.; "Generation of longer emission wavelength red fluorescent proteins using computationally designed libraries"; Nov. 23, 2010; PNAS; vol. 107; No. 47; pp. 20257-20262.
Dahiyat, Bassil I. et al.: "Probing the role of packing specificity in protein design"; Sep. 1997; PNAS; 94; pp. 10172-10177.
Dahiyat, Bassil I. et al.; "Automated design of the surface positions of protein helices"; 1997; Protein Science; 6; pp. 1333-1337.
Desmet, Johan et al.; "Fast and Accurate Side-Chain Topology and Energy Refinement (FASTER) as a New Method for Protein Structure Optimization"; 2002; Proteins: Structure, Function, and Genetics; 48; pp. 31-43.
Dombkowski, Alan A.; "Disulfide by Design™: a computational method for the rational design of disulfide bonds in proteins"; 2003; Bioinformatics; vol. 19; No. 14; pp. 1852-1853.
Edgar, Robert C.; "MUSCLE: multiple sequence alignment with high accuracy and high throughput"; Mar. 19, 2004; Nucleic acids research; vol. 32; No. 5; pp. 1792-1797.
Gasteiger, Elisabeth et al.; "Protein Identification and Analysis Tools on the ExPASy Server"; 2005; The Proteomics Protocols Handbook; pp. 571-607.
Gibson, Daniel G.; "Enzymatic Assembly of Overlapping DNA Fragments"; 2011; Methods in Enzymology; Chapter 15; vol. 498; pp. 349-361.
Gibson, Daniel G. et al.; "Enzymatic assembly of DNA molecules up to several hundred kilobases"; May 2009; Nature Methods; vol. 6; No. 5; pp. 343-345.
Green III, Frederick et al.; "Adaptation of the Nelson-Somogyi Reducing-Sugar Assay to a Microassay Using Microtiter Plates"; 1989; Analytical Biochemistry; 182; pp. 197-199.
Heinzelman, Pete et al.; "A family of thermostable fungal cellulases created by structure-guided recombination"; Apr. 7, 2009; PNAS; vol. 106; No. 14; pp. 5610-5615.
Hsu, Teng-Chieh et al.; "Effect of dilute acid pretreatment of rice straw on structural properties and enzymatic hydrolysis"; 2010; Bioresource Technology; 101; pp. 4907-4913.
Komor, Russell S. et al.; "Highly thermostable fungal cellobiohydrolase I (Cel7A) engineered using predictive methods"; 2012; Protein Engineering, Design & Selection; vol. 25; No. 12; pp. 827-833.
Lee, Toni M. et al.; "A structural study of Hypocrea jecorina Cel5A"; Sep. 2011; Protein Science; vol. 20; pp. 1935-1940.
Marshall, Shannon A. et al.; "Electrostatics Significantly Affect the Stability of Designed Homeodomain Variants"; 2002; J. Mol. Biol.; 316; pp. 189-199.
Matlab; "Statistics and Machine Learning Toolbox Release Notes"; 2011, The MathWorks, Inc.; 138pp.

(Continued)

*Primary Examiner* — Nashaat Nashed
(74) *Attorney, Agent, or Firm* — Lewis Roca Rothgerber Christie LLP

(57) ABSTRACT

A variant Cel5a endoglucanase has increased thermostability, increased enzymatic activity and/or increased expression in a host, relative to wild type Cel5a. The improved variant Cel5a endoglucanase may be used to hydrolyze more cellulose at a higher temperature for a more efficient and cost-effective production of biofuels as compared to wild type Cel5a. A variant Cel5a endoglucanase is combined with variant Cel6a and variant Cel7a cellobiohydrolases resulting in more effective hydrolysis of cellulose.

12 Claims, 43 Drawing Sheets
(35 of 43 Drawing Sheet(s) Filed in Color)

(56) References Cited

PUBLICATIONS

Mayo, Stephen L. et al.; "DREIDING: A Generic Force Field for Molecular Simulations"; 1990; J. Phys. Chem.; 94; pp. 8897-8909.

Metropolis, Nicholas et al.; "Equation of State Calculations by Fast Computing Machines"; Jun. 1953; The Journal of Chemical Physics; vol. 21; No. 6; pp. 1087-1092.

Meyer, Anne S. et al.; "The minimal enzyme cocktail concept for biomass processing"; 2009; Journal of Cereal Science; 50; pp. 337-344.

Murray, Patrick et al.; "Expression in Trichoderma reesei and characterisation of a thermostable family 3 β-glucosidase from the moderately thermophilic fungus *Talaromyces emersonii*"; 2004; Protein Expression & Purification; 38; pp. 248-257.

Nelson, Norton; "A Photometric Adaptation of the Somogyi Method for the Determination of Glucose"; Feb. 3, 1944; J. Biol. Chem.; 153; pp. 375-379.

Park, James T. et al.; "A submicrodetermination of glucose"; Jun. 23, 1949; J. Biol. Chem.; 181; pp. 149-151.

Qin, Yuqi et al.; "Purification and characterization of recombinant endoglucanase of Trichoderma reesei expressed in *Saccharomyces cerevisiae* with higher glycosylation and stability"; 2008; Protein Expression & Purification; 58; pp. 162-167.

Rohl, Carol A. et al.; "[4] Protein Structure Prediction Using Rosetta"; 2004; Methods in Enzymology; vol. 383; pp. 66-93.

Romero, Philip A. et al.; "SCHEMA-Designed Variants of Human Arginase I and II Reveal Sequence Elements Important to Stability and Catalysis"; 2012; ACS Synthetic Biology; 1; pp. 221-228.

Schiestl, Robert H. et al. "Introducing DNA into yeast by transformation," 1993; Methods: A Companion to Methods in Enzymology; 5; pp. 79-85.

Schymkowitz, Joost et al.; "The FoldX web server: an online force field"; 2005, Nucleic Acids Research; vol. 33; pp. W382-W388.

Smith, Matthew A. et al.; "Hypocrea jecorina Cellobiohydrolase I Stabilizing Mutations Identified Using Noncontiguous Recombination"; 2013; ACS Synthetic Biology; 2; pp. 690-696.

Somogyi, Michael; "Notes on Sugar Determination"; 195; J. Biol. Chem.; 195; pp. 19-23.

Su, Xiaoyun et al.; "Heterologous Gene Expression in Filamentous Fungi"; 2012; Advances in Applied Microbiology; vol. 81; Chapter 1; pp. 1-61.

Sullivan, Brandon J. et al.; "Stabilizing Proteins from Sequence Statistics: The Interplay of Conservation and Correlation in Triosephosphate Isomerase Stability"; 2012; Journal of Molecular Biology; 420; pp. 384-399.

Sun, Ye et al.; "Hydrolysis of lignocellulosic materials for ethanol production: a review"; 2002; Bioresource Technology; 83; pp. 1-11.

Van Dyk, J.S. et al.; "A review of lignocellulose bioconversion using enzymatic hydrolysis and synergistic cooperation between enzymes—Factors affecting enzymes, conversion and synergy"; 2012; Biotechnology Advances; 30; pp. 1458-1480.

Villalobos, Alan et al.; "Gene Designer: a synthetic biology tool for constructing artificial DNA segments"; 2006; BMC Bioinformatics; 7; 285; 8pp.

Voigt, Christopher A. et al.; "Trading Accuracy for Speed: A Quantitative Comparison of Search Algorithms in Protein Sequence Design"; 2000; J. Mol. Biol.; 299; pp. 789-803.

Wu, Indira et al.; "Engineered Thermostable Fungal Cel6A and Cel7A Cellobiohydrolases Hydrolyze Cellulose Efficiently at Elevated Temperatures"; 2013; Biotechnology and Bioengineering; vol. 110; No. 7; pp. 1874-1883.

Ye, Xiaoduan et al.; "Hypergraph Model of Multi-Residue Interactions in Proteins: Sequentially-Constrained Partitioning Algorithms for Optimization of Site-Directed Protein Recombination"; 2007; Journal of Computational Biology; vol. 14; No. 6; pp. 777-790.

Zhang, Yi-Heng Percival et al.; "Toward an Aggregated Understanding of Enzymatic Hydrolysis of Cellulose: Noncomplexed Cellulase Systems"; Dec. 30, 2004; Biotechnology and Bioengineering; vol. 88; No. 7; pp. 797-824.

FIG. 3C
FIG. 3D
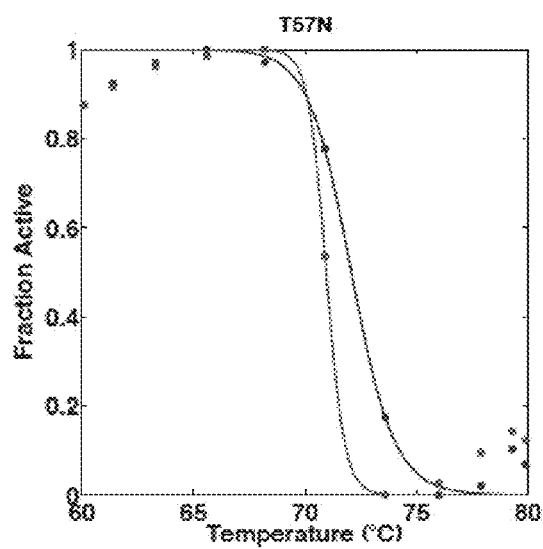
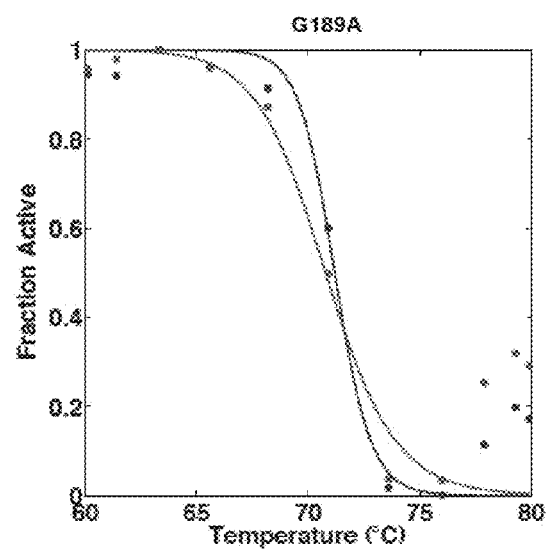

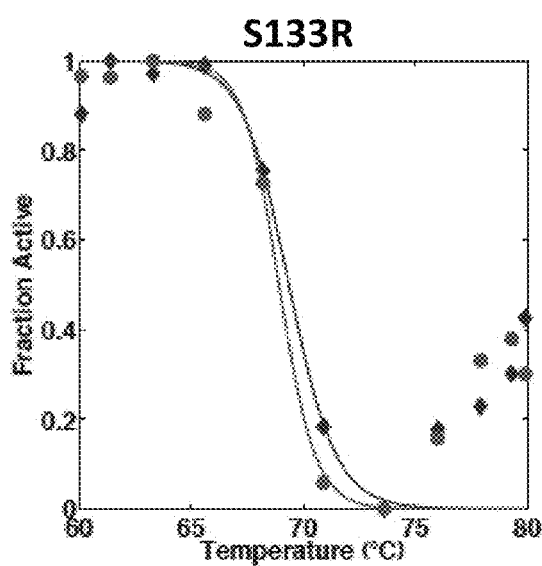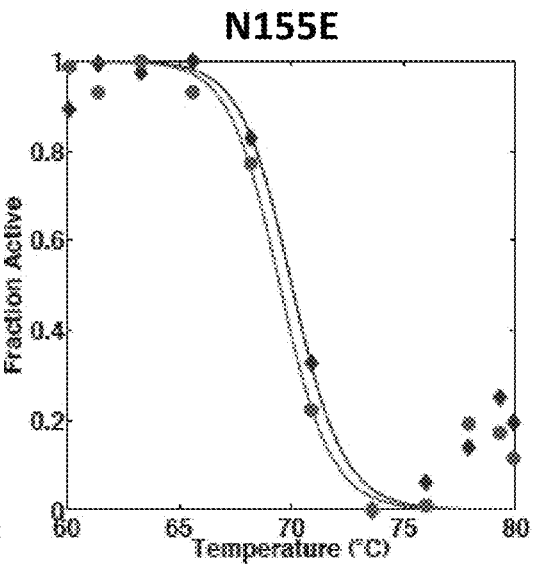
FIG. 8C  S133R
FIG. 8D  N155E

CELLULASE COMPOSITIONS HAVING IMPROVED THERMOSTABILITY AND SYNERGY

CROSS-REFERENCE TO RELATED APPLICATION(S)

The present application claims priority to and the benefit of U.S. Provisional Application Ser. No. 61/944,471 filed on Feb. 25, 2014, and is a continuation-in-part of U.S. application Ser. No. 14/247,221 filed on Apr. 7, 2014, which claims priority to and the benefit of U.S. Provisional Application Ser. No. 61/809,144 filed on Apr. 5, 2013 and U.S. Provisional Application Ser. No. 61/822,489 filed on May 13, 2013, the entire contents of all of which are incorporated herein by reference.

STATEMENT REGARDING FEDERALLY SPONSORED RESEARCH OR DEVELOPMENT

This invention was made with government support under Grant number W911NF-09-D-0001 awarded by the US Army and Grant numbers N00244-09-1-0011 and N00244-09-1-0082 awarded by the US Navy. The government has certain rights in the invention.

INCORPORATION BY REFERENCE

The present application contains a Sequence Listing which has been submitted in ASCII format via EFS-Web and is hereby incorporated by reference in its entirety. The Sequence Listing submitted herewith is a text file entitled "AMENDEDSEQLISTING74936.txt" that was amended on Feb. 25, 2016 and is 14,125 bytes in size.

BACKGROUND

The primary component of plant cell walls, cellulose, is not only the most abundant biopolymer, but it is also a completely renewable resource. In order to expose cellulose, the lignocellulosic material made up of cellulose, hemicellulose and lignin, often requires a harsh chemical or temperature-based pretreatment to remove the hemicellulose and lignin. The cellulose is subsequently digested with mixtures of expensive cellulose-digesting enzymes, called cellulases. Digestion (by hydrolysis) of the cellulose by cellulases produces glucose which can be fermented into liquid fuel.

At this time, for the digestion of cellulose to be economically feasible, the cellulase production costs must decrease. For complete cellulose digestion, a mixture of wild type fungal cellulases is known to require at least three different activities: endoglucanase, cellobiohydrolase I, and cellobiohydrolase II, where each type of activity may be carried out by more than one enzyme. The filamentous fungus, *Hypocrea jecorina* (*Trichoderma reesei*) digests cellulose using the least number of cellulase enzymes, and the majority of the digestion is attributed to four enzymes: Cel7a, Cel6a, Cel5a, and Cel7B. As such, an enzymatic mixture made using these *H. jecorina* cellulases requires fewer components for complete digestion.

SUMMARY

In some embodiments of the present invention, a composition includes a variant Cel5a endoglucanase as disclosed herein having a $T_{50}$ above the $T_{50}$ of wild type Cel5a endoglucanase and increased enzymatic activity relative to wild type Cel5a endoglucanase, the composition also includes a variant Cel6a cellobiohydrolase and/or a variant Cel7a cellobiohydrolase.

In some embodiments of the present invention, the variant Cel5a endoglucanase having a $T_{50}$ above a $T_{50}$ of wild type Cel5a endoglucanase and increased enzymatic activity includes a single point mutation in the Cel5a amino acid sequence selected from the group consisting of E53D, T57N, S79P, T80E, V101I, S133R, N153D, N155E, T156E, G189S, F191V, T233V, G239E, V265T, D271Y, G293A, S309W/L, S318P/Q/E, and combinations thereof, with mutant residue numbering based on SEQ ID NO: 6.

In some embodiments of the present invention, the variant Cel5a endoglucanase having a $T_{50}$ above a $T_{50}$ of wild type Cel5a endoglucanase and increased enzymatic activity includes a combination of point mutations in the Cel5a amino acid sequence. In some embodiments, for example, the combination of point mutations may include any of the following combinations, with mutant residue numbering based on SEQ ID NO: 6:

G189A, F191V, G239D, S242A, V265T, D271Y, S318P/E, and S322A;

E53D, T57N, S79P, T80E, V101I, S133R, N155E, G189S, G239E, D271Y, G293A, S309L, and S318P;

E53D, T57N, S79P, T80E, V101I, S133R, N155E, G189S, G239E, D271Y, G293A, S309W, and S318P;

E53D, T57N, S79P, T80E, V101I, S133R, N155E, G189S, G239E, D271Y, G293A, S309L, and S318E;

E53D, T57N, S79P, T80E, V101I, S133R, N155E, G189S, G239E, D271Y, G293A, S309W, and 5318E; or E53D, T57N, S79P, T80E, V101I, S133R, N155E, G189S, F191V, T233V, G239E, V265T, D271Y, G293A, S309W, and S318P.

In some embodiments of the present invention, a method of hydrolyzing cellulose includes hydrolyzing the cellulose with the composition including a variant Cel5a endoglucanase composition having a $T_{50}$ above a $T_{50}$ of wild type Cel5a endoglucanase and increased enzymatic activity relative to wild type, the composition also including a variant Cel6a cellobiohydrolase and/or a variant Cel7a cellobiohydrolase.

In some embodiments of the present invention, a composition includes a variant Cel5a endoglucanase having a $T_{50}$ above the $T_{50}$ of wild type Cel5a endoglucanase, the composition including a point mutation selected from D13E, T18P, E53D, T57N, N76P, S79P/Q, T80E, I82M, V101I, S133R, S139P, N153D, N155E/Q, T156E, G189S/A/E, F191V, K219Q/A, T233V, G239E/N/D, V265T, D271Y/F, Y278F, G293A, S309W/F/L, S318P/Q/E, or any combination thereof, with mutant residue numbering based on SEQ ID NO: 6.

In some embodiments of the present invention, a composition includes a variant Cel5a endoglucanase having increased protein expression in a host organism compared to wild type Cel5a, the composition including a point mutation selected from D13E, T18P, G64A, N76P, S79P/Q/E, T80E/Q, I82L/M, V101I/L, A122E, S133R, S139P, N155E/Q, T156E, G189S/A/E/K, K219Q/A, G239E/N/D, V265T, D271Y/F, Y278F, G293A, S309W/F/L, or S318P/Q/E, with mutant residue numbering based on SEQ ID NO: 6.

In some embodiments of the present invention, a composition includes a variant Cel5a endoglucanase having a $T_{50}$ above the $T_{50}$ of wild type Cel5a endoglucanase, increased enzymatic activity relative to wild type Cel5a endoglucanase, and increased protein expression in a host organism relative to wild type Cel5a, the variant Cel5a endoglucanase having a combination of mutations which may include any of the following combinations, with mutant residue numbering based on SEQ ID NO: 6:

G189A, F191V, G239D, S242A, V265T, D271Y, S318P/E, and S322A;

E53D, T57N, S79P, T80E, V101I, S133R, N155E, G189S, G239E, D271Y, G293A, S309L, and S318P;

E53D, T57N, S79P, T80E, V101I, S133R, N155E, G189S, G239E, D271Y, G293A, S309W, and S318P;

E53D, T57N, S79P, T80E, V101I, S133R, N155E, G189S, G239E, D271Y, G293A, S309L, and S318E;

E53D, T57N, S79P, T80E, V101I, S133R, N155E, G189S, G239E, D271Y, G293A, S309W, and 5318E; or E53D, T57N, S79P, T80E, V101I, S133R, N155E, G189S, F191V, T233V, G239E, V265T, D271Y, G293A, S309W, and S318P.

BRIEF DESCRIPTION OF THE DRAWINGS

The patent or application file contains at least one drawing executed in color. Copies of this patent or patent application publication with color drawings will be provided by the Office upon request and payment of the necessary fee.

These and other features and advantages of the present invention will be better understood by reference to the following detailed description when considered in conjunction with the accompanying drawings.

FIG. 3C is a $T_{50}$ plot for the Cel5a T57N mutant of FIG. 2, where the fraction active reflects the amount of the total protein that is active after a 10 minute heat treatment from 60-80° C., where WT (green) and the point mutant (blue) are shown, according to embodiments of the present invention.

FIG. 3D is a $T_{50}$ plot for the Cel5a G189A mutant of FIG. 2, where the fraction active reflects the amount of the total protein that is active after a 10 minute heat treatment from 60-80° C., where WT (green) and the point mutant (blue) are shown, according to embodiments of the present invention.

FIG. 8C is a $T_{50}$ plot for the Cel5a S133R mutant of FIG. 7, where the fraction active reflects the amount of the total protein that is active after a 10 minute heat treatment from 60-80° C., where WT (green) and the point mutant (yellow) are shown, according to embodiments of the present invention.

FIG. 8D is a $T_{50}$ plot for the Cel5a N155E mutant of FIG. 7, where the fraction active reflects the amount of the total protein that is active after a 10 minute heat treatment from 60-80° C., where WT (green) and the point mutant (yellow) are shown, according to embodiments of the present invention.

DETAILED DESCRIPTION

Figure 1:
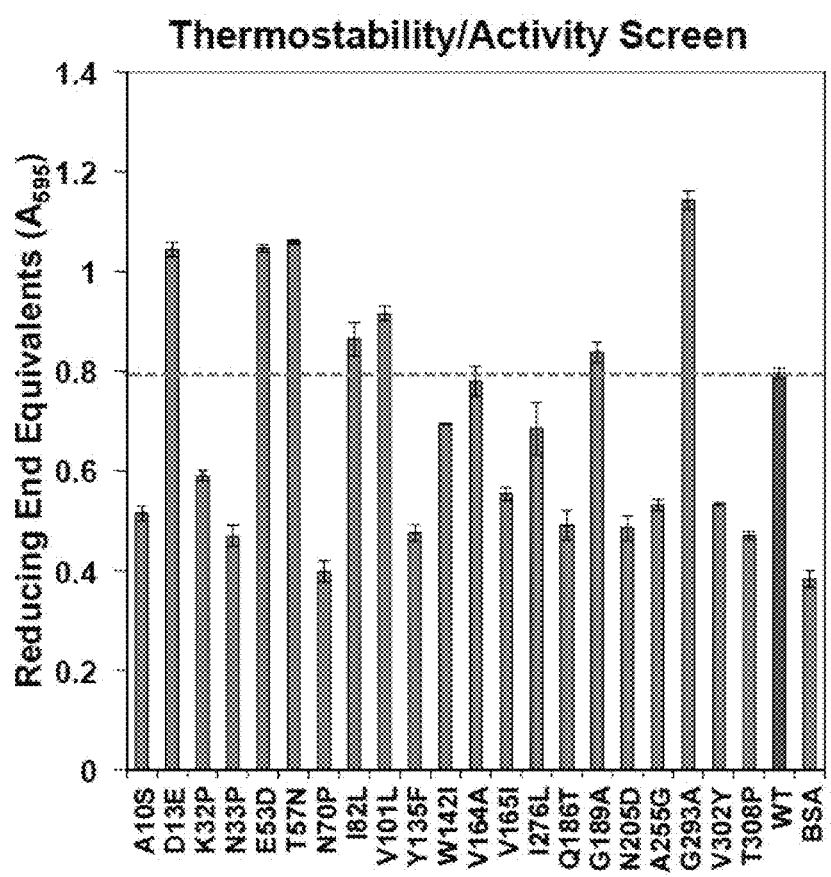
FIG. 1 is a graph measuring thermostability and activity in wild type (WT) and the indicated Cel5a point mutant proteins (with mutant residue numbering based on SEQ ID NO: 6) following a reducing end (Park-Johnson) assay as described herein, with bovine serum albumin (BSA) used as a control, according to embodiments of the present invention.
Figure 2:
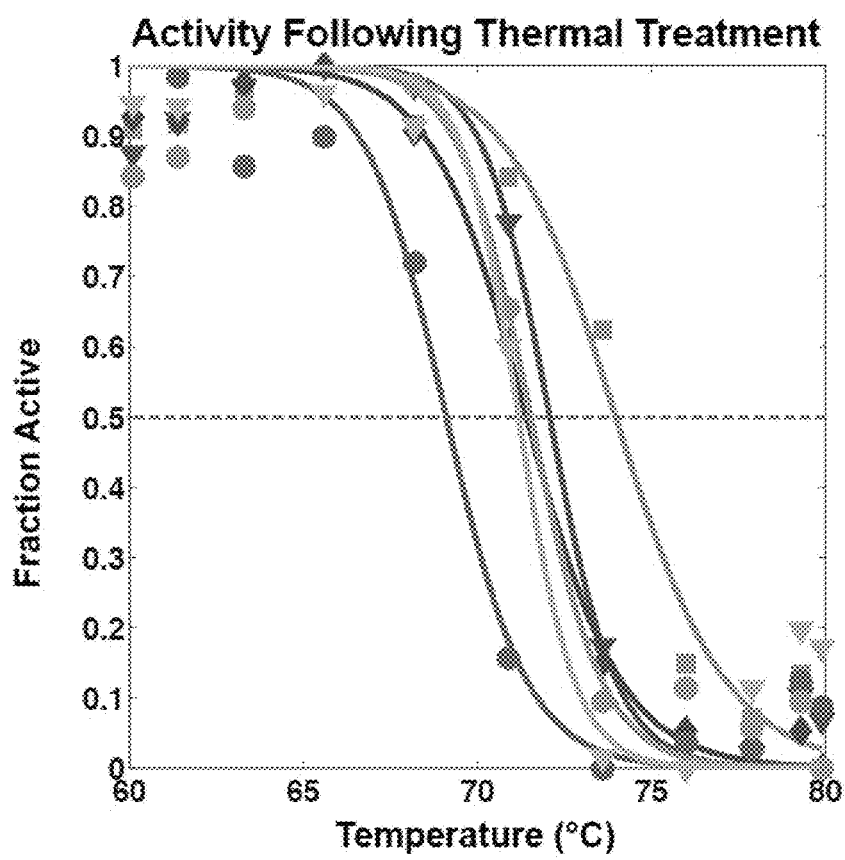
FIG. 2 is a graph corresponding to thermostability and activity of FIG. 1 showing the amount of activity versus an increase in temperature of the wild type (green) and the indicated Cel5a mutants (with mutant residue numbering based on SEQ ID NO: 6): D13E (pink circles), E53D (dark blue diamonds), T57N (light blue triangles), G189A (yellow triangles), and G293A (orange squares), where the dashed line indicates the point at which 50% of the maximal protein activity remains ($T_{50}$), according to embodiments of the present invention.
Figure 3A:
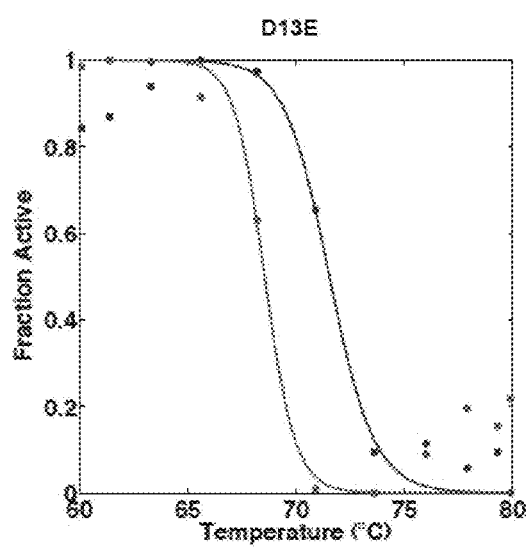
FIG. 3A is a $T_{50}$ plot for the Cel5a D13E mutant of FIG. 2, where the fraction active reflects the amount of the total protein that is active after a 10 minute heat treatment from 60-80° C., where WT (green) and the point mutant (blue) are shown, according to embodiments of the present invention.
Figure 3B:
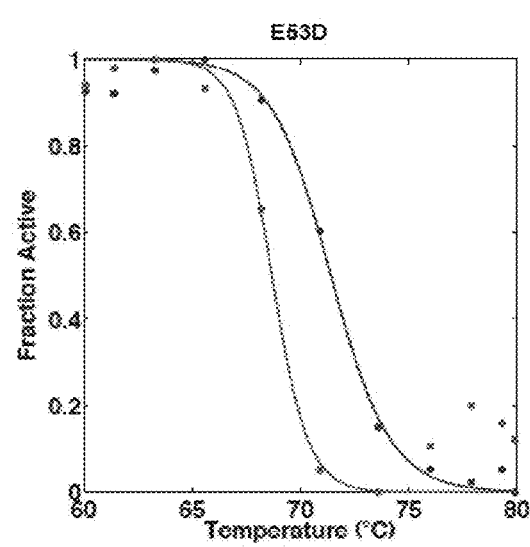
FIG. 3B is a $T_{50}$ plot for the Cel5a E53D mutant of FIG. 2, where the fraction active reflects the amount of the total protein that is active after a 10 minute heat treatment from 60-80° C., where WT (green) and the point mutant (blue) are shown, according to embodiments of the present invention.
Figure 3E:
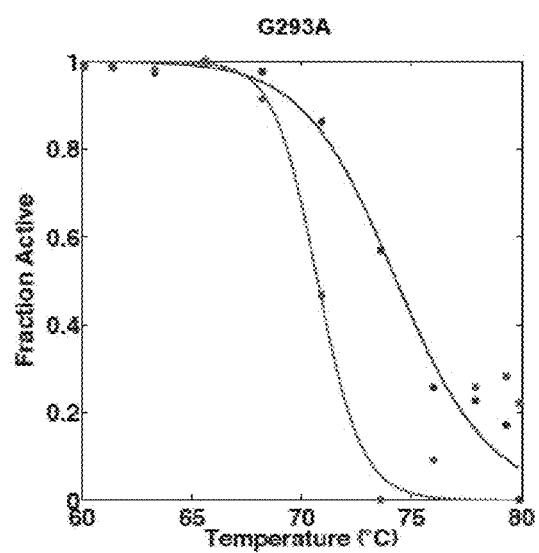
FIG. 3E is a $T_{50}$ plot for the Cel5a G293A mutant of FIG. 2, where the fraction active reflects the amount of the total protein that is active after a 10 minute heat treatment from 60-80° C., where WT (green) and the point mutant (blue) are shown, according to embodiments of the present invention.
Figure 3F:
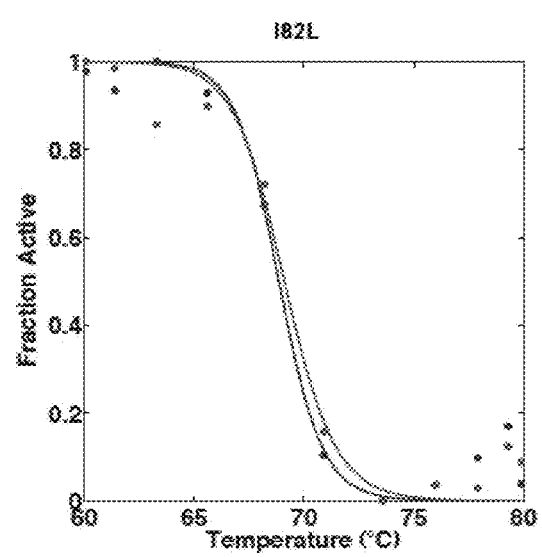
FIG. 3F is a $T_{50}$ plot for the Cel5a I82L mutant of FIG. 2, where the fraction active reflects the amount of the total protein that is active after a 10 minute heat treatment from 60-80° C., where WT (green) and the point mutant (blue) are shown, according to embodiments of the present invention.
Figure 3G:
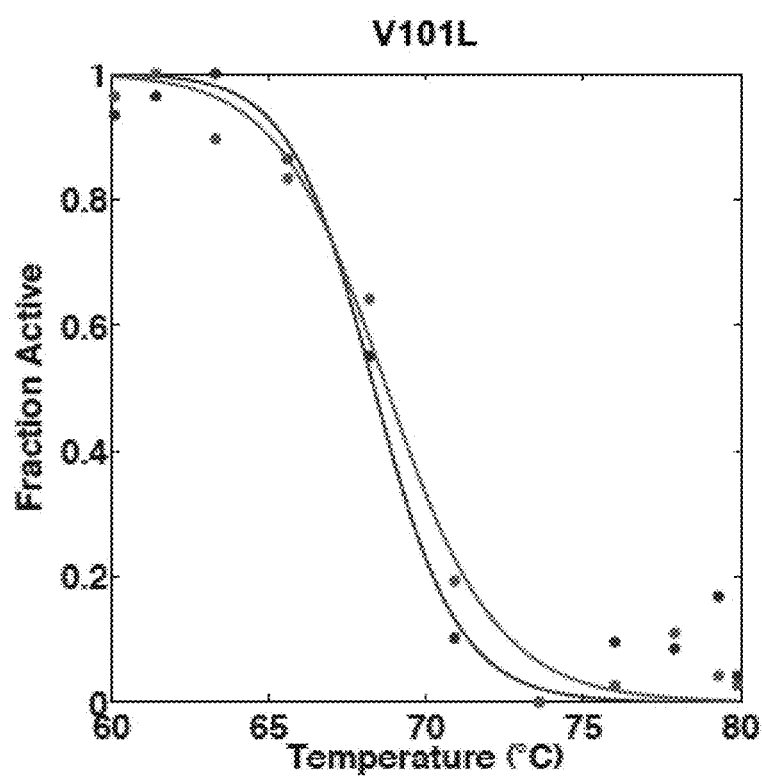
FIG. 3G is a $T_{50}$ plot for the Cel5a V101L mutant of FIG. 2, where the fraction active reflects the amount of the total protein that is active after a 10 minute heat treatment from 60-80° C., where WT (green) and the point mutant (blue) are shown, according to embodiments of the present invention.

Some embodiments of the present invention include variants of the endoglucanase Cel5a having thermostability at higher temperatures compared to wild type (WT) Cel5a. As used herein, "thermostability" refers to the stability and resistance of the enzyme protein (e.g., Cel5a protein) in response to changes in temperature. In this disclosure, an increase in thermostability refers to an increase in the range of higher temperatures at which the enzyme protein is stable and does not degrade compared to wild type. As disclosed herein, a $T_{50}$ assay is used to determine the thermostability of a protein. Specifically, a $T_{50}$ assay determines the temperature at which half of the maximal protein activity remains. In this way, for example, the Cel5a variants disclosed herein having increased thermostability do not degrade at some of the higher temperatures at which WT Cel5a degrades. For example, an increase in thermostability is any increase in the $T_{50}$ of a Cel5a variant protein above that of WT Cel5a protein, resulting in a positive $\Delta T_{50}$ compared to WT. For example, any increase in a Cel5a variant $T_{50}$ may be beneficial. In some embodiments, a Cel5a variant $T_{50}$ may be up to about 17° C. higher than wild type Cel5a. As such, by increasing the thermostability of the Cel5a enzyme, the reaction temperature for cellulose digestion may be increased. Increasing the reaction temperature for cellulose digestion is useful because isolating cellulose from the lignocellulosic material requires heating at about 200° C. As such, being able to perform the subsequent cellulose hydrolysis step at temperatures higher than the current industry standard of about 50° C. may reduce the amount of energy necessary to cool the pretreated cellulose substrate. (Sun et al. 2002, *Bioresource Technol.*, 83:1-11, the entire contents of which are herein incorporated by reference.) This reduction in energy may result in a reduction in the overall production cost.

Some embodiments of the present invention include Cel5a variants having both increased thermostability and increased enzymatic activity compared to wild type (WT) Cel5a. As such, these Cel5a variants are able to digest cellulose at a higher temperature than wild type and digest more cellulose than wild type. For example, as disclosed herein, increased amounts of cellulase activity compared to WT Cel5a range from about 0.1 to about 100 μM more cellobiose equivalents at 60° C., and from about 0.1 to about 1 mM (1,000 μM) more cellobiose equivalents at 70° C.

Some embodiments of the present invention include Cel5a variants having increased expression compared to wild type. As such, more Cel5a protein may be isolated without an increase in the culture processing of the expression host organism. Some embodiments of the present invention include Cel5a variants having increased thermostability, increased activity, and increased expression compared to wild type Cel5a.

Abbreviations for amino acids are used throughout this disclosure and follow the standard nomenclature known in the art. Alanine is Ala or A; Arginine is Arg or R; Asparagine is Asn or N; Aspartic Acid is Asp or D; Cysteine is Cys or C; Glutamic acid is Glu or E; Glutamine is Gln or Q; Glycine is Gly or G; Histidine is His or H; Isoleucine is Ile or I; Leucine is Leu or L; Lysine is Lys or K; Methionine is Met or M;

Phenylalanine is Phe or F; Proline is Pro or P; Serine is Ser or S; Threonine is Thr or T; Tryptophan is Trp or W; Tyrosine is Tyr or Y; and Valine is Val or V.

For point mutations, amino acid substitutions are shown, for example, as E53D, where the wild type glutamic acid (E) at position 53 is changed to aspartic acid (D). Also, S318P/Q/E denotes that the wild type serine (S) at position 318 may be changed to proline (P), glutamine (Q), or glutamic acid (E).

As used herein the terms "variant" and "mutant" are used interchangeably to refer to a protein having a change in the wild type protein sequence.

Expression of HjCel5a

The Cel5a variants of the present invention have at least one point mutation in the amino acid sequence of wild type Hypocrea jecorina (Trichoderma reesei) Cel5a. Wild type HjCel5a is encoded by the DNA sequence of SEQ ID NO: 1. As used herein, Cel5a and HjCel5a are used interchangeably to refer to the endoglucanase (SEQ ID NO: 7) encoded by SEQ ID NO: 1 or an indicated variant thereof.

The HjCel5a variant and wild type proteins as disclosed herein are transformed and expressed in the yeast host Saccharomyces cerevisiae. However, the Cel5a variants of the present invention and the Cel6a and Cel7a variants may be expressed in any suitable host organism. Non-limiting examples of host organisms include Trichoderma, Saccharomyces, Pichia and Aspergillus. Any industrial expression system with known culturing methodologies may be used. Examples of known host organisms are described in Murray P, et al. 2004. Protein Expr Purif, 38:248-257; Qin et al. 2008, Protein Expr Purif 58:162-167; Celik et al., 2012, Biotechnol. Adv., 30:1108-1118; and Su et al., 2012, Adv. Appl. Microbiol., 81:1-61, the entire contents of all of which are herein incorporated by reference.

All expression plasmids encoding enzyme proteins disclosed herein, including Cel5a, Cel6a, and/or Cel7a may be constructed by any appropriate methods known in the art. Methods for constructing the various Cel5a, Cel6a, and Cel7a plasmids are disclosed in the Examples, but the present invention is not limited by the particular plasmid sequences disclosed herein, excluding the indicated Cel5a, Cel6a and Cel7a variant sequences.

Cel5a Thermostability Mutants

Thermostability of Cel5a mutants was assayed using a $T_{50}$ or $T_{A50}$ assay as described in Examples 1 and 4, respectively. The $T_{50}$ and $T_{A50}$ assays determine the temperature at which half of the maximal protein activity remains, and is used to assay thermostability of a protein. As used herein, the temperatures determined by a $T_{50}$ or $T_{A50}$ assay approximate each other, and are therefore used interchangeably. In some embodiments of the present invention, a Cel5a mutant endoglucanase having a $T_{50}$ above the $T_{50}$ of wild type Cel5a endoglucanase includes a point mutation in the wild type amino acid sequence of Cel5a. The Cel5a amino acid point mutations conferring an increased $T_{50}$ over wild type Cel5a include: D13E, T18P, E53D, T57N, N76P, S79P/Q, T80E, I82M, V101I, S133R, S139P, N153D, N155E/Q, T156E, G189S/A/E, F191V, K219Q/A, T233V, G239E/N/D, V265T, D271Y/F, Y278F, G293A, S309W/F/L, S318P/Q/E, or any combination thereof, with mutant residue numbering based on SEQ ID NO: 6.

Cel5a combination mutants of the listed point mutations above also confer increased thermostability compared to wild type Cel5a. In some embodiments a set of point mutations in Cel5a, with mutant residue numbering based on SEQ ID NO: 6, having increased thermostability over wild type Cel5a include one of the following sets:

N76P and S139P;
T57N, N76P, S139P, and N155E;
T57N, N76P, S139P, N155E, and G189S;
T57N, N76P, S139P, N155E, and K219Q;
T57N, N76P, S139P, N155E, and G239N;
T57N, N76P, S139P, N155E, and D271F;
T57N, N76P, S139P, N155E, D271F, and Y278F;
T57N, N76P, S139P, N155E, G189S, and K219Q;
T57N, N76P, S139P, N155E, G189S, and G239N;
T57N, N76P, S139P, N155E, G189S, K219Q, and G239N;
T57N, N76P, S139P, N155E, G189S, D271F, and Y278F;
T57N, N76P, S139P, N155E, G189S, D271F, Y278F, and G293A;
T57N, N76P, T80E; S139P, N155E, G189S, D271F, Y278F, and G293A;
T57N, N76P, S139P, N155E, G189S, K219Q, G239N, D271F, Y278F, and G293A;
T57N, N76P, T80E, S139P, N155E, G189S, K219Q, G239N, D271F, Y278F, and G293A;
T57N, N76P, T80E, S139P, N155E, G189S, K219Q, G239N, D271F, Y278F, G293A, and S318P;
T57N, N76P, T80E, S139P, N155E, G189S, K219Q, G239N, D271F, Y278F, G293A, S309F, and S318P;
T80E, S133R, N155E, G239E, Y278F, and S318Q;
E53D, T57N, S79P, T80E, V101I, S133R, N155E, G189S, G239E, D271Y, G293A, S309L, and S318P;
E53D, T57N, S79P, T80E, V101I, S133R, N155E, G189S, G239E, D271Y, G293A, S309W, and S318P;
E53D, T57N, S79P, T80E, V101I, S133R, N155E, G189S, G239E, D271Y, G293A, S309L, and S318E;
E53D, T57N, S79P, T80E, V101I, S133R, N155E, G189S, G239E, D271Y, G293A, S309W, and S318E;
G189A, F191V, G239D, S242A, V265T, D271Y, S318P/E, and S322A; or
E53D, T57N, S79P, T80E, V101I, S133R, N155E, G189S, F191V, T233V, G239E, V265T, D271Y, G293A, S309W, and S318P.

These point mutations and sets of point mutations are characterized for thermostability as disclosed, for example, in Examples 1-4 and FIGS. 1, 5, 7, 9B, 11A, 11B, 14A, 14B, 17, and 19A.

Cel5a Mutants Having Increased Thermostability and Activity

The Cel5a mutants having increased thermostability were assayed for enzymatic activity using, for example, a cellulase activity assay measuring cellobiose digestion, as described in Examples 1 and 6. The amino acid point mutations in Cel5a that confer both an increased $T_{50}$ and increased enzymatic activity compared to wild type Cel5a include: E53D, T57N, S79P, T80E, V101I, S133R, N153D, N155E, T156E, G189S, F191V, T233V, G239E, V265T, D271Y, G293A, S309W/L, or S318P/Q/E, with mutant residue numbering based on SEQ ID NO: 6. These point mutations are characterized for thermostability and activity, for example, in Examples 1-4, Tables I-IV, and FIGS. 4, 10B, 10C, 16A, 16B, and 17.

In some embodiments of the present invention, combinations of point mutations confer increased thermostability and activity. In some embodiments, a Cel5a mutant endoglucanase having both increased thermostability and activity has a combination of point mutations in the Cel5a amino acid sequence including one of the following sets of mutations, with mutant residue numbering based on SEQ ID NO: 6:

G189A, F191V, G239D, S242A, V265T, D271Y, S318P/E, and S322A;
E53D, T57N, S79P, T80E, V101I, S133R, N155E, G189S, G239E, D271Y, G293A, S309L, and S318P;

E53D, T57N, S79P, T80E, V101I, S133R, N155E, G189S, G239E, D271Y, G293A, S309W, and S318P;

E53D, T57N, S79P, T80E, V101I, S133R, N155E, G189S, G239E, D271Y, G293A, S309L, and S318E;

E53D, T57N, S79P, T80E, V101I, S133R, N155E, G189S, G239E, D271Y, G293A, S309W, and S318E; or E53D, T57N, S79P, T80E, V101I, S133R, N155E, G189S, F191V, T233V, G239E, V265T, D271Y, G293A, S309W, and S318P.

The above combination mutants are characterized for thermostability and activity, for example, in Examples 4-6, Tables V and VI, and FIGS. 18A, 18B, 20C, 20D, 21C, 21D, 22A, and 22B.

In some embodiments of the present invention, a Cel5a mutant endoglucanase has increased thermostability (as measured by a $T_{50}$ assay) up to 17° C. above the $T_{50}$ of wild type Cel5a and retains the same activity at least at 60° C.

In some embodiments, a Cel5a mutant endoglucanase having increased thermostability and activity relative to wild type Cel5a is combined with other cellulases having improved thermostability and activity. This combination of cellulases provides an improved cellulase cocktail composition for a more efficient and cost-effective hydrolysis of cellulose. Examples of other cellulases include the cellobiohydrolases, Cel6a and Cel7a, as disclosed herein, for example, in Example 7 and FIGS. 23A-23D and 24A-24D.

Cel5a Mutants Having Increased Expression

Some Cel5a mutants confer an increase in expression as compared to wild type Cel5a. As used herein, "protein expression" refers to the amount of protein produced in a host organism. Cel5a is expressed into the medium of the host cell—for example, S. cerevisiae. The single amino acid point mutations in Cel5a that confer increased protein expression of the Cel5a mutant protein in S. cerevisiae compared to the level of wild type Cel5a protein expression in S. cerevisiae, include: D13E, T18P, G64A, N76P, S79P/Q/E, T80E/Q, I82L/M, V101I/L, A122E, S133R, S139P, N155E/Q, T156E, G189S/A/E/K, K219Q/A, G239E/N/D, V265T, D271Y/F, Y278F, G293A, S309W/F/L, or S318P/Q/E, with mutant residue numbering based on SEQ ID NO: 6. These point mutations are characterized for protein expression in, for example, Examples 1-3 and Tables I-IV and VI.

In some embodiments of the present invention, combinations of point mutations confer increased Cel5a protein expression. In some embodiments a Cel5a mutant endoglucanase has a combination of point mutations in the Cel5a amino acid sequence, with mutant residue numbering based on SEQ ID NO: 6, including one of the following sets of mutations:

T80E, S133R, N155E, G239E, Y278F, and S318Q;

G189A, F191V, G239D, S242A, V265T, D271Y, S318P/E, and S322A;

E53D, T57N, S79P, T80E, V101I, S133R, N155E, G189S, G239E, D271Y, G293A, S309L, and S318P;

E53D, T57N, S79P, T80E, V101I, S133R, N155E, G189S, G239E, D271Y, G293A, S309W, and S318P;

E53D, T57N, S79P, T80E, V101I, S133R, N155E, G189S, G239E, D271Y, G293A, S309L, and S318E;

E53D, T57N, S79P, T80E, V101I, S133R, N155E, G189S, G239E, D271Y, G293A, S309W, and S318E; or E53D, T57N, S79P, T80E, V101I, S133R, N155E, G189S, F191V, T233V, G239E, V265T, D271Y, G293A, S309W, and S318P.

Excluding the combination set of (T80E, S133R, N155E, G239E, Y278F, and S318Q), the Cel5a combination mutants having increased Cel5a expression as listed above, also have increased thermostability and enzymatic activity as disclosed herein. As such, each of the combinations of point mutations (excluding the indicated combination) produce a Cel5a mutant that is stable at a higher temperature than wild type Cel5a, is more enzymatically active than wild type Cel5a, and is expressed at higher levels.

The following Examples are presented for illustrative purposes only, and do not limit the scope or content of the present application.

Example 1

Identification of D13E, E53D, T57N, G189A, G293A Cel5a Mutants

Experiments were pursued to uncover stabilizing consensus mutations in the primary endoglucanase Cel5a from *Hypocrea jecorina* (HjCel5a), a molecule with ~400 homologous sequences in the NCBI non-redundant protein database. Using this data, six multiple sequence alignments (MSAs) were constructed varying in the number, level of characterization, and percent identity to the query of the aligned sequences. The alignments were filtered with numerical thresholds to reveal highly conserved residues (high relative entropy) at positions able to mutate independently of other protein sites (low mutual information). Using this method, five thermostabilizing point mutations were identified: D13E (+3.0° C.), E53D (+2.7° C.), T57N (+1.1° C.), G189A (+0.4° C.), and G293A (+3.6° C.), with mutant residue numbering based on SEQ ID NO: 6.

Experimental Screening and Validation of Thermostability Enhancing Mutations.

After applying the relative entropy (RE) and mutual information (MI) constraints, a total of 21 unique mutations were predicted as stabilizing from six consensus sequence alignments. Point mutants were constructed, proteins were secreted from *Saccharomyces cerevisiae*, and supernatants were screened for activity on Avicel, a microcrystalline cellulose powder, at a temperature two degrees higher (73° C.) than the wild type (WT) $T_m$ (FIG. 1). As a result of screening supernatant, high signal can indicate greater thermostability, activity, and/or expression, all desirable traits. Mutations D13E, E53D, T57N, I82L, V101L, G189A, and G293A demonstrated greater activity than WT and were selected for further characterization, with mutant residue numbering based on SEQ ID NO: 6.

The seven candidate HjCel5a point mutants were purified and pre-incubated at a gradient of temperatures for 10 minutes (min) before adding Avicel to assess activity over 2 hours at 60° C. Five mutations exhibited a $T_{50}$, the temperature at which half of the total enzyme remains active, greater than WT ($\Delta T_{50,\ D13E}$=3.0, $\Delta T_{50,\ E53D}$=2.7, $\Delta T_{50,\ T57N}$=1.1, $\Delta T_{50,\ G189A}$=0.4, and $\Delta T_{50,\ G293A}$=3.6° C.) (Table I, FIG. 2, FIGS. 3A-3G). The two remaining mutations exhibited slightly lower stabilities than WT ($\Delta T_{50,\ I82L}$=−0.3, $\Delta T_{50,\ V101L}$=−0.4) and likely exhibit high activity on the screen due to increases in expression level (Table I).

TABLE 1

Structural Analysis of Stabilizing Mutations, with mutant residue numbering based on SEQ ID NO: 6

| Mutations | $T_{50,WT}$[a] (° C.) | $T_{50,mut}$ (° C.) | $\Delta T_{50}$ (° C.) | Activity (µM Cellobiose Equivalents) | $\Delta$Activity (µM Cellobiose Equivalents) | Expression Level Relative to WT | Location |
|---|---|---|---|---|---|---|---|
| WT | — | — | — | 193.7 ± 12.23 | 0.0 | — | — |
| D13E | 68.6 ± 0.3 | 71.5 ± 0.4 | 3.0 ± 0.5 | 184.4 ± 1.15 | −9.3 | 1.6 | Core |
| E53D | 68.7 ± 0.3 | 71.4 ± 0.6 | 2.7 ± 0.7 | 201.9 ± 4.91 | 8.2 | 0.9 | Boundary |
| T57N | 71.0 ± 0.0 | 72.1 ± 0.0 | 1.1 ± 0.0 | 240.7 ± 4.08 | 47.0 | 0.3 | Surface |
| G189A | 70.8 ± 0.3 | 71.2 ± 0.3 | 0.4 ± 0.4 | 190.3 ± 3.37 | −3.4 | 1.2 | Boundary |
| G293A | 70.7 ± 0.1 | 74.3 ± 0.1 | 3.9 ± 0.2 | 221.0 ± 1.75 | 27.3 | 0.8 | Core |
| I82L | 69.1 ± 0.4 | 68.9 ± 0.3 | −0.2 ± 0.5 | N/A | N/A | 1.6 | Core |
| V101L | 68.8 ± 0.1 | 68.3 ± 0.3 | −0.5 ± 0.3 | N/A | N/A | 2.3 | Core |

[a]The $T_{50}$ of WT HjCel5A fluctuates by 1° C. due to variables described in the materials and methods section. All mutants were assayed simultaneously with a WT standard.

Activity of Stabilizing Mutations.

Figure 4:
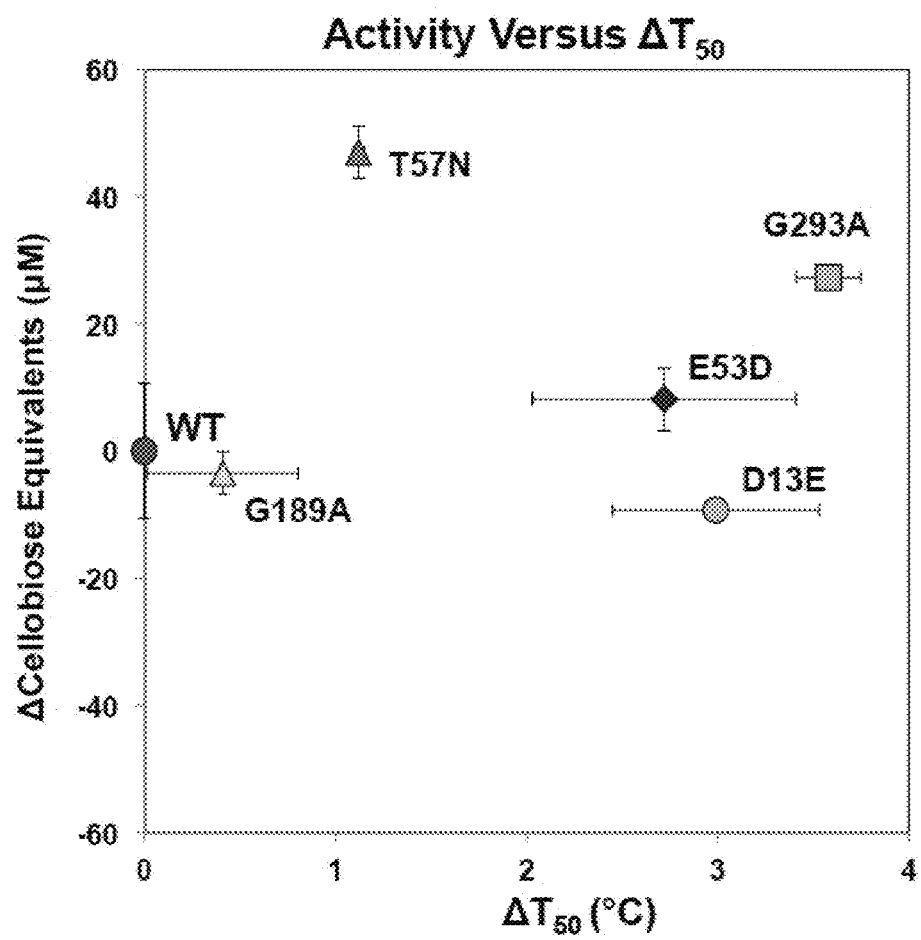
FIG. 4 is a graph showing the cellulase activity of the indicated Cel5a point mutants (with mutant residue numbering based on SEQ ID NO: 6): versus the $\Delta T_{50}$ (compared to wild type Cel5a), where WT (green circle), D13E (pink circle), E53D (dark blue diamond), T57N (light blue triangle), G189A (yellow triangle), and G293A (orange square) are shown, according to embodiments of the present invention.
Figure 5:
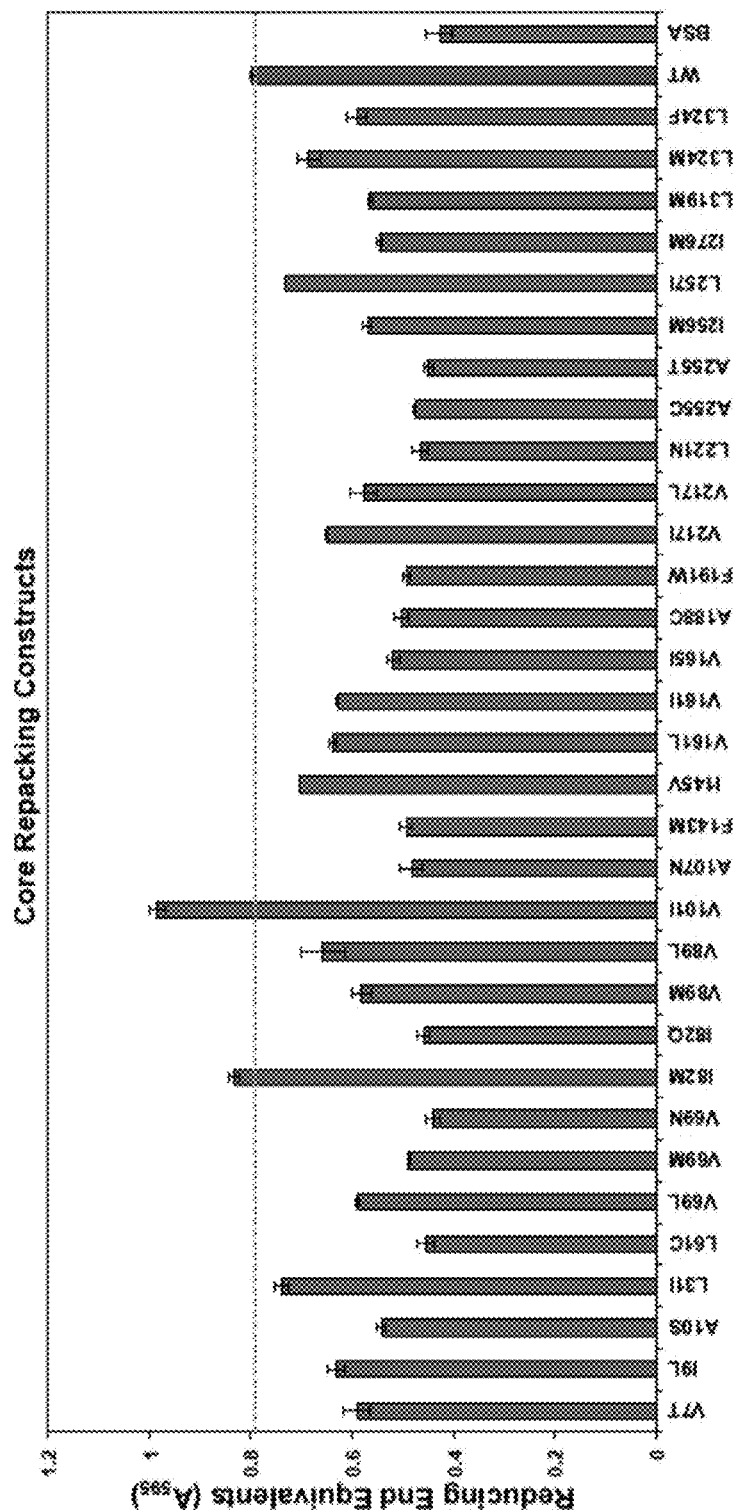
FIG. 5 is a graph measuring thermostability and activity in wild type (WT) and the indicated core repacking Cel5a point mutant proteins (with mutant residue numbering based on SEQ ID NO: 6): following a reducing end (Park-Johnson) assay as described herein, with bovine serum albumin (BSA) used as a control, according to embodiments of the present invention.

To ensure that the stabilizing mutations do not adversely affect enzymatic activity, the five point mutants were tested for hydrolysis on Avicel after 2 hours at 60° C. (FIG. 4). The T57N and G293A mutants show significantly elevated activity, while the activities of the remaining mutants are comparable to WT (Table I).

MSA Construction and Analysis.

Sequences homologous to the catalytic domain of HjCel5a (from GVR to CLARKG) were retrieved using the Position-Specific Iterated BLAST (PSI-BLAST) database search applied to the non-redundant protein sequences National Center for Biotechnology Information (NCBI) database, (Altschul et al. 1997, *Nucleic Acids Research*, 25:3389-3402, the entire contents of which are herein incorporated by reference.) Constraints on the percent identity of the sequences to the query were introduced using the formatting options feature within the BLAST tool, Relative entropy was calculated using the yeast codon probabilities from Sullivan et al. 2012, *J. Molec. Biol.*, 420:384-399, the entire contents of which are herein incorporated by reference.

Cel5a Plasmid Construction.

The Cel5a gene was synthesized by DNA 2.0 (Menlo Park, Calif., USA) with codon frequency optimized for *S. cerevisiae*. The construct consists of an αMFpp8 secretory leader sequence (GenBank BK006949 193648-194145) followed by a region coding for the CBM from the *H. jecorina* CBM (GenBank ABA64553.1) preceded by an extra 'AR' introduced during cloning. This DNA sequence (SEQ. ID NO 2) is

```
5'-GGCTAGACAACAAACAGTATGGGGTCAATGTGGTGGTATTGG

ATGGTCTGGTCCGACAAACTGTGCTCCAGGCTCGGCATGTTCGAC

ACTAAATCCATATTACGCTCAATGTATCCCTGGCGCTACCACTAT

AACAACTTCTACTAGACCACCTTCTGGTCCGACGACAACTACAAG

GGCTACCTCAACCTCTTCCTCTACACCCCCTACTTCCAGC-3'
```

The additional 'AR' sequence does not significantly affect any protein properties. The CBM region is then followed by an HjCel5a catalytic domain sequence identical to GenBank entry JN172972.1. This construct contains a short linker and an N-terminal His-tag. The assembled gene was cloned into the yeast expression vector YEp352/PG-K91-1-ass between the BglII and MboI restriction sites using the Gibson assembly method, as described in Gibson et al. 2009, *Nature Methods*, 6:343-345, the entire contents of which are herein incorporated by reference. Point mutations were introduced using the QuikChange Lightning Site-Directed Mutagenesis Kit from Agilent Technologies (Santa Clara Calif., USA) using primers designed with the online tool provided by Agilent:

Following sequence verification, clones were transformed into YDR483W BY4742 ΔKre2 *S. cerevisiae* cells using the method outlined in Schiestl et al. "Introducing DNA into yeast by transformation," In: Johnston, M, Fields S., Eds., 1993, *Methods: A Companion to Methods in Enzymology*, Acad. Press, Inc. pp. 79-85, the entire contents of which are herein incorporated by reference.

Thermostability/Activity Screen.

*S. cerevisiae* carrying the HjCel5a plasmid were inoculated into 1 mL SD-Ura media in 24-well plates and allowed to grow overnight at 30° C. with shaking at 200 rpm. 4 mL of YPD (yeast extract peptone-dextrose) were added and the cells were allowed to shake at 30° C. for an additional 48 hours before harvesting the supernatant through centrifugation. 5 µL of supernatant, 45 µL of YPD, and 60 µL of a 1.5% Avicel PH-101 (Sigma-Aldrich) slurry in 50 mL sodium acetate, pH 5.0 (cellulase buffer) were combined in a 96-well PCR plate and incubated for 1.5 hours to allow the CBM to bind to the substrate. The bound enzymes were washed three times with cellulase buffer and incubated at 73° C. for 2 hours. Following hydrolysis, 50 µL of the reaction supernatants were tested for reducing sugar concentrations via a modified Park-Johnson assay. All screen samples were run in duplicate.

Park-Johnson Assay.

To detect reducing end release, 50 µL of sample were combined with 100 µL of reagent A (0.5 g L$^{-1}$ K$_3$Fe$_3$(CN)$_6$, 34.84 g L$^{-1}$ PO$_4$K$_2$H, pH 6.0) and 50 µL of reagent B (5.3 g L$^{-1}$ Na$_2$CO$_3$, 0.65 g L$^{-1}$ KCN). In experiments resulting in high amounts of reducing ends, 25 µL of sample is combined with 175 µL of the 2A:1B mixture. After incubating the mixture at 95° C. for 15 minutes in a PCR block, the plate is cooled on ice for five minutes. In a flat well plate, 90 µL of reagent C (2.5 g L$^{-1}$ FeCl$_3$, 10 g L$^{-1}$ polyvinyl pyrrolidone, 2 N H$_2$SO$_4$) is combined with 180 µL of the heat treated sample. The sample is then allowed to incubate for five minutes before measuring absorbance at 595 nm.

Enzyme Purification.

Yeast colonies carrying the HjCel5a plasmid were inoculated into 6 mL of SD-Ura media and grown at 30° C. with shaking at 200 rpm. The preculture was then added to YPD and incubated for 48 hours. Following centrifugation, the supernatant was subjected to an 80% ammonium sulfate precipitation. The mixture was spun for 20 minutes at 8 kg and the pellet resuspended in 20 mL of lysis buffer (50 mM NaH$_2$PO$_4$ pH 7.4, 300 mM NaCl, 10 mM imidazole). Following a pH adjustment to 7.4, the protein was rotated at 4° C.

with 1 mL of Ni-NTA resin (Qiagen) conditioned with lysis buffer for 1 hour. The mixture was loaded into a gravity column, washed with 20 mL of lysis buffer, 20 mL of wash buffer (50 mM NaH$_2$PO$_4$ pH 7.4, 300 mM NaCl, 20 mM imidazole), and eluted with 6 mL of elution buffer (50 mM NaH$_2$PO$_4$ pH 7.4, 300 mM NaCl, 250 mM imidazole). After concentrating the elution to 0.5 mL, the protein was further purified and buffer exchanged into cellulase buffer through size exclusion chromatography. Protein concentrations were determined through measuring absorbance at 280 nm ($\epsilon_{280}$=81950 cm$^{-1}$ M$^{-1}$).

T$_{50}$ Assay.

To assess thermostability via enzymatic activity, 40 µL of protein at a concentration of 0.25 µM was added to a PCR plate in triplicate for each of 12 temperatures. Enzyme was pretreated from 60-80° C. for ten minutes, then allowed to cool for an additional five minutes. 60 µL of a 1.5% Avicel slurry in cellulase buffer was added to each well and the plates were incubated at 60° C. for an hour. The plates were promptly cooled for 5 minutes on ice then centrifuged for 5 minutes to pellet the Avicel. Activity assessment with the Park-Johnson assay immediately followed using a 50 µL sample volume. To compare T$_{50}$ values, the data were scaled from 0 to 1 using the following equation:

$$\text{Fraction Active} = \frac{(A_T - A_{min})}{(A_{max} - A_{min})}$$

In the above equation, $A_T$ is the activity as measured by $A_{595}$ at a particular temperature, $A_{min}$ is the lowest observed activity, and $A_{max}$ is the highest observed activity for a particular protein. T$_{50}$ values were derived from generating curve fits using the Hill equation:

$$\text{Curve Fit} = \frac{T^n}{T^n + m^n}$$

Here n is the Hill coefficient, m is the T$_{50}$, and T is the temperature. Values for n and m were solved using the curve fit tool in MATLAB. (MATLAB and Statistics Toolbox Release 2011, The MathWorks, Inc., Natick, Mass., United States, the entire contents of which are herein incorporated by reference.) Because the T$_{50}$ can fluctuate by approximately 1° C. depending on fluctuations in Avicel milling, subtle changes in cooling time, and PCR plate edge effects, all samples were run simultaneously with a WT standard. The ΔT$_{50}$ values are calculated as T$_{50, mut}$-T$_{50, WT}$.

Single-Point Activity Assay.

To determine enzyme activity, 40 µL of enzyme at 0.5 µM was combined with 60 µL of 1.5% Avicel in a PCR plate. The mixture was incubated at 60° C. for two hours to allow hydrolysis to proceed. After cooling the plate on ice for 5 minutes, 100 µL of 0, 50, 100, 150, 200, 250, 300, and 350 µM cellobiose standards were added to the plate in triplicate. The plate was centrifuged to pellet the Avicel and 25 µL of the samples were extracted to perform a Park Johnson activity assay. All samples were tested in triplicate.

Example 2

Figures 6A, 6B:
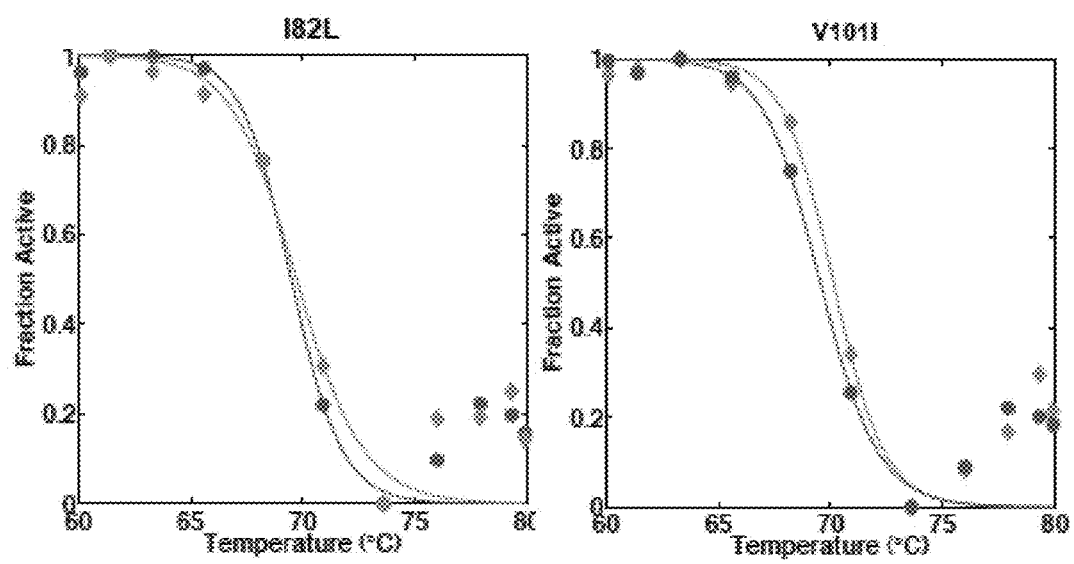
FIG. 6A is a $T_{50}$ plot for the Cel5a I82L mutant of FIG. 5, where the fraction active reflects the amount of the total protein that is active after a 10 minute heat treatment from 60-80° C., where WT (green) and the point mutant (yellow) are shown, according to embodiments of the present invention.
FIG. 6B is a $T_{50}$ plot for the Cel5a V101I mutant of FIG. 5, where the fraction active reflects the amount of the total protein that is active after a 10 minute heat treatment from 60-80° C., where WT (green) and the point mutant (yellow) are shown, according to embodiments of the present invention.
Figure 7:
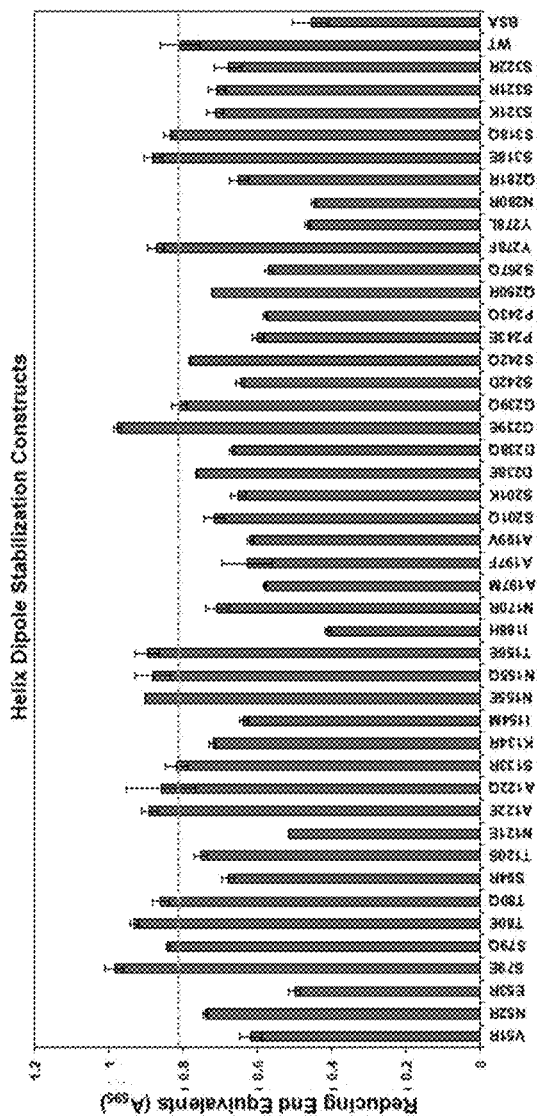
FIG. 7 is a graph measuring thermostability and activity in wild type (WT) and the indicated helix dipole Cel5a point mutant proteins (with mutant residue numbering based on SEQ ID NO: 6): following a reducing end (Park-Johnson) assay as described herein, with bovine serum albumin (BSA) used as a control, according to embodiments of the present invention.

Identification of S79Q, T80E, I82M, V101I, S133R, N155E, N155Q, T156E, G239E, Y278F, S318E, and S318Q Cel5a Mutants Utilizing a core repacking algorithm, 32 HjCel5a mutations were identified, with mutant residue numbering based on SEQ ID NO: 6. These 32 mutations were individually cloned as point mutations and screened for stability and adequate activity (FIG. 5), following methods disclosed in Example 1. Supernatants harboring secreted protein were screened for activity after incubation for 1 hour at 73° C., 3.5 degrees higher than the WT T$_m$ (69.5° C.). Only two mutations with activities exceeding WT were detected from the screening step—I82M and V101I. Two variants, each carrying one of these stabilizing mutations were expressed and purified to assess thermostability more directly. Both mutants showed a slight increase in thermostability with I82M conferring a 0.3 and V101I a 0.5° C. increase in T$_{50}$, the temperature at which half of the maximal protein activity persists (Table II, FIGS. 6A, 6B).

TABLE II

Characterization of stabilizing mutants, with mutant residue numbering based on SEQ ID NO: 6

| Construct | T$_{50,WT}$ (° C.) | T$_{50,mut}$ (° C.) | ΔT$_{50}$ (° C.) | Activity (µM Cellobiose Equivalents) | ΔActivity (µM Cellobiose Equivalents) | ΔΔG[b] (kcal mol$^{-1}$) | Site MI[b] | Expression Level Relative to WT |
|---|---|---|---|---|---|---|---|---|
| WT | — | — | — | 193.7 ± 12.2 | 0 | — | — | — |
| Core Mutations | | | | | | | | |
| I82M | 69.5 ± 0.2 | 69.8 ± 0.5 | 0.3 ± 0.5 | 188.5 ± 2.4 | −5.2 | −0.9 | 0.48 | 1.3 |
| V101I | 69.6 ± 0.3 | 70.1 ± 0.2 | 0.5 ± 0.4 | 210.1 ± 1.8 | 16.4 | −0.4 | 0.29 | 1.7 |
| Helix Mutations | | | | | | | | |
| T80E | 69.3 ± 0.2 | 69.8 ± 0.1 | 0.5 ± 0.2 | 203.6 ± 9.2 | 9.8 | 2.7 | 0.73 | 2.3 |
| S133R | 68.9 ± 0.1 | 69.4 ± 0.1 | 0.4 ± 0.2 | 197.1 ± 2.6 | 3.4 | 1.8 | 0.88 | 1.8 |
| N155E | 69.5 ± 0.3 | 70.0 ± 0.1 | 0.5 ± 0.3 | 199.4 ± 1.1 | 5.6 | 0.5 | 0.69 | 4.9 |
| N155Q | 68.4 ± 0.1 | 68.5 ± 0.1 | 0.1 ± 0.1 | 172.8 ± 4.0 | −20.9 | 0.1 | 0.69 | 1.1 |
| T156E | 69.5 ± 0.2 | 69.7 ± 0.3 | 0.2 ± 0.3 | 217.6 ± 7.9 | 23.9 | 1.2 | 0.98 | 4.9 |
| G239E | 69.7 ± 0.1 | 70.0 ± 0.3 | 0.2 ± 0.3 | 216.9 ± 6.5 | 23.2 | −0.2 | 0.96 | 1.0 |
| Y278F | 69.2 ± 0.2 | 70.2 ± 0.4 | 1.0 ± 0.5 | 174.7 ± 2.7 | −19.1 | 1.3 | 0.64 | 0.4 |
| S318E | 69.7 ± 0.2 | 70.5 ± 0.1 | 0.9 ± 0.2 | 244.1 ± 4.3 | 50.4 | −0.5 | N/A[a] | 0.6 |
| S318Q | 68.9 ± 0.1 | 69.4 ± 0.2 | 0.5 ± 0.2 | 196.0 ± 2.4 | 2.3 | −0.3 | N/A[a] | 0.9 |
| S79Q | 69.4 ± 0.2 | 69.5 ± 0.2 | 0.0 ± 0.3 | 174.4 ± 5.1 | −19.3 | 0.4 | 0.61 | 1.4 |
| S79E | 69.9 ± 0.2 | 69.7 ± 0.0 | −0.1 ± 0.2 | N/A | N/A | −0.3 | 0.61 | 5.5 |
| T80Q | 69.2 ± 0.2 | 69.1 ± 0.1 | −0.1 ± 0.2 | N/A | N/A | 3.2 | 0.73 | 2.0 |

TABLE II-continued

Characterization of stabilizing mutants,
with mutant residue numbering based on SEQ ID NO: 6

| Construct | $T_{50,WT}$ (° C.) | $T_{50,mut}$ (° C.) | $\Delta T_{50}$ (° C.) | Activity (μM Cellobiose Equivalents) | ΔActivity (μM Cellobiose Equivalents) | $\Delta\Delta G^b$ (kcal mol$^{-1}$) | Site MI$^b$ | Expression Level Relative to WT |
|---|---|---|---|---|---|---|---|---|
| A122E | 69.0 ± 0.5 | 68.8 ± 0.2 | −0.2 ± 0.5 | N/A | N/A | 1.0 | 0.51 | 3.2 |
| G239Q | 69.1 ± 0.1 | 68.5 ± 0.1 | −0.9 ± 0.2 | N/A | N/A | −1.6 | 0.96 | 0.9 |
| Helix Combo | 69.5 ± 0.5 | 71.9 ± 0.3 | 2.4 ± 0.5 | N/A | N/A | N/A | N/A | 4.5 |

($^a$Insufficient homologous sequence data. $^b$Values calculated from the 444 sequence MSA of Example 1.)

Figures 8A, 8B:
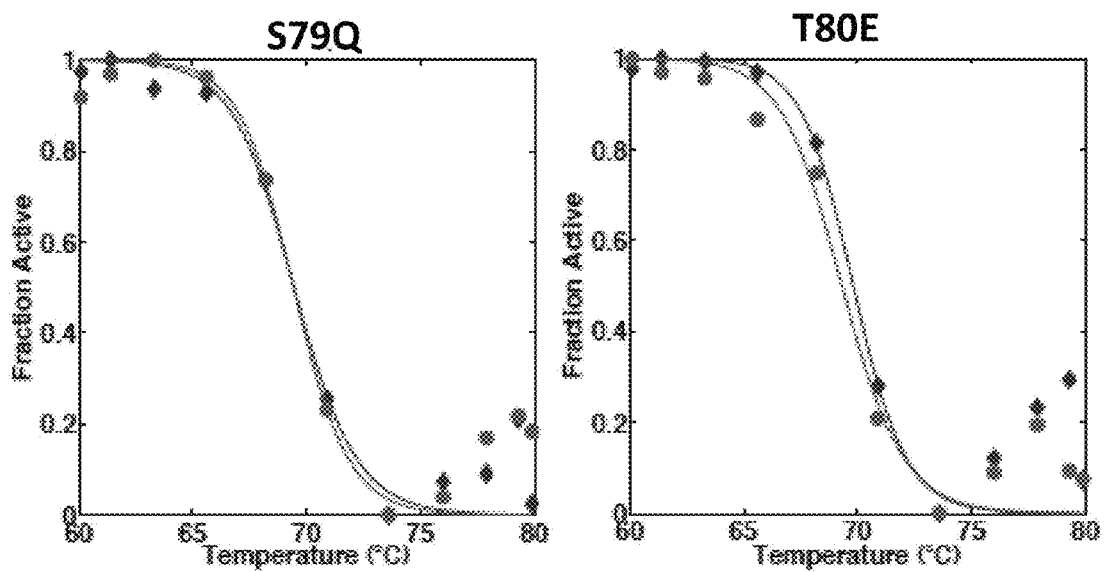
FIG. 8A is a $T_{50}$ plot for the Cel5a S79Q mutant of FIG. 7, where the fraction active reflects the amount of the total protein that is active after a 10 minute heat treatment from 60-80° C., where WT (green) and the point mutant (yellow) are shown, according to embodiments of the present invention.
FIG. 8B is a $T_{50}$ plot for the Cel5a T80E mutant of FIG. 7, where the fraction active reflects the amount of the total protein that is active after a 10 minute heat treatment from 60-80° C., where WT (green) and the point mutant (yellow) are shown, according to embodiments of the present invention.
Figure 8E:
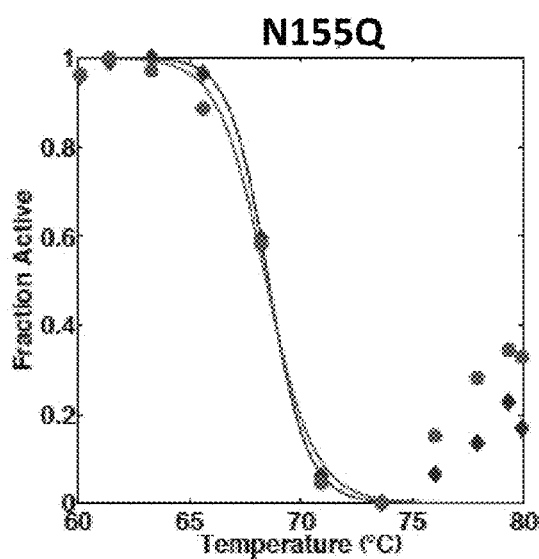
FIG. 8E is a $T_{50}$ plot for the Cel5a N155Q mutant of FIG. 7, where the fraction active reflects the amount of the total protein that is active after a 10 minute heat treatment from 60-80° C., where WT (green) and the point mutant (yellow) are shown, according to embodiments of the present invention.
Figure 8F:
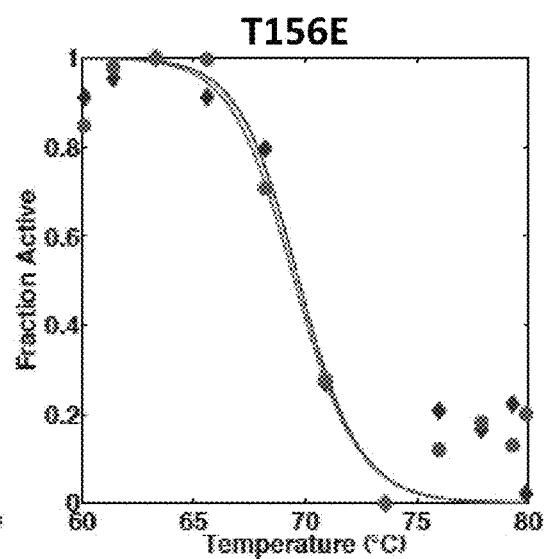
FIG. 8F is a $T_{50}$ plot for the Cel5a T156E mutant of FIG. 7, where the fraction active reflects the amount of the total protein that is active after a 10 minute heat treatment from 60-80° C., where WT (green) and the point mutant (yellow) are shown, according to embodiments of the present invention.
Figure 8G:
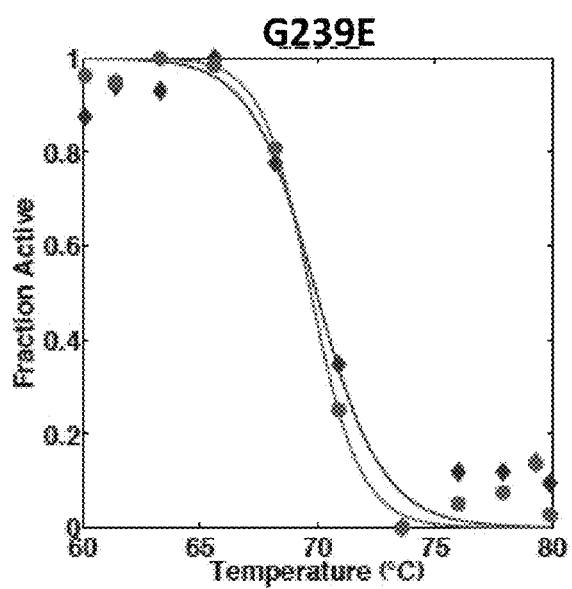
FIG. 8G is a $T_{50}$ plot for the Cel5a G239E mutant of FIG. 7, where the fraction active reflects the amount of the total protein that is active after a 10 minute heat treatment from 60-80° C., where WT (green) and the point mutant (yellow) are shown, according to embodiments of the present invention.
Figure 8H:
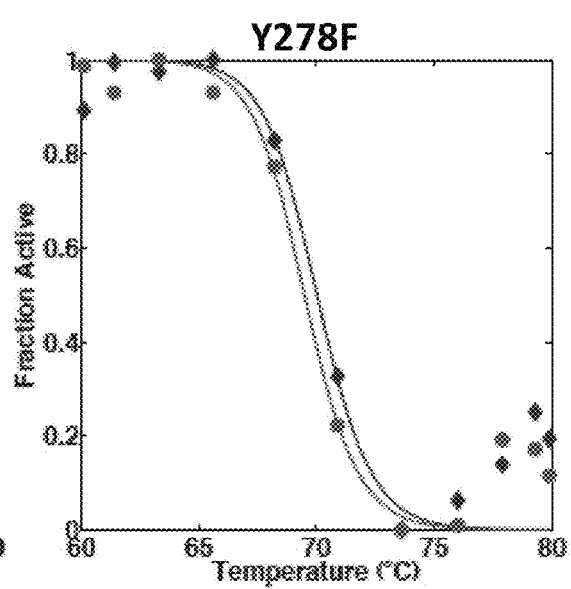
FIG. 8H is a $T_{50}$ plot for the Cel5a Y278F mutant of FIG. 7, where the fraction active reflects the amount of the total protein that is active after a 10 minute heat treatment from 60-80° C., where WT (green) and the point mutant (yellow) are shown, according to embodiments of the present invention.
Figure 8I:
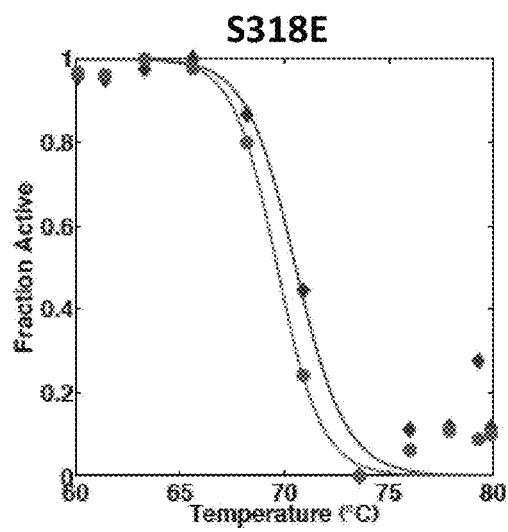
FIG. 8I is a $T_{50}$ plot for the Cel5a S318E mutant of FIG. 7, where the fraction active reflects the amount of the total protein that is active after a 10 minute heat treatment from 60-80° C., where WT (green) and the point mutant (yellow) are shown, according to embodiments of the present invention.
Figure 8J:
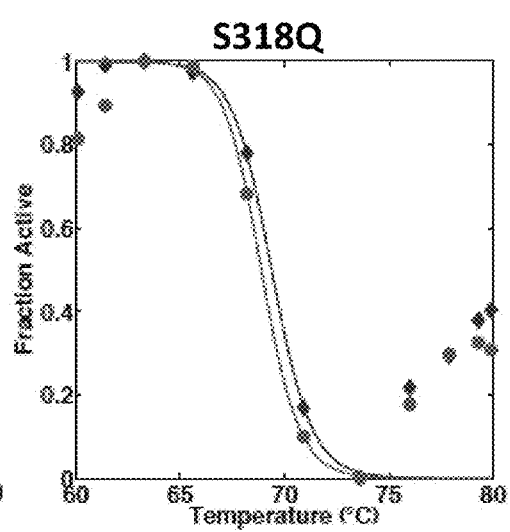
FIG. 8J is a $T_{50}$ plot for the Cel5a S318Q mutant of FIG. 7, where the fraction active reflects the amount of the total protein that is active after a 10 minute heat treatment from 60-80° C., where WT (green) and the point mutant (yellow) are shown, according to embodiments of the present invention.
Figure 8K:
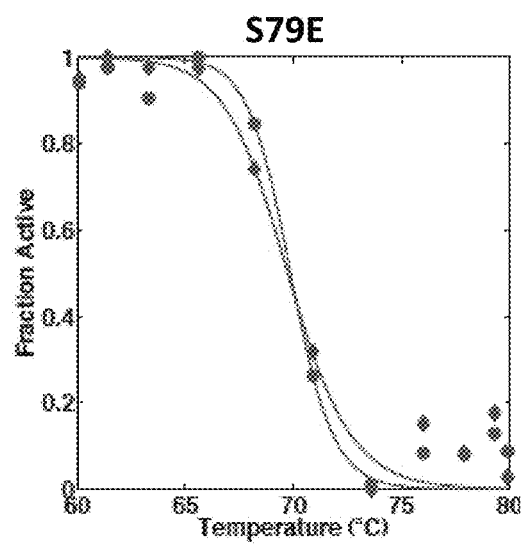
FIG. 8K is a $T_{50}$ plot for the Cel5a S79E mutant of FIG. 7, where the fraction active reflects the amount of the total protein that is active after a 10 minute heat treatment from 60-80° C., where WT (green) and the point mutant (yellow) are shown, according to embodiments of the present invention.
Figure 8L:
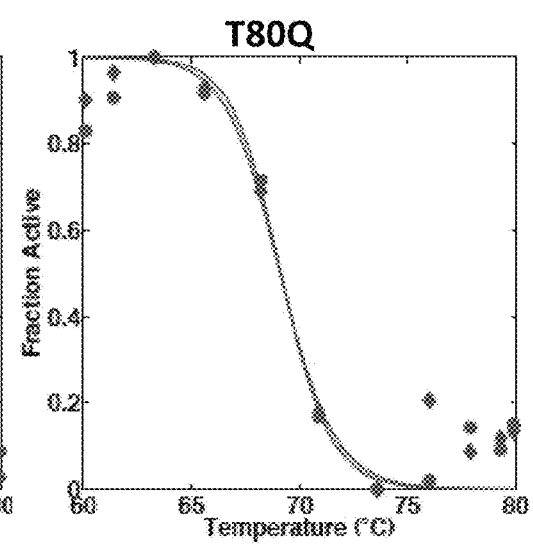
FIG. 8L is a $T_{50}$ plot for the Cel5a T80Q mutant of FIG. 7, where the fraction active reflects the amount of the total protein that is active after a 10 minute heat treatment from 60-80° C., where WT (green) and the point mutant (yellow) are shown, according to embodiments of the present invention.
Figure 8M:
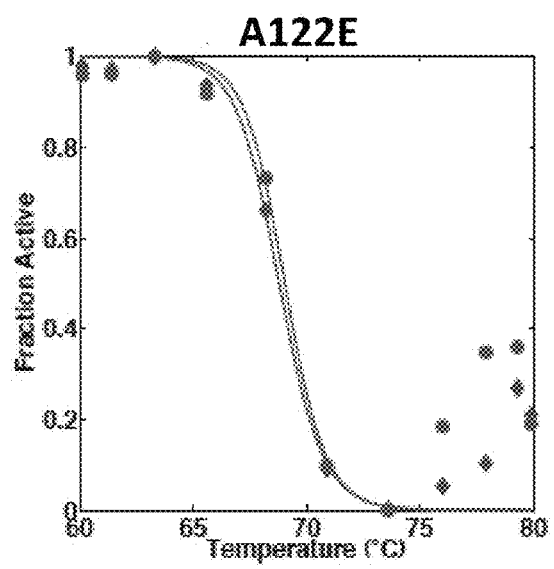
FIG. 8M is a $T_{50}$ plot for the Cel5a A122E mutant of FIG. 7, where the fraction active reflects the amount of the total protein that is active after a 10 minute heat treatment from 60-80° C., where WT (green) and the point mutant (yellow) are shown, according to embodiments of the present invention.
Figure 8N:
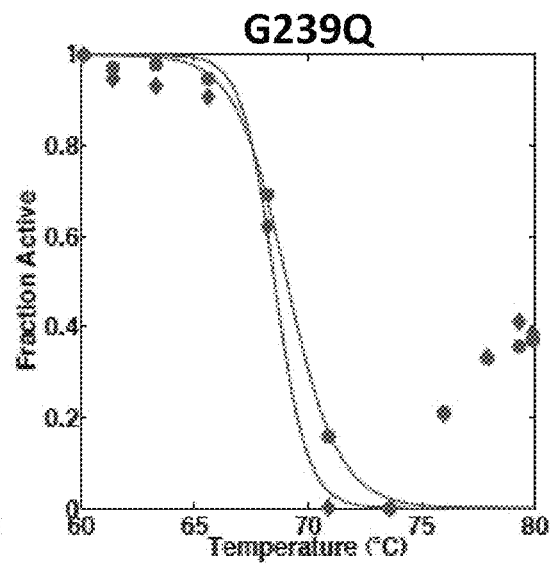
FIG. 8N is a $T_{50}$ plot for the Cel5a G239Q mutant of FIG. 7, where the fraction active reflects the amount of the total protein that is active after a 10 minute heat treatment from 60-80° C., where WT (green) and the point mutant (yellow) are shown, according to embodiments of the present invention.

A helix dipole stabilization calculation as developed by Marshall et al. was used to select 44 predicted helix mutations. (Marshall et al. 2002, *J. of Molec. Biol.*, 316:189-199, the entire contents of which are herein incorporated by reference.) These 44 predicted helix mutations were constructed as point mutants and screened for activity (FIG. 7) with the same procedure used to probe core mutations. In the activity screen, 14 constructs demonstrated greater activity than WT. Following purification and activity screening at a gradient of temperatures, nine constructs demonstrated a positive $\Delta T_{50}$ (T80E, S133R, N155E, N155Q, T165E, G239E, Y278F, S318E, and S318Q), four showed a decrease in thermostability (S79E, T80Q, A122E, and G239Q), and one behaved similarly to WT (S79Q) (Table II, FIGS. 8A-8N), with mutant residue numbering based on SEQ ID NO: 6. As is the case with the core mutations, the helix dipole stabilizing mutations provide modest stability benefits ($\Delta T_{50} \leq 1°$ C.). Only five of the nine stabilizing mutations exhibit a $\Delta T_{50} \geq 0.5°$ C.

Figure 9A:
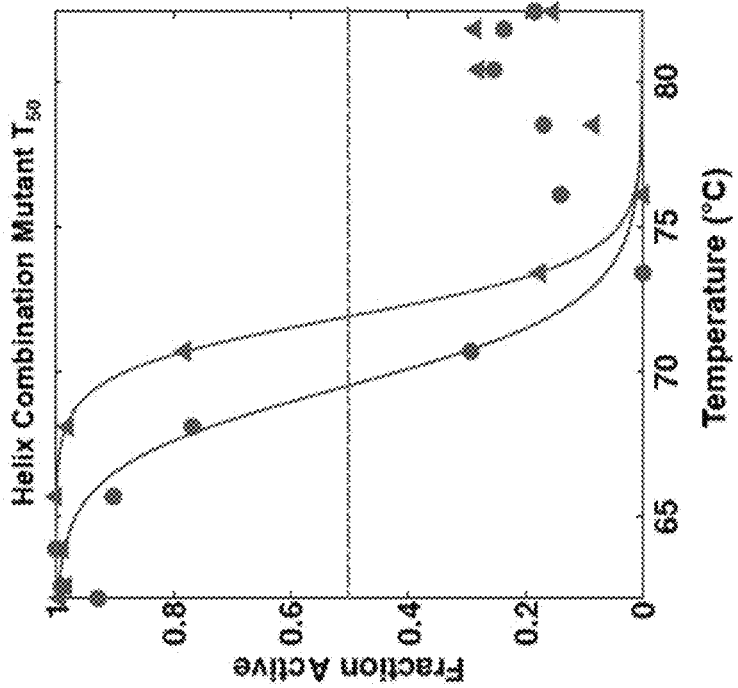
FIG. 9A is a graph measuring the reducing ends equivalents (Park-Johnson assay) for Cel5a WT (green circles) and Helix combo mutant (blue triangles) proteins (with mutant residue numbering based on SEQ ID NO: 6) over a range of temperatures as indicated, according to embodiments of the present invention.
Figure 9B:
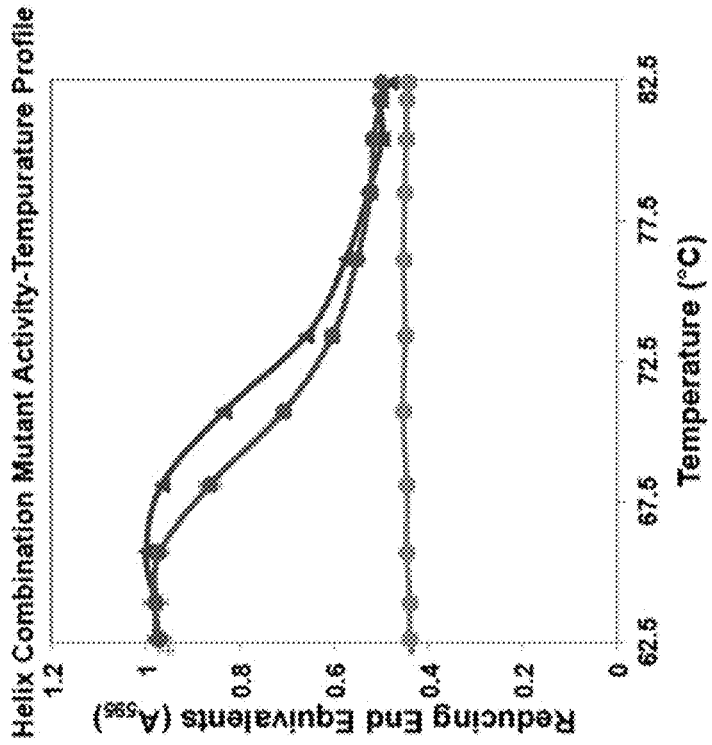
FIG. 9B is a $T_{50}$ plot for the Cel5a WT and Helix combo mutant of FIG. 9A, where the fraction active reflects the amount of the total protein that is active after a 10 minute heat treatment from 60-80° C., where WT (green circles) and the Helix combo mutant (blue triangles) are shown, according to embodiments of the present invention.

Given the relatively low enhancements in thermostability observed for the helix dipole stabilizing mutations, it remained unclear whether these mutations would provide any tangible benefit. A combination construct (Helix combo) containing the T80E, S133R, N155E, G239E, Y278F, and S318Q mutations, with mutant residue numbering based on SEQ ID NO: 6, was constructed and the $\Delta T_{50}$ (2.4° C.) and optimal reaction temperature ($T_{opt,helix\ combo}$=66° C., $T_{opt,WT}$=63.5° C.) were determined (FIGS. 9A-9B). Both values show modest increases of ~2.5° C. While the six stabilizing mutations did not additively increase $T_{50}$ and $T_{opt}$, the combination mutant still demonstrates improved thermostability compared to the most beneficial helix point mutant. In addition, the combination mutant shows a 4.5 fold improvement in expression over WT (Table II).

Activity of Stabilized Mutants.

Figure 10A:
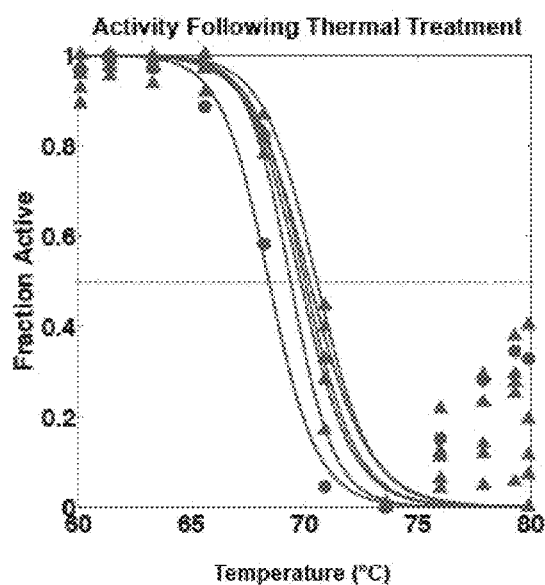
FIG. 10A is a $T_{50}$ plot for the Cel5a WT and core repacking point mutations having a $\Delta T_{50} > 0.5°$ C., where the fraction active reflects the amount of the total protein that is active after a 10 minute heat treatment from 60-80° C., where WT (green circles) and core repacking mutants (blue triangles) are shown, according to embodiments of the present invention.
Figure 10B:
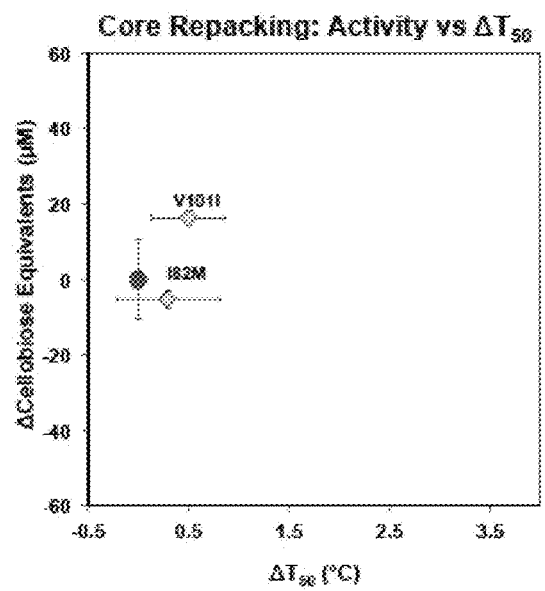
FIG. 10B is a graph showing the cellulase activity of the indicated core repacking Cel5a point mutants (with mutant residue numbering based on SEQ ID NO: 6) versus the $\Delta T_{50}$ (compared to wild type Cel5a), where WT (green circle) and the indicated core repacking mutants (yellow diamonds) are shown, according to embodiments of the present invention.
Figure 10C:
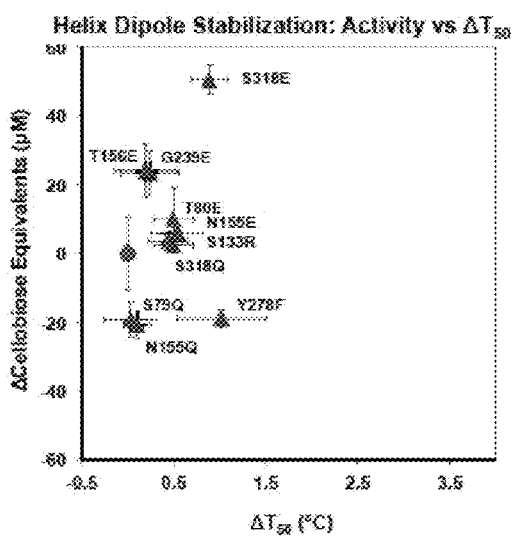
FIG. 10C is a graph showing the cellulase activity of the indicated helix dipole Cel5a point mutants (with mutant residue numbering based on SEQ ID NO: 6) versus the $\Delta T_{50}$ (compared to wild type Cel5a), where WT (green circle) and the indicated helix dipole mutants (blue diamonds) are shown, according to embodiments of the present invention.
Figure 11A:
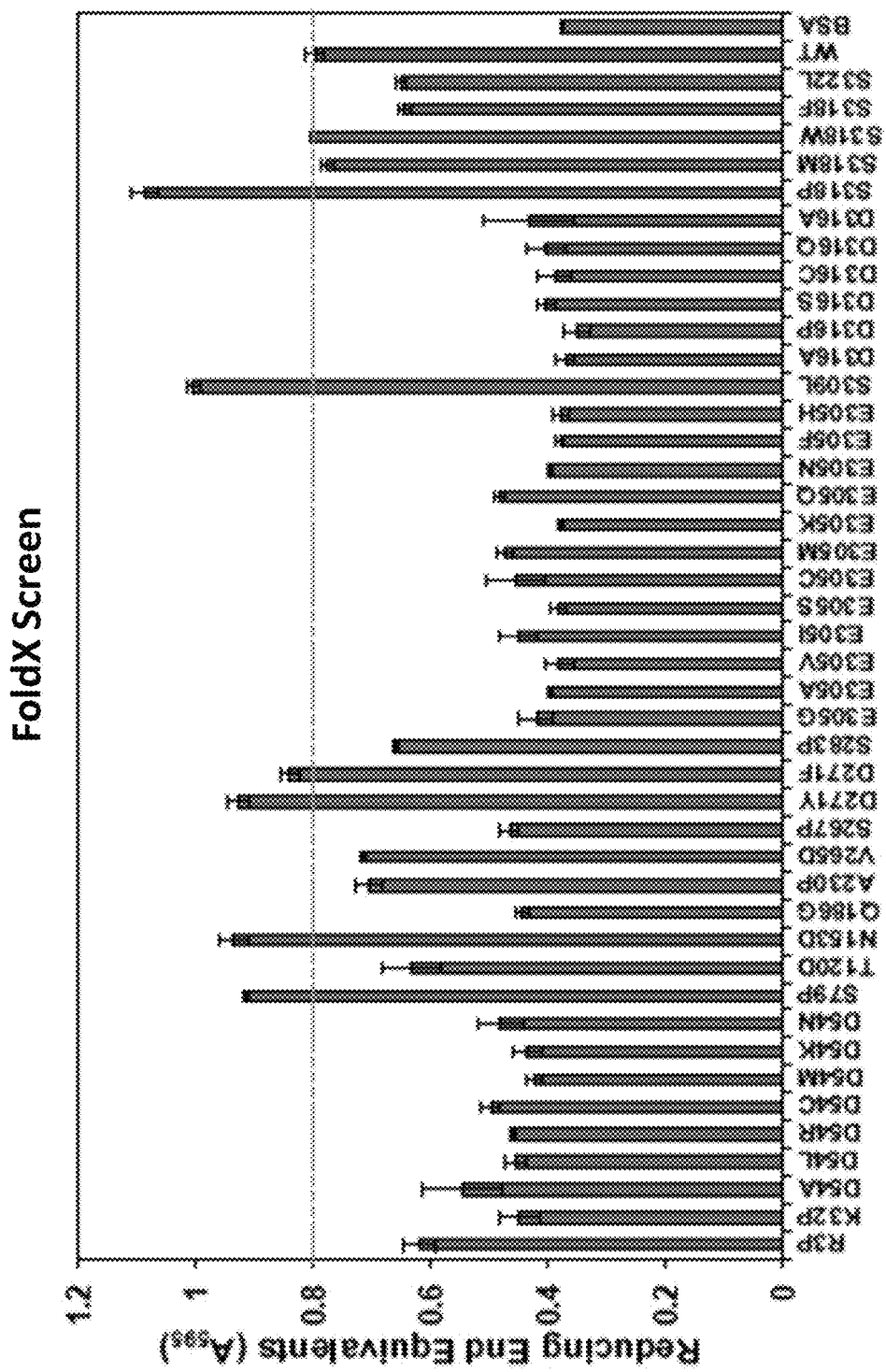
FIG. 11A is a graph measuring thermostability and activity in wild type (WT) and the indicated Cel5a point mutant proteins (with mutant residue numbering based on SEQ ID NO: 6) selected from a FoldX screen as described herein, with bovine serum albumin (BSA) used as a control, according to embodiments of the present invention.
Figure 11B:
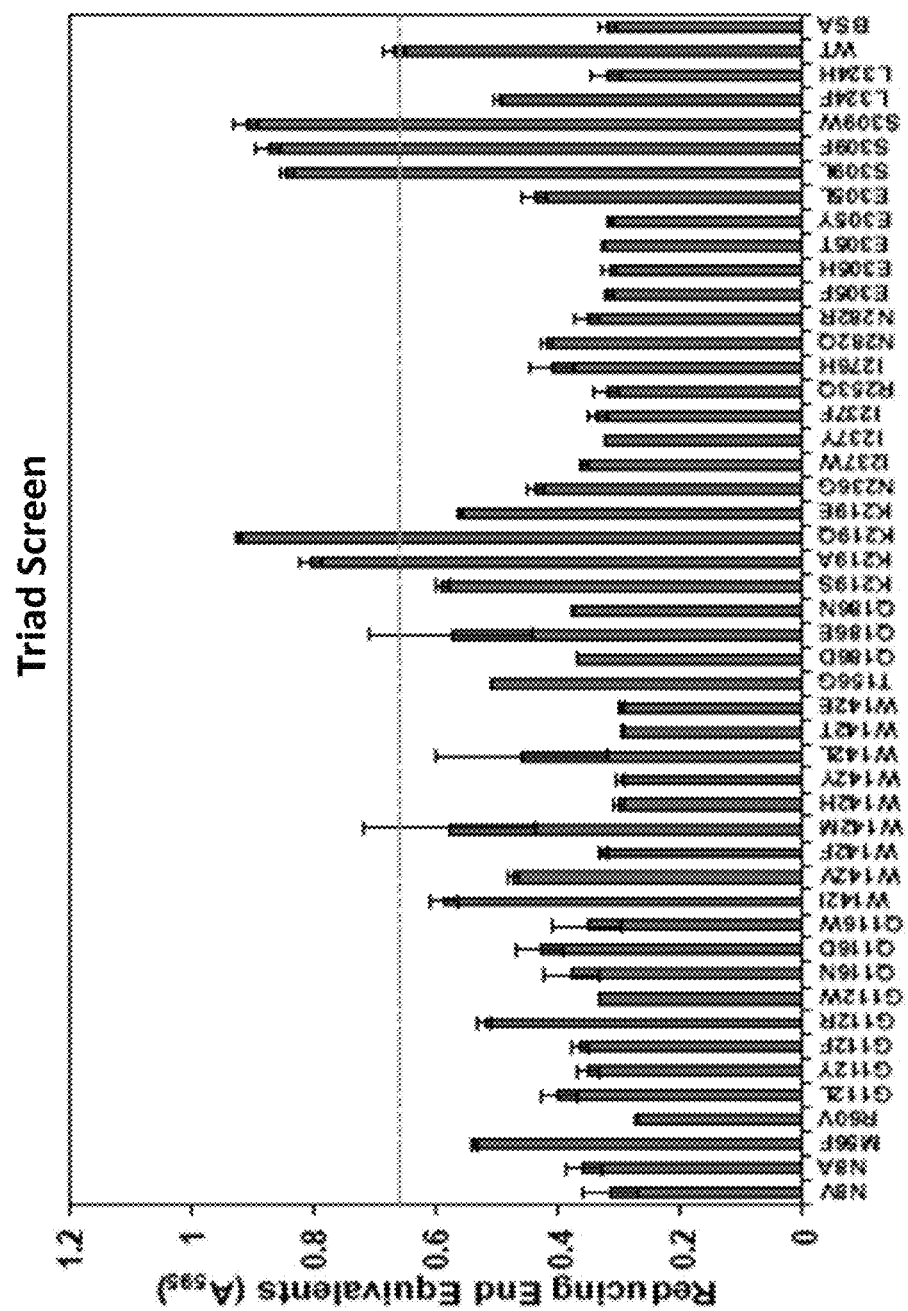
FIG. 11B is a graph measuring thermostability and activity in wild type (WT) and the indicated Cel5a point mutant proteins (with mutant residue numbering based on SEQ ID NO: 6) selected from a Triad screen as described herein, with bovine serum albumin (BSA) used as a control, according to embodiments of the present invention.
Figure 12A:
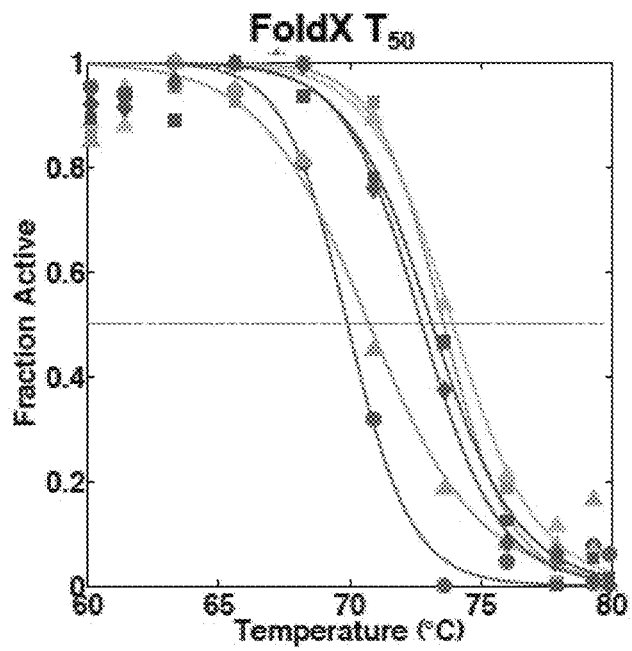
FIG. 12A is a graph corresponding to thermostability and activity of FIG. 11A showing the amount of activity versus an increase in temperature of the wild type (green) and the indicated FoldX Cel5a mutants (with mutant residue numbering based on SEQ ID NO: 6): N153D (pink triangles), D271F (orange squares), D271Y (yellow triangles), S309L (blue diamonds), and S319P (green squares), where the dashed line indicates the point at which 50% of the maximal protein activity persists ($T_{50}$), according to embodiments of the present invention.
Figure 12B:
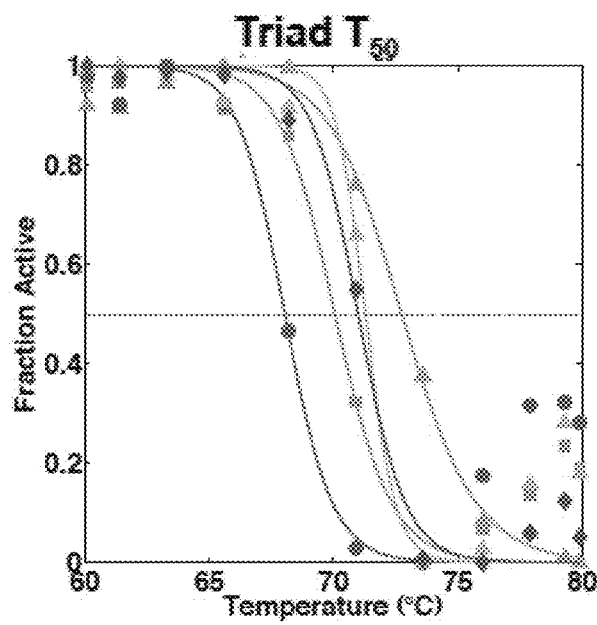
FIG. 12B is a graph corresponding to thermostability and activity of FIG. 11B showing the amount of activity versus an increase in temperature of the wild type (green) and the indicated Triad Cel5a mutants (with mutant residue numbering based on SEQ ID NO: 6): K219A (orange squares), K219Q (yellow triangles), S309F (blue diamonds), and S309L (pink triangles), where the dashed line indicates the point at which 50% of the maximal protein activity persists ($T_{50}$), according to embodiments of the present invention.
Figure 13A:
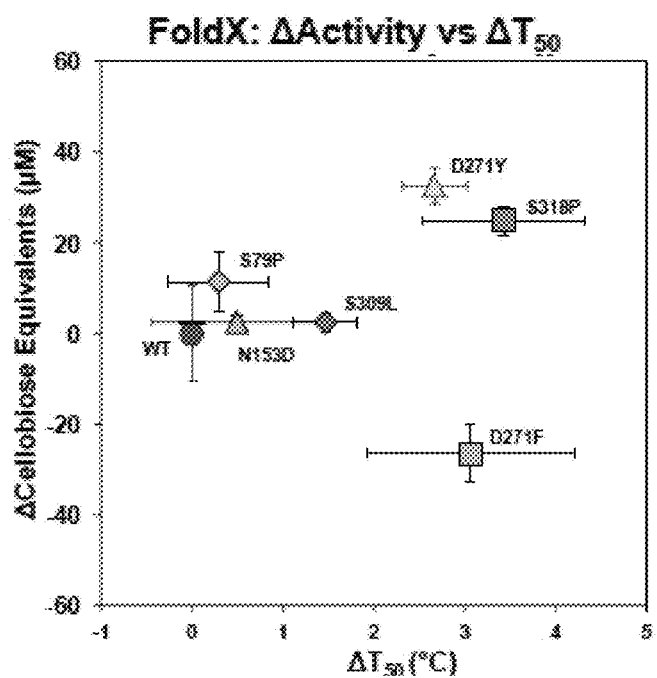
FIG. 13A is a graph showing the cellulase activity of the indicated FoldX Cel5a point mutants (with mutant residue numbering based on SEQ ID NO: 6) versus the $\Delta T_{50}$ (compared to wild type Cel5a), as indicated in FIG. 12A, according to embodiments of the present invention.
Figure 13B:
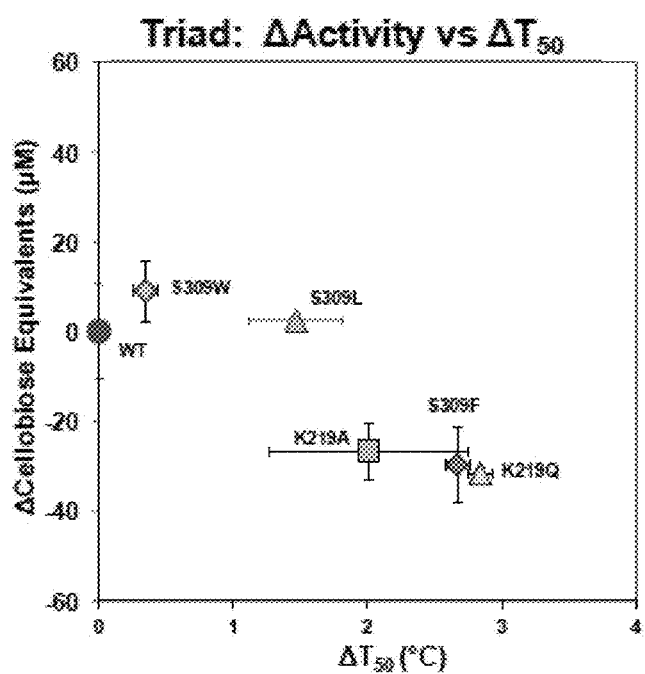
FIG. 13B is a graph showing the cellulase activity of the indicated Triad Cel5a point mutants (with mutant residue numbering based on SEQ ID NO: 6) versus the $\Delta T_{50}$ (compared to wild type Cel5a), as indicated in FIG. 12B, according to embodiments of the present invention.
Figure 14A:
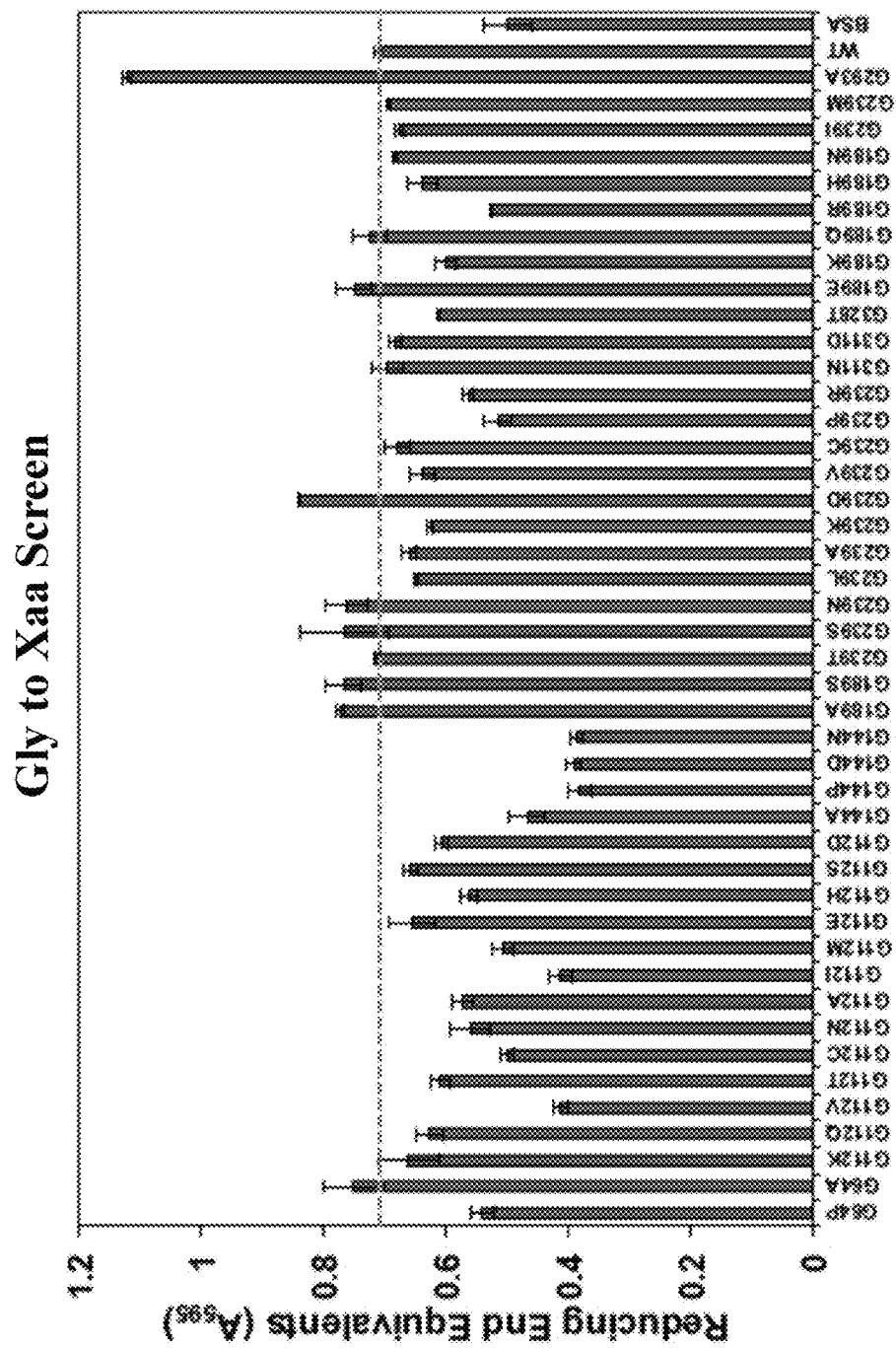
FIG. 14A is a graph measuring thermostability and activity in wild type (WT) and the indicated Glycine to Xaa Cel5a point mutant proteins (with mutant residue numbering based on SEQ ID NO: 6) following a reducing end (Park-Johnson) assay as described herein, with bovine serum albumin (BSA) used as a control, according to embodiments of the present invention.
Figure 14B:
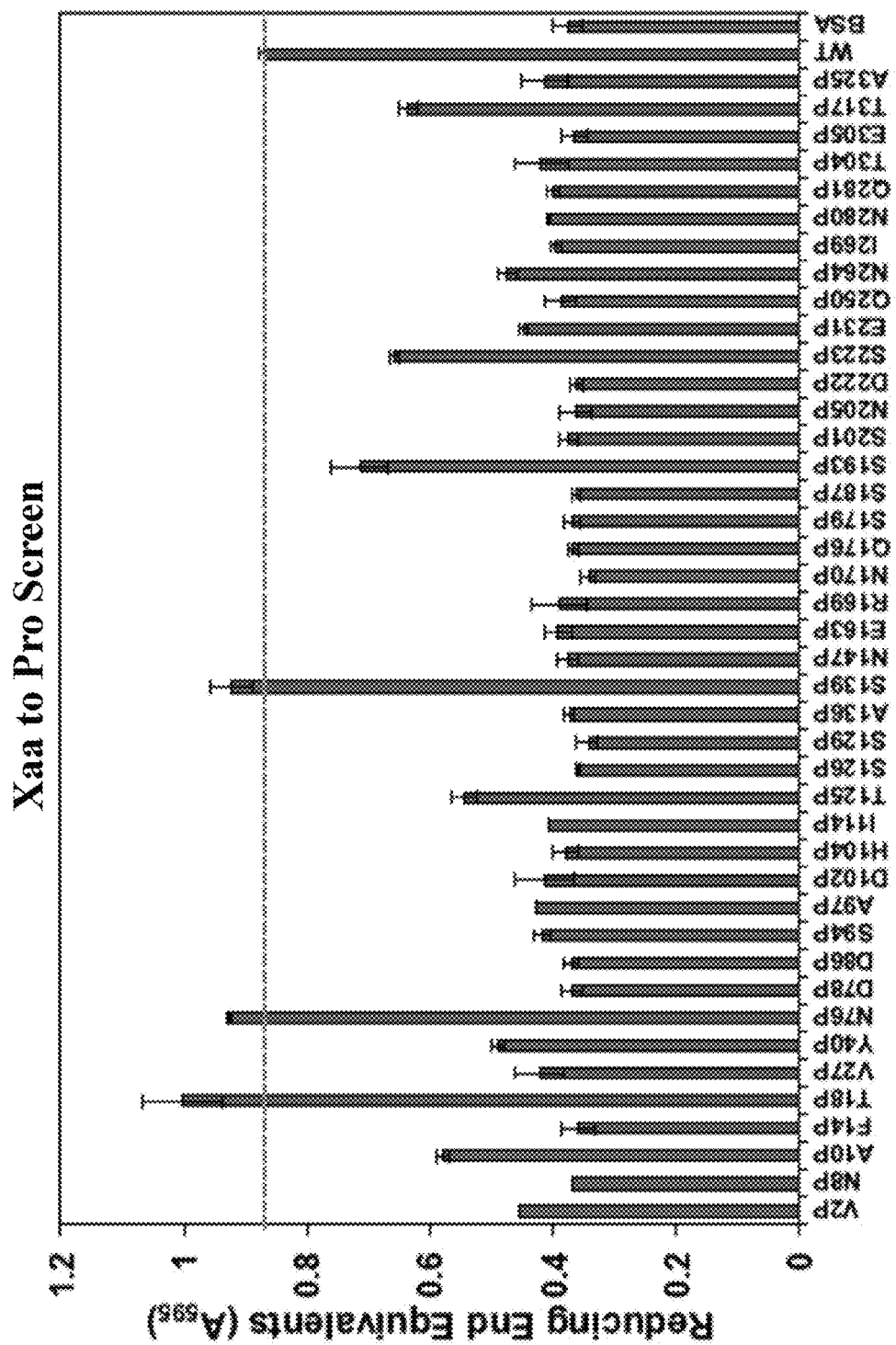
FIG. 14B is a graph measuring thermostability and activity in wild type (WT) and the indicated Xaa to Proline Cel5a point mutant proteins (with mutant residue numbering based on SEQ ID NO: 6) following a reducing end (Park-Johnson) assay as described herein, with bovine serum albumin (BSA) used as a control, according to embodiments of the present invention.
Figure 15B:
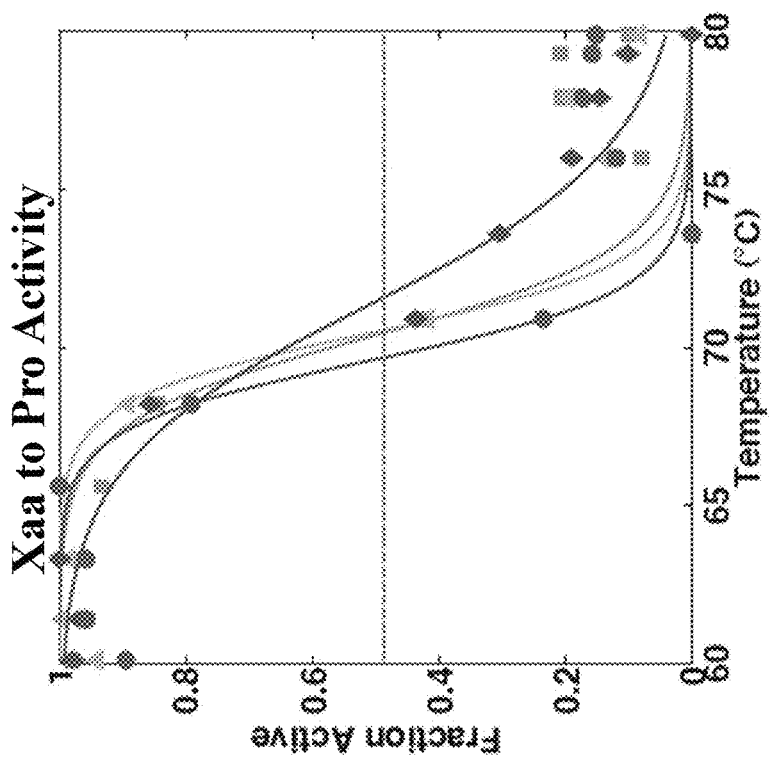
FIG. 15B is a $T_{50}$ plot for the Cel5a WT and Xaa to Proline point mutations (with mutant residue numbering based on SEQ ID NO: 6), where the fraction active reflects the amount of the total protein that is active after a 10 minute heat treatment from 60-80° C., where WT (grey circles) and T18P (orange squares), N76P (yellow triangles), and S139P (blue diamonds) are shown, according to embodiments of the present invention.
Figure 15A:
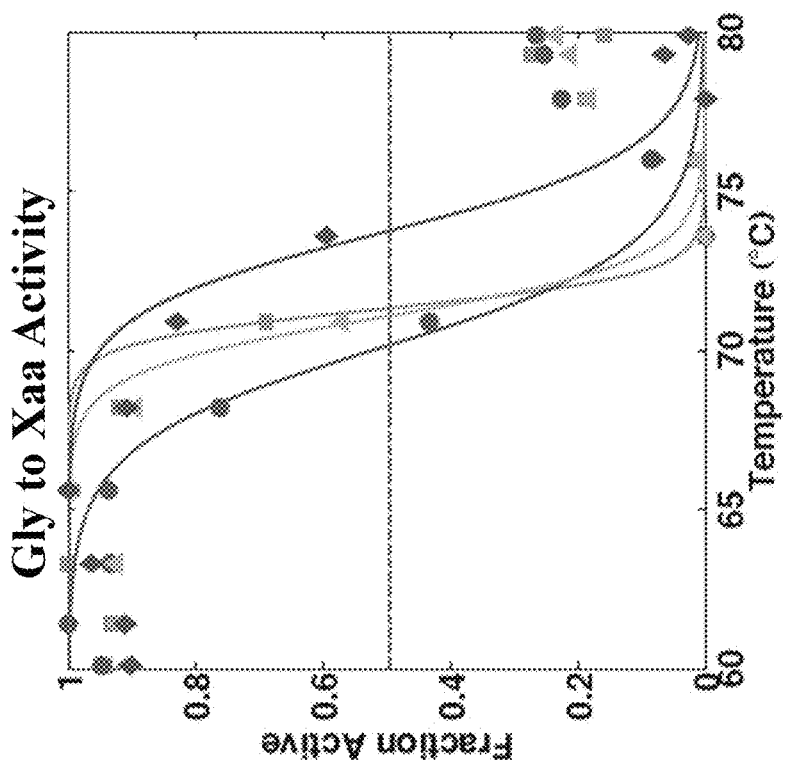
FIG. 15A is a $T_{50}$ plot for the Cel5a WT and Gly to Xaa point mutations (with mutant residue numbering based on SEQ ID NO: 6), where the fraction active reflects the amount of the total protein that is active after a 10 minute heat treatment from 60-80° C., where WT (grey circles) and G189S (orange squares), G239N (yellow triangles), and G293A (blue diamonds) are shown, according to embodiments of the present invention.
Figure 16B:
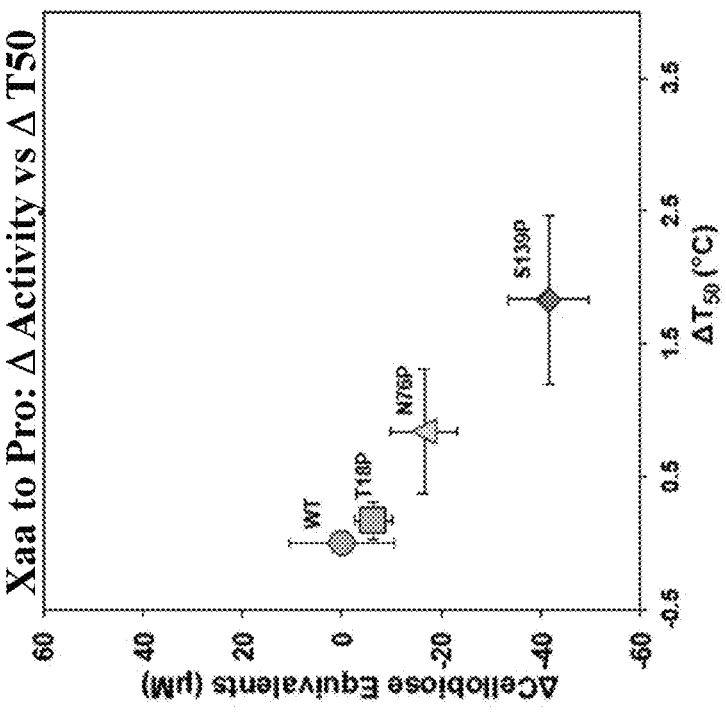
FIG. 16B is a graph showing the A cellulase activity (compared to wild type Cel5a) of the indicated Xaa to Proline Cel5a point mutants (with mutant residue numbering based on SEQ ID NO: 6) versus the $\Delta T_{50}$ (compared to wild type Cel5a), as indicated in FIG. 15B, according to embodiments of the present invention.
Figure 16A:
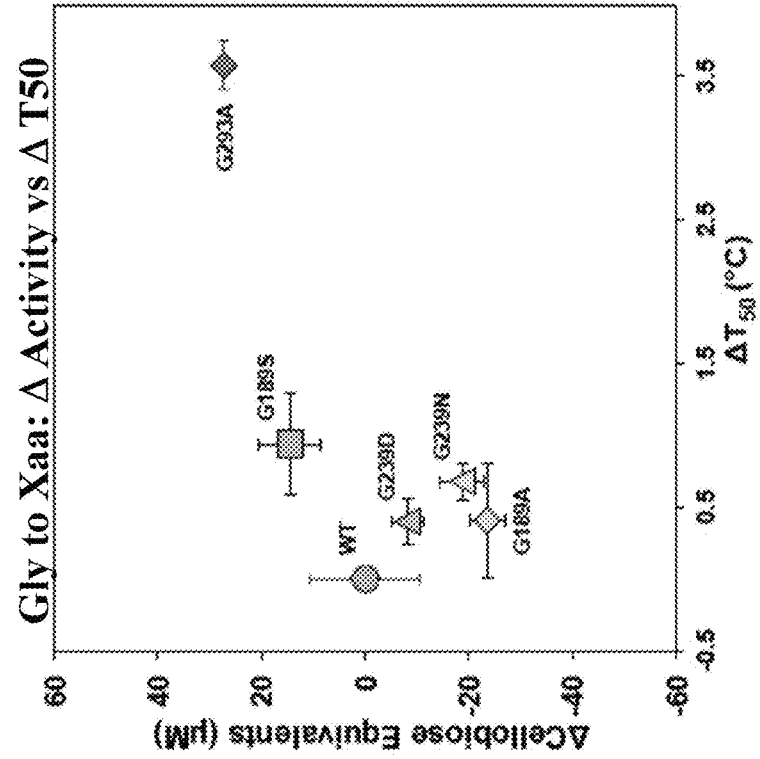
FIG. 16A is a graph showing the A cellulase activity (compared to wild type Cel5a) of the indicated Gly to Xaa Cel5a point mutants (with mutant residue numbering based on SEQ ID NO: 6) versus the $\Delta T_{50}$ (compared to wild type Cel5a), as indicated in FIG. 15A, according to embodiments of the present invention.

Useful enzyme mutations not only confer stability, but also elevate or preserve activity. The activity of each stabilizing point mutation was tested at 60° C. for two hours on Avicel, a crystalline cellulose powder (Table II). While the two stabilizing core mutants have activities comparable to WT (FIGS. 10A, 10B), the helix mutations show an even distribution between lower and higher activities (FIG. 10C).

Expression.

In addition to preserving activity, desirable mutations will also maintain or enhance protein expression levels. Five of the helix dipole stabilizing hits on the activity screen were either neutral or destabilizing. Four of these mutations confer greater protein expression than WT in *S. cerevisiae*, which is the probable cause for their high activity in the screen. In general, the point mutants and helix combination mutant demonstrated large increases in expression level (Table II). The catalytic domain of HjCel5a V101I was expressed in *Escherichia coli*, resulting in a three-fold increase in protein yield.

Structure preparation.

Designs were performed on chain A of the HjCel5a crystal structure (PDB ID 3QR3)(SEQ ID NO: 6). (Lee et al. 2011, *Protein Science*, 20:1935-1940, the entire contents of which are herein incorporated by reference.) After removing water molecules and ions, hydrogens were added to the structure using the protein process application within the design software TRIAD (Triad, 2012, Protabit, LLC, Pasadena, Calif.). This application was additionally employed to optimize the structure through 50 steps of gradient-based energy minimization using the energy function described in the computational design section.

Computational Design.

Computational design parameters outlined in this section were kept consistent between the core repacking and helix dipole stabilization calculations. All calculations were executed using an energy function based on the DREIDING forcefield that includes terms for van der Waals hydrogen bonding, electrostatics, implicit solvation, and phi-psi propensities. (Mayo et al. 1990, *J. of Phys. Chem.*, 94:8897-8909; Dahiyat et al. 1997, *PNAS*, 94:10172-10177; and Dahiyat et al. 1997, *Prot. Science*, 6:1333-1337, the entire contents of all of which are herein incorporated by reference.) In calculating the implicit solvation term, an occlusion-based solvation potential was applied with scale factors of 0.05 for nonpolar burial, 2.5 for nonpolar exposure, and 1.0 for polar burial, as described in Chica et al. 2010, *PNAS*, 107:20257-20262, the entire contents of which are herein incorporated by reference. Sequence optimization was performed with FASTER and a Monte Carlo-based algorithm was used to sample sequences near the minimum energy sequence. (Allen et al. 2006, *J. Computational Chem.*, 27:1071-1075; Desmet et al. 2002, *Proteins: Structure, Function, and Bioinformatics*, 48:31-43; Metropolis et al. 1953, *J. of Chem Physics*, 21:1087-1092; and Voigt et al. 2000, *J of Molec. Biol.*, 299:789-801 the entire contents of all of which are herein incorporated by reference.

Cel5a Plasmid Construction.

Cel5a mutants were constructed as described in Example 1.

Thermostability/Activity Screen.

Thermostability and activity screens were performed as described in Example 1.

$T_{opt}$ Assay.

To assess the optimal operating temperature of HjCel5a constructs, 40 μL of protein at a concentration of 0.25 μM was combined with 60 μL of a 1.5% Avicel slurry in cellulose buffer in a PCR plate in triplicate for each of 12 temperatures. The plates were incubated at 60° C. for two hours and promptly cooled for 5 minutes on ice. After centrifugation for 5 minutes to pellet the insoluble substrate, activity was assessed with the Park-Johnson assay as described in Example 1, using a 25 μL sample volume. Bovine serum albumin (BSA) at a final concentration identical to the protein of interest served as a negative control.

Enzyme Purification.

Cel5a proteins were cultured and purified as described in Example 1.

$T_{50}$ Assay.

The T50 assay was performed as described in Example 1.

Single-Point Activity Assay.

The single-point activity assay was performed as described in Example 1.

Example 3

Identification of T18P, N76P, S79P, S139P, N153D, G189A, G189S, G189E, G189Q, K219A, K219Q, G239S, G239D, G239N, D271Y, D271F, G293A, S309L, S309F, S309W, S318P, Cel5a Mutants FoldX Designs.

In silico site-saturated mutagenesis was performed on chain A from the HjCel5a crystal structure (PDB ID 3QR3). Out of 6,232 possible point mutations, FoldX predicted 1008 as stabilizing ($\Delta\Delta G<0$ kcal mol$^{-1}$). As this sizeable pool of candidate mutations was too large to screen using available resources, mutations with a $\Delta\Delta G \leq -1.75$ kcal mol$^{-1}$ were examined. In addition, the energy cutoff was tightened from $-0.75$ to $-1.75$ kcal mol$^{-1}$ as described in Komor et al. 2012, *Prot. Eng. Des. Sel.*, 25:827-833, the entire contents of which is herein incorporated by reference. Applying this stringent criterion reduced the candidate pool to 43 mutations.

Triad $\Delta\Delta G$ Designs. In parallel to the FoldX designs, site-saturated mutagenesis using Triad was used with the Rosetta forcefield and the HjCel5a crystal structure. Out of 6,232 possible point mutations, 789 were predicted as stabilizing ($\Delta\Delta G<0$). To reduce the number of candidate mutations to a manageable quantity, an arbitrary $-1.75$ kcal mol$^{-1}$ cutoff was applied leaving 47 mutations.

Detecting Stabilizing Mutations.

Point mutants for each of the 43 FoldX and 44 Triad mutations were constructed for secretion in *Saccharomyces cerevisiae*. Proteins were expressed and the supernatant was screened for activity at 73° C., 3.5 degrees higher than the melting temperature ($T_m$) of the native protein. Six FoldX and five Triad mutants demonstrated higher activity than wild type (WT) and were selected for more rigorous characterization.

As the screen was performed on unpurified protein in supernatant, hits may indicate a variant with improved thermostability, yield, activity, or a combination thereof. To determine the source of their improvement, the mutants and WT were simultaneously assayed for activity at 60° C. following a 10 minute incubation at a gradient of temperatures ranging from 60-80° C. The $T_{50}$, the temperature at which half of the maximum protein activity persists, of the mutation was computed and compared to the WT value. All of the mutations proved more thermostable than WT ($\Delta T_{50}>0°$ C.), as summarized in Table III below, with mutant residue numbering based on SEQ ID NO: 6.

FoldX predicted three highly stabilizing mutations, D271F ($\Delta T_{50}=3.1°$ C.), D271Y ($\Delta T_{50}=2.7°$ C.), and S318P ($\Delta T_{50}=3.2°$ C.), with mutant residue numbering based on SEQ ID NO: 6. Similarly, three mutations among the Triad predictions, K219A ($\Delta T_{50}=2.0°$ C.), K219Q ($\Delta T_{50}=2.8°$ C.), and S309F ($\Delta T_{50}=2.7°$ C.), conferred significant increases in stability, with mutant residue numbering based on SEQ ID NO: 6. The mutant expression levels were similar or lower than WT.

Activity of Stabilizing FoldX and Triad Mutants.

To determine whether the stabilizing FoldX and Triad mutations impact activity, purified protein was assayed for activity after 2 hours at 60° C. (Table III, FIGS. 11A, 11B and 13A, 13B). While the Rosetta mutations show decreased activity compared to WT, the FoldX mutations exhibit more diversity in activity. Notably, the FoldX mutations S318P and D271Y elevate the WT activity by 12.8 and 16.8%.

Backbone Stabilization: Removing Glycines and Adding Prolines.

To test the hypothesis that adapting empirical methods to improve backbone stability may provide additional stabilizing mutations, all Gly→$X_{AA}$ and $X_{AA}$→Pro mutations were fetched and ranked by $\Delta\Delta G$ value. All of the mutations with $\Delta\Delta G$ values≤0 kcal mol$^{-1}$ were designated as potentially stabilizing. This relaxed cutoff allowed for the prediction of mutations that did not pass the $-1.75$ kcal mol$^{-1}$ threshold enforced in the general Triad $\Delta\Delta G$ calculation. Only five mutual members appear in both the general Triad and glycine mutation lists. In addition, all predicted proline mutations were previously uncharacterized.

In total, 51 glycine and 46 proline mutations were predicted as stabilizing. Due to screening constraints, only the top 44 glycine (FIG. 14A) and 46 proline (FIG. 14B) mutants were constructed and screened using the setup described for the FoldX and Rosetta constructs. Nine glycine and three proline mutants demonstrated higher activity than WT on the screen. After purifying these enzymes and determining their $\Delta T_{50}$s, five glycine (G189A $\Delta T_{50}=0.4°$ C., G189S $\Delta T_{50}=1.2°$ C., G239D $\Delta T_{50}=0.4°$ C., G239N $\Delta T_{50}=0.7°$ C., and G293A $\Delta T_{50}=3.5°$ C.) and three proline mutations (T18P $\Delta T_{50}=2.0°$ C., N76P $\Delta T_{50}=2.0°$ C., and S139P $\Delta T_{50}=2.0°$ C.) demonstrated thermostability benefits (Table IV, FIGS. 15A-15B, 16A-16B), with mutant residue numbering based on SEQ ID NO: 6.

TABLE III

Characterization of FoldX and Triad $\Delta\Delta G$ mutations

| Construct | $T_{50,WT}$ (° C.) | $T_{50,mut}$ (° C.) | $\Delta T_{50}$ (° C.) | Activity (μM Cellobiose Equivalents) | $\Delta$Activity (μM Cellobiose Equivalents) | FoldX $\Delta\Delta G$ (kcal mol$^{-1}$) | Triad $\Delta\Delta G$ (kcal mol$^{-1}$) | Expression Level (Mut/WT) | Location |
|---|---|---|---|---|---|---|---|---|---|
| WT | — | — | — | 193.7 ± 12.2 | 0.0 | — | — | — | |
| FoldX | | | | | | | | | |
| S79P | 69.9 ± 0.3 | 70.2 ± 0.5 | 0.3 ± 0.5 | 205.1 ± 6.7 | 11.4 | −1.84 | 0.97 | 1.0 | Surface |
| N153D | 70.3 ± 0.7 | 70.7 ± 0.6 | 0.5 ± 0.9 | 196.2 ± 1.5 | 2.5 | −2.91 | −0.25 | 0.2 | Surface |
| D271F | 70.5 ± 0.9 | 73.6 ± 0.6 | 3.1 ± 1.1 | 167.2 ± 6.3 | −26.5 | −2.23 | −1.08 | 0.1 | Boundary |
| D271Y | 71.3 ± 0.3 | 73.9 ± 0.1 | 2.7 ± 0.4 | 209.5 ± 3.9 | 32.5 | −1.83 | −1.07 | 0.4 | Boundary |
| S309L | 71.3 ± 0.3 | 72.7 ± 0.3 | 1.5 ± 0.3 | 196.1 ± 1.9 | 2.4 | −1.78 | −2.26 | 0.8 | Boundary |
| S318P | 69.9 ± 0.6 | 73.1 ± 0.6 | 3.2 ± 0.9 | 218.5 ± 3.4 | 24.8 | −2.32 | 3.27 | 0.3 | Surface |
| Triad | | | | | | | | | |
| K219A | 68.1 ± 0.7 | 70.1 ± 0.1 | 2.0 ± 0.7 | 167.0 ± 6.2 | −26.7 | 2.07 | −3.20 | 1.4 | Core |
| K219Q | 68.5 ± 0.0 | 71.3 ± 0.1 | 2.8 ± 0.1 | 162.0 ± 1.4 | −31.7 | 1.28 | −1.92 | 1.2 | Core |
| S309F | 68.3 ± 0.1 | 71.0 ± 0.1 | 2.7 ± 0.1 | 164.1 ± 8.6 | −29.7 | −0.57 | −1.94 | 0.8 | Boundary |
| S309L | 71.3 ± 0.3 | 72.7 ± 0.3 | 1.5 ± 0.3 | 196.1 ± 1.9 | 2.4 | −1.78 | −2.26 | 0.8 | Boundary |
| S309W | 68.2 ± 0.0 | 68.6 ± 0.1 | 0.4 ± 0.1 | 202.8 ± 6.8 | 9.1 | 0.19 | −2.24 | 0.5 | Boundary |

TABLE IV

Backbone stabilizing mutations

| Construct | $T_{50,WT}$ (°C.) | $T_{50,mut}$ (°C.) | $\Delta T_{50}$ (°C.) | Activity (μM Cellobiose Equivalents) | ΔActivity (μM Cellobiose Equivalents) | FoldX ΔΔG (kcal mol$^{-1}$) | Triad ΔΔG (kcal mol$^{-1}$) | Expression Level (Mut/WT) | Location |
|---|---|---|---|---|---|---|---|---|---|
| WT | — | — | — | 193.7 ± 12.2 | 0 | — | — | — | |
| | | | | GLY → $X_{AA}$ | | | | | |
| G189A | 70.8 ± 0.3 | 71.2 ± 0.3 | 0.4 ± 0.4 | 170.1 ± 3.4 | −23.7 | −0.93 | −0.76 | 1.2 | Boundary |
| G189S | 70.1 ± 0.3 | 71.3 ± 0.2 | 1.2 ± 0.4 | 208.2 ± 6.0 | 14.5 | −0.45 | −0.97 | 1.2 | Boundary |
| G239D | 70.8 ± 0.1 | 71.2 ± 0.1 | 0.4 ± 0.2 | 185.6 ± 3.1 | −8.1 | −0.80 | −1.46 | 1.3 | Boundary |
| G239N | 70.4 ± 0.1 | 71.1 ± 0.0 | 0.7 ± 0.1 | 174.9 ± 4.3 | −18.8 | −0.13 | −1.43 | 1.1 | Boundary |
| G293A | 70.3 ± 0.1 | 73.7 ± 0.1 | 3.5 ± 0.2 | 221.0 ± 1.2 | 27.3 | 6.66 | −0.08 | 0.8 | Core |
| G189E | 70.6 ± 0.1 | 70.6 ± 0.2 | 0.0 ± 0.2 | N/A | N/A | −0.58 | −1.01 | 2.0 | Boundary |
| G64A | 70.3 ± 0.1 | 69.6 ± 0.1 | −0.7 ± 0.1 | 190.5 ± 5.0 | −3.2 | 2.97 | −0.30 | 2.3 | Core |
| G189K | 70.6 ± 0.1 | 70.5 ± 0.1 | −0.1 ± 0.2 | N/A | N/A | −0.89 | −0.55 | 1.2 | Boundary |
| G239S | 70.8 ± 0.2 | 69.7 ± 0.3 | −1.0 ± 0.3 | N/A | N/A | −0.20 | −1.04 | 0.9 | Boundary |
| | | | | $X_{AA}$ → PRO | | | | | |
| T18P | 70.2 ± 0.1 | 70.4 ± 0.0 | 0.2 ± 0.1 | 187.5 ± 3.8 | −6.2 | −1.67 | 0.46 | 1.1 | Surface |
| N76P | 69.7 ± 0.2 | 70.5 ± 0.4 | 0.8 ± 0.5 | 177.3 ± 6.8 | −16.4 | 0.00 | 0.95 | 1.7 | Surface |
| S139P | 69.6 ± 0.2 | 71.5 ± 0.6 | 1.8 ± 0.6 | 152.1 ± 8.0 | −41.6 | −1.33 | 2.14 | 1.8 | Surface |
| | | | | Disulfide Mutations | | | | | |
| I44C/G91C | 69.8 ± 0.4 | 69.3 ± 0.5 | −0.5 ± 0.7 | N/A | N/A | N/A | N/A | 0.8 | Surface/Boundary |

FoldX Calculation.

All FoldX calculations were performed with version 3.0, as described in Schymokowitz et al. 2005, *Nucl. Acids Research*, 33:W382-W388, the entire contents of which are herein incorporated by reference. After removing waters and ligands, Chain A from the HjCel5a crystal structure (PDB ID: 3QR3)(SEQ ID NO: 6) was prepared using the optimize and repair PDB functions within the software. A position scan was performed to compute energy values for WT and mutations to all other 19 amino acids. To compute ΔΔG values, each mutation was compared to WT using the following equation:

$$\Delta\Delta G_{Mut} = \Delta G_{Mut} - \Delta G_{WT}$$

where $\Delta G_{mut}$ is the energy computed for the mutation and $\Delta G_{WT}$ is the energy computed for the WT residue at the same position. All calculations were performed using default parameters unless otherwise specified.

Triad ΔΔG Calculation.

All Rosetta calculations were performed using a modified version of the rosetta energy function described by Rohl et al. and implemented within the protein design software Triad (2012, Protabit, LLC, Pasadena, Calif.). (Rohl et al. 2004, *Methods in Enzymol.*, Academic press, pp. 66-93, the entire contents of which are herein incorporated by reference. The version of rosetta implemented in Triad employs a softer Lennard-Jones potential, a different set of amino-acid reference energies, and modified hydrogen bond and amino acid propensity weights. The energy function also lacks terms unnecessary for point mutation calculations including those for disulfide bonding, Ramachandran, proline closure, and omega tethering. Designs were performed on chain A of the HjCel5a crystal structure (PDB ID 3QR3) (SEQ ID NO: 6) (Lee et al. 2011, supra). After removing water molecules and ions, hydrogens were added to the structure using the protein process application within the design software Triad. Triad was additionally employed to optimize the structure through 50 steps of gradient-based energy minimization using the rosetta forcefield.

Glycine Scan.

The glycine scan was performed in Triad using the modified version of the rosetta forcefield described in the Triad ΔΔG Calculation section (above). The scan mutates glycine in the native structure to each of the other 19 amino acids. All other conditions addressed in the rosetta calculation section apply to the glycine scan. The information calculated here is simply a subset of the data retrieved from the more comprehensive Triad-rosetta ΔΔG scan and is reformatted to facilitate data analysis.

Proline Scan.

The proline scans were performed with a restricted version of the algorithm used for the original Triad ΔΔG scan calculation. This scheme calculates ΔΔG values for mutating every position in the protein to proline and provides a ranked list of mutations. As in the glycine calculation, the generated information is a reformatted subset of the data retrieved from the Triad ΔΔG scan.

Disulfide Bond Engineering Calculations.

Disulfide bond engineering calculations were performed using the ssdesign application in the protein design software Triad. If two cysteine (CSS) rotamers come in close contact, the program adopts smaller values for force constants and barriers for DREIDING bonds, angles, and torsions. This leniency has been optimized to detect native disulfides as many disulfide geometries show slight deviations from canonical values. To design disulfides, the rotamer optimization algorithm simultaneously switches a pair of residues to CSS rotamers. Pair moves are biased towards those with good pairwise energies, i.e., those likely to form disulfides. Calculations were performed with 7 trajectories, a rotamer pair factor of 10, an iterations multiplier of 5, a disulfide force constant of 15, a disulfide max benefit of 35, and a CSS penalty of 15. All calculations employed a version of the rosetta forcefield, as described in the Triad ΔΔG Calculation section (above), modified to employ the DREIDING disulfide bonding energy terms. The term used for bonds within disulfides is:

$$E_{bond} = 12700.0 B_{1,2} (r_{1,2} - R^{1,2})^2$$

where B is the bond order (1, 1.5, 2, or 3), r is the Cartesian distance between atoms 1 and 2, and R is the equilibrium bond distance between atoms 1 and 2. The term for disulfide angles is as follows:

$$E_{angle}=12100.0(\angle_{1,2,3}-\theta_{1,2,3})^2$$

where $\angle_{1,2,3}$ is the observed angle between atoms 1, 2, and 3 and $\theta_{1,2,3}$ is the equilibrium angle. Disulfide torsion angles are defined as:

$$E_{torsion}=12K_{1,2,3,4}N(1-d_{1,2,3,4}\cos(n_{1,2,3,4}\chi_{1,2,3,4})$$

where $K_{1,2,3,4}$ is the energy barrier, N is the number of torsion terms where atoms 2 and 3 are placed in the center, $d_{1,2,3,4}$ is the phase factor (1 for cis, −1 for trans), $n_{1,2,3,4}$ is the periodicity, and $\chi_{1,2,3,4}$ is the torsion angle.

Additional disulfide bond engineering calculations were performed using the online server for Disulfide by Design version 2.11 (Dombkowski, 2003, *Bioinformatics*, 19:1852-1852, the entire contents of which are herein incorporated by reference.) Calculations were executed on both chains in the HjCel5a crystal structure (PDB ID 3QR3). Disulfide bonds principally contain four atoms linked in a linear fashion: $C_\beta$-$S_\gamma$-$S_\gamma$-$C_\beta$. In this calculation, a disulfide model is generated with fixed $C_\beta$-$S_\gamma$ (1.81 Å) and $S_\gamma$-$S_\gamma$ (2.04 Å) bond lengths and $C_\beta$-$S_\gamma$-$S_\gamma$ (104.15° bond angles. To initiate the calculation, a pair of residues is chosen. The $\chi 3$ torsion angle, formed through rotating the $C_\beta$ about the $S_\gamma$-$S_\gamma$ bond, is allowed to vary until the $C_\beta$-$C_\beta$ distance matches that observed in the crystal structure. Energies ($E_{ij}$) are then calculated using the following equations:

$$E_{ij}=E(\chi_{1,i})+E(\chi_{1,j})+E(\theta_i)+E(\theta_j) \quad (1)$$

$$E(\chi_1)=1.4[1+\cos(3\chi_1)] \quad (2)$$

$$E(\chi_3)=4.0[1-\cos(2_3+160)] \quad (3)$$

$$E(\theta)=55.0[\theta-\theta_0]^2 \quad (4)$$

Where i and j are residue positions, θ is the $C_\alpha$-$C_\beta$-$S_\gamma$ angle, and $\theta_0=114.6°$. Energies are computed in kcal mol$^{-1}$ with higher values corresponding to more favorable mutations. All calculations were performed with default settings.

Cel5a Plasmid Construction.

Double mutants for disulfide engineering were constructed using a modified version of the Quikchange method in which two primer pairs are added to a single reaction. Additional details are as described in Example 1.

Thermostability/Activity Screen.

Thermostability and activity screens were performed as described in Example 1.

Enzyme Purification.

Cel5a proteins were cultured and purified as described in Example 1.

Park-Johnson Assay.

The Park-Johnson assay was performed as described in Example 1.

$T_{50}$ Assay.

The $T_{50}$ assay was performed as described in Example 1.

Single-Point Activity Assay.

The single-point activity assay was performed as described in Example 1.

Example 4

Identification of G189A, F191V, G239D, T233V, S242A, V265T, D271Y, S318P, and S322a, with Mutant Residue Numbering Based on SEQ ID NO: 6

Using a SCHEMA algorithm, a Cel5a chimera library was designed. *Hypocrea jecorina* Cel5a was recombined with three homologues from thermophilic fungi (*Phialophora* sp. G5, *Penicillium decumbens, Penicillium pinophilum*).

Out of this Cel5a chimera library, 25 chimeras were synthesized, appending to the N-terminus of each the cellulose binding module (CBM) form *H. jecorina* Cel5a, as well as a C-terminal His6 tag for purification. The chimeras were expressed in *Saccharomyces cerevisiae* and purified using column chromatography. It was observed that 23 out of the 25 chimeras were catalytically active, and the thermostabilities were measured by finding the temperature at which the enzymes loses half of its activity relative to that at its optimum temperature over a 2 hour (h) reaction period ("$T_{A50}$"). The $T_{A50}$'s for all of the functional chimeras was measured on crystalline cellulose (Avicel). The test set exhibits a range of thermostability values from which a regression model was built.

Regression Modeling Predicts a Highly Stable Chimera.

The revised linear regression model predicts that only two blocks are stabilizing relative to HjCel5a: blocks 6 and 7 from PgCel5a (+1.0° C. and +3.3° C., respectively). Combining these two blocks created chimera 110, which is 4.3° C. more stable and 18 mutations away from its closest parent, HjCel5a. Since chimera blocks may contain both stabilizing and destabilizing point mutations, each of the 18 single amino acid mutations were introduced into these blocks in HjCel5a individually and the thermostabilities of the mutant enzymes were tested.

Figure 17:
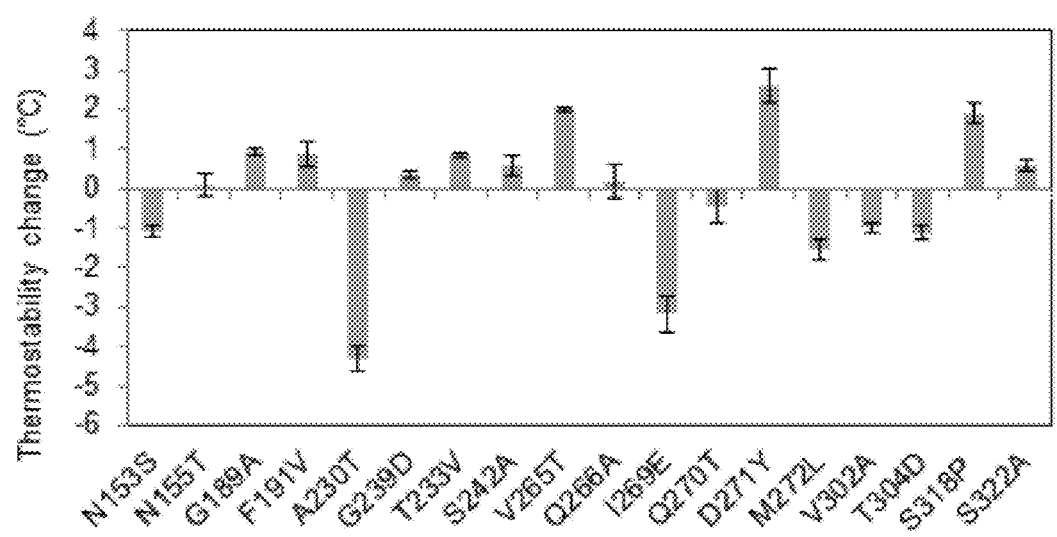
FIG. 17 is a graph showing the A thermostability (compared to wild type Cel5a) of the indicated Cel5a point mutants (with mutant residue numbering based on SEQ ID NO: 6), according to embodiments of the present invention.
Figure 18A:
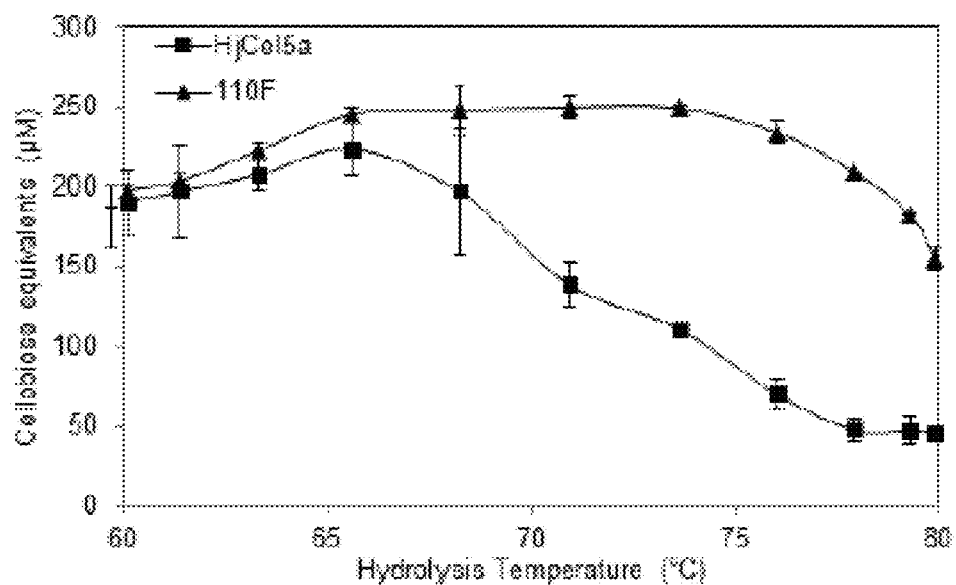
FIG. 18A is a graph showing the amount of cellulase activity versus hydrolysis temperature for WT (HjCel5a) (squares) and 110F Cel5a combination mutant (triangles) (with mutant residue numbering based on SEQ ID NO: 6), as described herein, according to embodiments of the present invention.

As shown in FIG. 17, nine of the eighteen mutations were stabilizing, and seven were destabilizing, while two had no effect. The nine stabilizing HjCel5a point mutations include G189A, F191V, G239D, T233V, S242A, V265T, D271Y, S318P, and S322A, with mutant residue numbering based on SEQ ID NO: 6. Subsequently all of the stabilizing mutations (save for T233V, which compromised activity slightly) were combined to create chimera 110F. This chimera had a stability increase (as measured by $T_{A50}$) of 10.1° C. relative to HjCel5a (FIG. 18A). Its optimal temperature was also increased by ~10° C., and its activity was not compromised by thermostabilization.

Figure 18B:
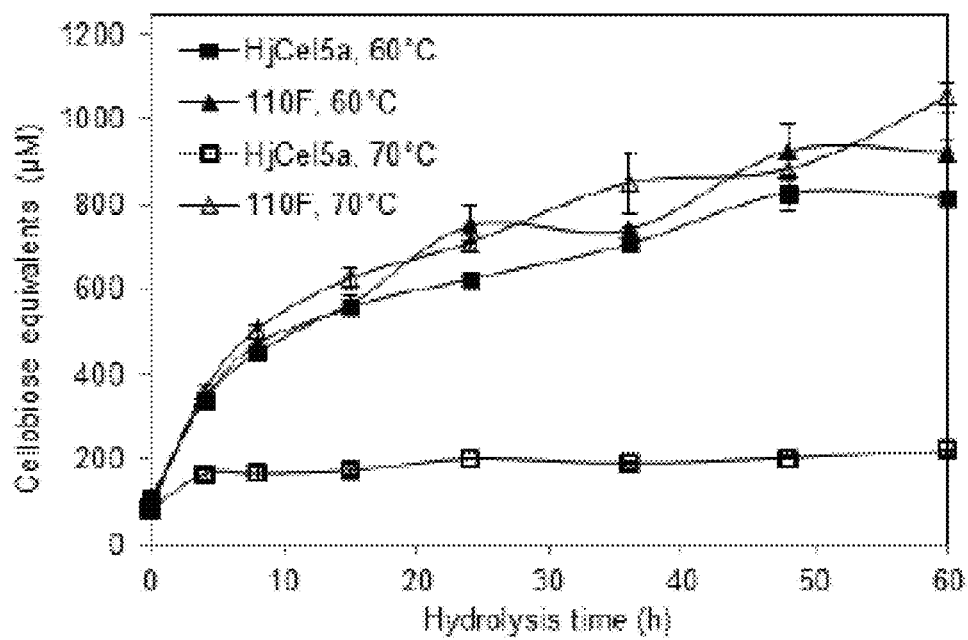
FIG. 18B is a graph showing the amount of cellulase activity over 60 hours for WT (HjCel5a)(squares) and 110F Cel5a combination mutant (triangles) (with mutant residue numbering based on SEQ ID NO: 6) at 60° C. and 70° C. as indicated, according to embodiments of the present invention.

To evaluate the improvement of 110F over industrially relevant time scales, its activity was compared to that of HjCel5a over 60 h hydrolyses at 60° C. and 70° C. As shown in FIG. 18B, 110F displays more activity at both temperatures, and it remains highly active at 70° C. over a 60 h period, whereas wild-type HjCel5a is nearly inactive at 70° C.

Cel5a Plasmid Construction.

Genes encoding *Hypocrea jecorina* Cel5a, *Phialophora* sp. G5 Cel5a, *Penicillium decumbens* Cel5a, and *Penicillium pinophilum* Cel5a were synthesized with *S. cerevisiae* codon bias (DNA 2.0, Menlo Park, Calif.), and cloned into the yeast secretion vector YEp352/PGK91-1-αss as described previously by Komor et al. 2012, supra and Wu et al. 2013, *Biotech. and Bioeng.*, 110:1874-1883, the entire contents of both of which are herein incorporated by reference. Each gene had a C-terminal linker and carbohydrate binding module from *H. jecorina* Cel5a.

SCHEMA Guided Structure-Based Recombination.

Gene sequences of *Hypocrea jecorina* Cel5a, *Phialophora* sp. G5 Cel5a, *Penicillium decumbens* Cel5a, and *Penicillium pinophilum* Cel5a were aligned using the MUSCLE multiple sequence alignment software, as described by Edgar, 2004, *Nucleic acids research*, 32:1792-1797, the entire contents of which are herein incorporated by reference. The structure of the catalytic domain of *H. jecorina* Cel5a (PDB structure 3QR3 chain A) (SEQ ID NO: 6) was used to build a map of amino acid contacts. (Lee et al., 2011, *Protein Science*, 20:1935-1940, the entire contents of which are herein incorporated by reference. A contact is defined as two amino acids having at least one non-hydrogen atom within 4.5 Å of each other. Libraries that minimized the average number of disrupted SCHEMA contacts in the resulting chimeras were designed using graph partitioning as described in Smith et al. 2013, *ACS Synthetic Biology, Jun.* 3, 2013, PMID: 23688124, the entire contents of which are herein incorporated by reference. A library design was chosen with an average SCHEMA energy (number of disrupted contacts) of 12.1 and an average of 55.4 amino acid mutations from the closest parent. The C-terminal linker and carbohydrate binding module from *H. jecorina* Cel5a was appended to each chimera.

Optimal Experimental Design.

The Submodular Function Optimization Matlab toolbox (Ye et al., *J. Comput. Biol.*, 14: 777-790, the entire contents of which are herein incorporated by reference) was used to choose chimeras that had both low SCHEMA disruption and maximal mutual information between the sampled chimeras and the rest of the library, as described in Romero et al. 2012, *ACS Synthetic Biology*, 1:221-228, the entire contents of which are herein incorporated by reference.

Chimera Library Construction.

Chimeras were constructed from 500 bp DNA fragments via overlap extension PCR, as described previously in Georgescu et al. 2003, Saturation mutagenesis: In *Directed evolution library creation*, pp. 75-83, Springer. The DNA fragments ("gBlocks") were synthesized by Integrated DNA Technologies (San Jose, Calif.). Codons were optimized for yeast expression using Gene Designer software from DNA 2.0 (Menlo Park, Calif.) (Villalobos et al. 2006, *BMC Bioinformatics*, 7:285, the entire contents of which are herein incorporated by reference.) Genes were cloned into the YEp352/PGK91-1-ass vector using Gibson assembly as described by Gibson 2011, *Methods Enzymology*, 498: 349-361, the entire contents of which are herein incorporated by reference.

Enzyme Purification.

YEp352/PGK91-1-ass vectors containing Cel5a chimeras were transformed into the BY4742 Δkre2 strain of yeast (BY4742; Mat a; his3D1; leu2D0; lys2D0; ura3D0; YDR483w::kanMX4) obtained from EUROSCARF (Frankfurt, Germany). Yeast colonies expressing Cel5a with C-terminal His$_6$ tag were grown at 30° C.: first overnight in 5 mL synthetic dextrose-uracil (SD-Ura) medium, then expanded into 50 mL SD-Ura (+50 µg/mL kanamycin) medium for 24 h, and then expanded into 1 L YPD (+50 µg/mL kanamycin) medium for an additional 48 h. Cultures were centrifuged at 4500×g for 20 min and the supernatant was filtered with 0.2 µm PES (polyethersulfone) filter unit from Nalgene (VWR, Radnor, Pa.). Protein was loaded onto 5 mL HisTrap columns and purified using an ÄKTAxpress chromatography system (GE Healthcare, Pittsburgh, Pa.). Purified cellulases were buffered-exchanged to 50 mM sodium acetate buffer pH 5.0 using Vivaspin 20 ultrafiltration spin tubes (GE Healthcare, Pittsburgh, Pa.). Protein concentrations were determined using A280, with theoretical extinction coefficients found using ProtParam on the ExPASy server as described in Gasteiger et al. 2005, *The Proteomics Protocols Handbook*, pp. 571-607, Springer, the entire contents of which are herein incorporated by reference.

$T_{A50}$ Thermostability Measurements.

100 µL samples in 50 mM sodium acetate buffer, pH 5.0 containing 0.2 µM Cel5a and 1% (w/v) Avicel were incubated at a range of temperatures for 2 h. A modified Park-Johnson reducing sugar assay was used to measure activity. (Park and Johnson, 1949, *J. Biol. Chem.*, 181: 149-151, the entire contents of which are herein incorporated by reference.) In brief, reaction mixtures were spun at 1000 g for 5 min to remove Avicel. 50 µL of supernatant was removed and transferred to a mixture of 100 µL ferricyanide reagent (0.5 g/L $K_3Fe(CN)_6$, 34.84 g/L $K_2HPO_4$, pH 10.6) and 50 µL carbonate-cyanide reagent (5.3 g/L $Na_2CO_3$, 0.65 g/L KCN). The reaction was heated at 95° C. for 15 min in an Eppendorf Mastercycler, and then cooled on ice for 5 min. 180 µL of the reaction was removed and mixed with 90 µL ferric iron solution (2.5 g/L $FeCl_3$, 10 g/L polyvinyl pyrrolidone, 2 N $H_2SO_4$). After 2 min, absorbance at 595 nm was taken, using solutions of 0 µM to 300 µM cellobiose as standards.

$T_{A50}$ was determined by plotting activities against the temperature using Matlab (Mathworks, Natick, Mass., supra) and fitted using 4-parameter sigmoidal curves. The $T_{A50}$ value is the temperature at which enzyme activity is halfway between optimal activity and no activity. Reported values were averaged from at least two independent measurements.

Cellulase Activity Measurements.

All cellulase activity measurements were conducted in 50 mM sodium acetate buffer, pH 5.0. To determine activity-temperature profiles of Cel5a, samples containing 0.2 µM of purified Cel5a and 1% (w/v) Avicel were incubated at 60 and 70° C. for 60 h. After hydrolysis, the reaction supernatants were sampled for reducing sugar concentrations via Nelson-Somogyi assay, using cellobiose as the reducing sugar standard as described in Somogyi, 1952, *J. Biol. Chem.*, 195: 19-23 and Nelson, 1944, *J. Biol. Chem.*, 153: 375-379, the entire contents of both of which are herein incorporated by reference. In brief: 50 µL of reaction solution was added to 40 µL carbonate-tartrate solution (144 g/L $Na_2SO_4$, 12 g/L potassium tartrate tetrahydrate, 24 g/L $Na_2CO_3$, 16 g/L $NaHCO_3$) and 10 µL copper solution (180 g/L $Na_2SO_4$, 20 g/L $CuSO_4 \cdot 5H_2O$) and heated to 95° C. for 15 min in an Eppendorf Mastercycler. The reaction was placed on ice for 5 min and then mixed with 50 µL arsenomolybdate solution (50 g/L $(NH_4)_2MoO_4$, 1.5 N $H_2SO_4$, 6 g/L $NaH_2AsO_4$). After mixing, absorbance at 520 nm was read, using 0 to 2 mM cellobiose solutions as standards.

Example 5

Combination Cel5a Mutants

First Generation Combination Cel5a Endoglucanase Mutants.

Using the information from Examples 1-4, a series of combination constructs were synthesized containing highly stabilizing mutations. Mutations demonstrating a $\Delta T_{50} \geq 0.5°$ C. were selected for incorporation. If several stabilizing mutations appeared in the same region within the HjCel5a structure, the mutations with the highest $\Delta T_{50}$ values were generally retained. In ambiguous situations where interaction between two sites could not clearly be ascertained, several alternative constructs were tested. A chosen set included 13 possible mutations: T57N, N76P, T80E, S139P, N155E, G189S, K219Q, G239N, D271F, Y278F, G293A, S309F, and S318P, with mutant residue numbering based on SEQ ID NO: 6.

Figure 19A:
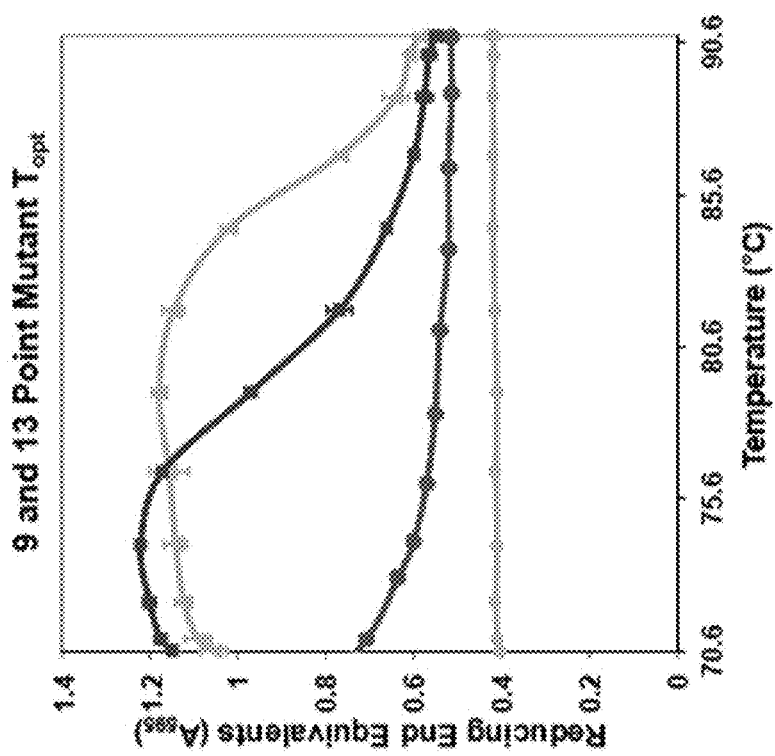
FIG. 19A is a graph of thermostability and activity in wild type (WT) and the indicated Cel5a combination mutant proteins (with mutant residue numbering based on SEQ ID NO: 6) following a reducing end (Park-Johnson) assay as described herein, with bovine serum albumin (BSA) used as a control, according to embodiments of the present invention.

These mutations were incrementally added to the WT sequence with the least and most mutated constructs containing 1 and 13 mutations, respectively (Table V), with mutant residue numbering based on SEQ ID NO: 6. Following cloning, mutants were tested for activity with the same screen employed to detect point mutations (FIG. 19A). All of the constructs showed improvements in activity over WT.

TABLE V

Composition of Combination Constructs

| Construct | # of Mutations | T57N | N76P | T80E | S139P | N155E | G189S | K219Q | G239N | D271F | Y278F | G293A | S309F | S318P |
|---|---|---|---|---|---|---|---|---|---|---|---|---|---|---|
| 1 | 1 | | | x | | | | | | | | | | |
| 2 | 1 | | | | x | | | | | | | | | |
| 3 | 1 | | | | | x | | | | | | | | |
| 4 | 2 | | x | | x | | | | | | | | | |
| 5 | 4 | x | x | | x | x | | | | | | | | |
| 6 | 5 | x | x | | x | x | x | | | | | | | |
| 7 | 5 | x | x | | x | x | | x | | | | | | |
| 8 | 5 | x | x | | x | x | | | x | | | | | |
| 9 | 5 | x | x | | x | x | | | | x | | | | |
| 10 | 6 | x | x | | x | x | | | | x | x | | | |
| 11 | 6 | x | x | | x | x | x | x | | | | | | |
| 12 | 6 | x | x | | x | x | x | | x | | | | | |
| 13 | 6 | x | x | | x | x | | x | x | | | | | |
| 14 | 7 | x | x | | x | x | x | | | x | x | | | |
| 15 | 8 | x | x | | x | x | x | | | x | x | x | | |
| 16 | 9 | x | x | x | x | x | x | | | x | x | x | | |
| 17 | 10 | x | x | | x | x | x | x | x | x | x | x | | |
| 18 | 11 | x | x | x | x | x | x | x | x | x | x | x | | |
| 19 | 12 | x | x | x | x | x | x | x | x | x | x | x | | x |
| 20 | 13 | x | x | x | x | x | x | x | x | x | x | x | x | x |

| Construct | # of Mutations | T57N | T80E | N155E | G189S | G239E | D271Y | G293A | S309L/W | S318E/P | S79P | V101I | S133R | E53D |
|---|---|---|---|---|---|---|---|---|---|---|---|---|---|---|
| s13pt1 | 13 | x | x | x | x | x | x | x | x(L) | x(P) | x | x | x | x |
| s13pt2 | 13 | x | x | x | x | x | x | x | x(W) | x(P) | x | x | x | x |
| s13pt3 | 13 | x | x | x | x | x | x | x | x(L) | x(E) | x | x | x | x |
| s13pt4 | 13 | x | x | x | x | x | x | x | x(W) | x(E) | x | x | x | x |

Figure 19B:
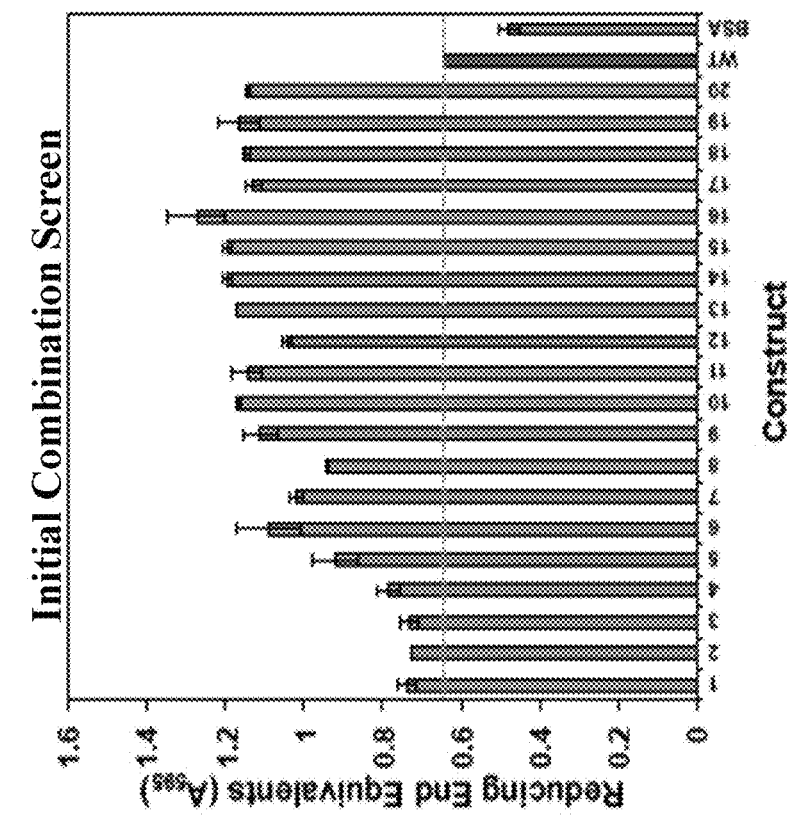
FIG. 19B is a graph of the reducing ends equivalents (Park-Johnson assay) for Cel5a WT (green circles), 9-point mutant (blue squares), and 13-point mutant (yellow squares) proteins (with mutant residue numbering based on SEQ ID NO: 6) over a range of temperatures as indicated, according to embodiments of the present invention.
Figure 19D:
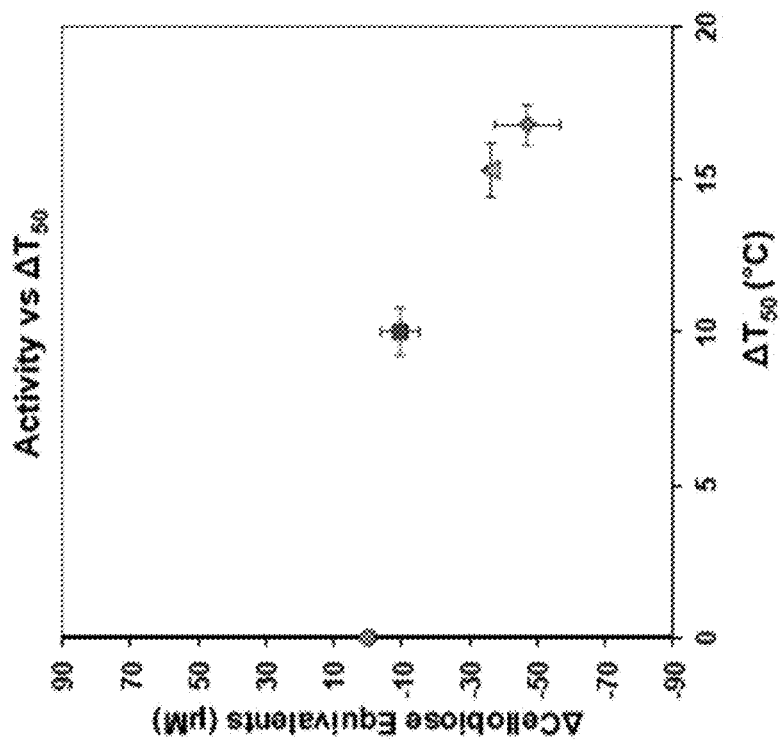
FIG. 19D is a graph showing the A cellulase activity (compared to wild type Cel5a) of the indicated 9-point mutant (with mutant residue numbering based on SEQ ID NO: 6) versus the $\Delta T_{50}$ (compared to wild type Cel5a) at 60° C. from a single point assay as described herein, according to embodiments of the present invention.
Figure 19C:
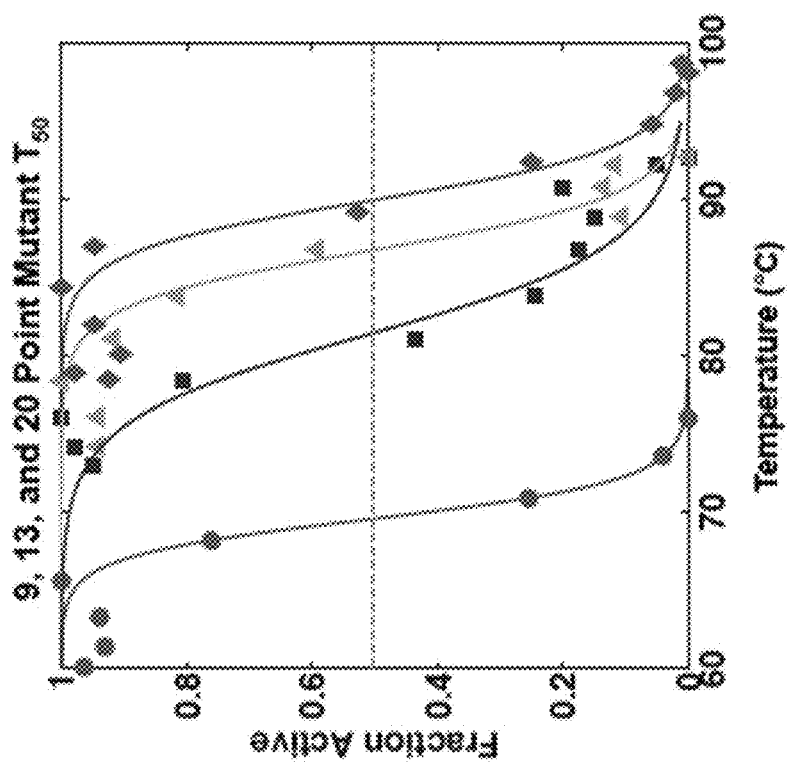
FIG. 19C is a $T_{50}$ plot for the 9-, 13-, and 20-point mutants of FIG. 19A, where the fraction active reflects the amount of the total protein that is active after a 10 minute heat treatment from 60-100° C., where WT (green circles), 9-point mutant (blue squares), 13-point mutant (yellow squares), and 20-point mutant (purple diamonds) are shown, according to embodiments of the present invention.

Two constructs predicted to have either high activity or thermostability were chosen for further characterization. With nine mutations (T57N, N76P, T80E, S139P, N155E, G189S, D271F, Y278F, and G293A) with mutant residue numbering based on SEQ ID NO: 6, construct 16 demonstrated the greatest performance on the activity screen. Construct 20 contains all 13 possible mutations and was projected to demonstrate the greatest thermostability. These two combination mutants were expressed, purified and tested to assess their hydrolytic capabilities on Avicel over a gradient of temperatures (FIG. 19B), obtain their $T_{50}$ values (FIG. 19C), and determine their activity at 60° C. after 2 hours (FIG. 19D). Table VI provides a summary of these results. The 9-point mutant (construct 16 of Table V) shows a 10° C. increase in both the optimal operating temperature ($T_{opt}$) and in $T_{50}$ relative to WT. As expected, the 13-point mutant demonstrates even greater improvement in thermostability with a 16° C. increase in $T_{opt}$ and a 14° C. increase in $T_{50}$ relative to WT. These increases, however, were accompanied by decreases in activity of 4% for the 9-point mutant and 17% for the 13-point mutant. FAnalysis revealed that the 13-point mutant contains more mutations that are known from previous experiments to decrease activity than the 9-point mutant. As such, the drop in activity likely originates from the collective effects of point mutations rather than incompatibilities between the mutations.

TABLE VI

Characterization of Combination Mutants

| Construct | # of Mutations | $T_{50,mut}$ (° C.) | $\Delta T_{50}$ (° C.) | $T_{opt}$ (° C.) | Activity (μM Cellobiose Equivalents) | ΔActivity (μM Cellobiose Equivalents) | Expression Level Relative to WT |
|---|---|---|---|---|---|---|---|
| WT | 0 | 69.6 ± 1.0 | — | 64 | 216.7 ± 10.6 | — | — |
| 9 pt | 9 | 81.5 ± 0.4 | 10.0 ± 0.8 | 74 | 184.2 ± 5.7 | −9.6 | 3.5 |
| 13 pt | 13 | 86.8 ± 0.6 | 13.8 ± 0.9 | 80 | 157.4 ± 1.4 | −36.3 | 4.1 |
| 20 pt | 20 | 90.0 ± 0.1 | 16.8 ± 0.7 | 82 | 146.6 ± 9.8 | −47.1 | 2.7 |
| s13pt1 | 13 | 85.3 ± 0.2 | 14.9 ± 0.7 | 78 | 192.7 ± 6.9 | −1.0 | 4.1 |
| s13pt2 | 13 | 85.6 ± 0.4 | 15.4 ± 0.7 | 78 | 221.1 ± 5.9 | 27.4 | 4.1 |
| s13pt3 | 13 | 83.0 ± 0.4 | 12.0 ± 0.8 | 75 | 231.2 ± 5.6 | 37.5 | 5.9 |
| s13pt4 | 13 | 83.9 ± 0.2 | 12.2 ± 0.7 | 75 | 262.6 ± 11.5 | 68.8 | 3.7 |

To ascertain whether additional mutagenesis could counter these activity decreases, a 20-point mutant was constructed containing mutations with $\Delta T_{50} \geq 0°$ C. This combination mutant contains all 13 of the previously incorporated mutations plus T18P, G64A, S79P, V101I, S133R, D13E, and E53D. Individually, many of the less stabilizing mutations show improvements in activity; summing the changes in activity measured for these point mutations gives a net activity increase of 20.7 μM cellobiose equivalents. As such, that possibility that these less stabilizing mutations might boost thermostability while rescuing activity was tested. While the 20-point mutant shows a $\Delta T_{50}$ of 16.8° C. (FIG. 19C), its activity at 60° C. decreases even further to 47.1 μM cellobiose equivalents below WT (22% of WT activity) (FIG. 19D). This result suggests that activity losses from individual mutations permanently accumulate and cannot be rescued by adding mutations that improve activity in isolation.

Figure 19F:
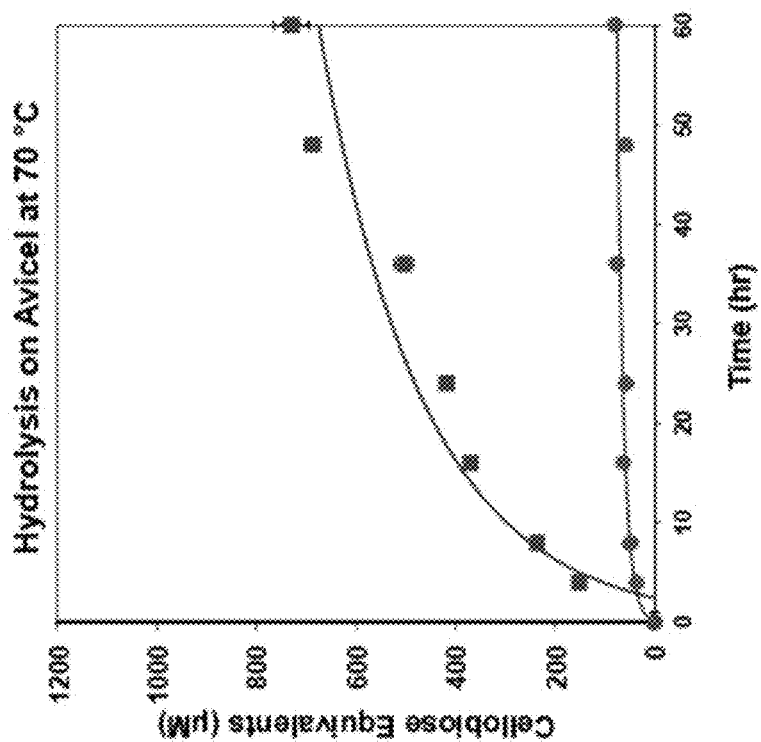
FIG. 19F is a graph showing the amount of cellulase activity of WT (green circles) and the indicated 9-point mutant (blue circles) (with mutant residue numbering based on SEQ ID NO: 6) at 70° C., according to embodiments of the present invention.
Figure 19E:
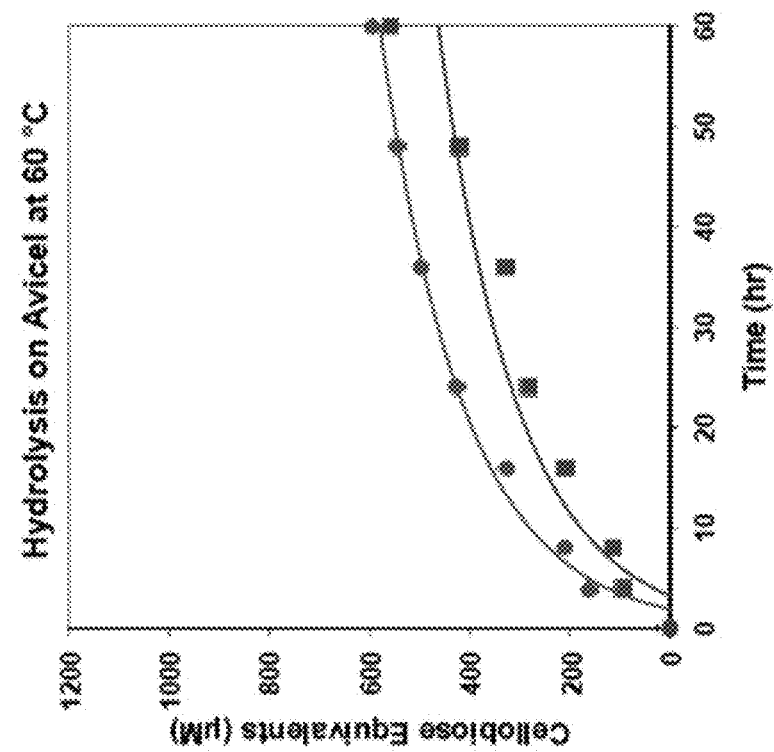
FIG. 19E is a graph showing the amount of cellulase activity of WT (green circles) and the indicated 9-point mutant (blue circles) (with mutant residue numbering based on SEQ ID NO: 6) at 60° C., according to embodiments of the present invention.

Although these initial combination mutants exhibit diminished activity, it was hypothesized that their enhanced thermostability might improve performance in longer assays. Due to its relatively modest decrease in activity, the 9-point mutant (construct 16 of Table V) was chosen for 60-hour activity tests on Avicel at 60 and 70° C. (FIGS. 19E, 19F). This construct demonstrates a nine-fold activity improvement over WT at the elevated temperature. When compared to WT hydrolysis at 60° C., the total product yield improves by about 134 µM of cellobiose equivalents (24% increase, 1.2 fold improvement).

Second Generation Combination Cel5a Endoglucanase Mutants.

Using the 9-point mutant as a template, a second-generation of combination mutants was constructed by excluding all mutations detrimentally affecting activity. The process involved reverting mutations N76P, S139P, K219Q, G239N, D271F, Y278F, and S309F back to the WT residue or, if available, a less stable, more active alternate. Mutations appearing in the four final second generation 13-point combination mutants (s13pt 1-4) are summarized in Table V, with mutant residue numbering based on SEQ ID NO: 6.

Figure 20A:
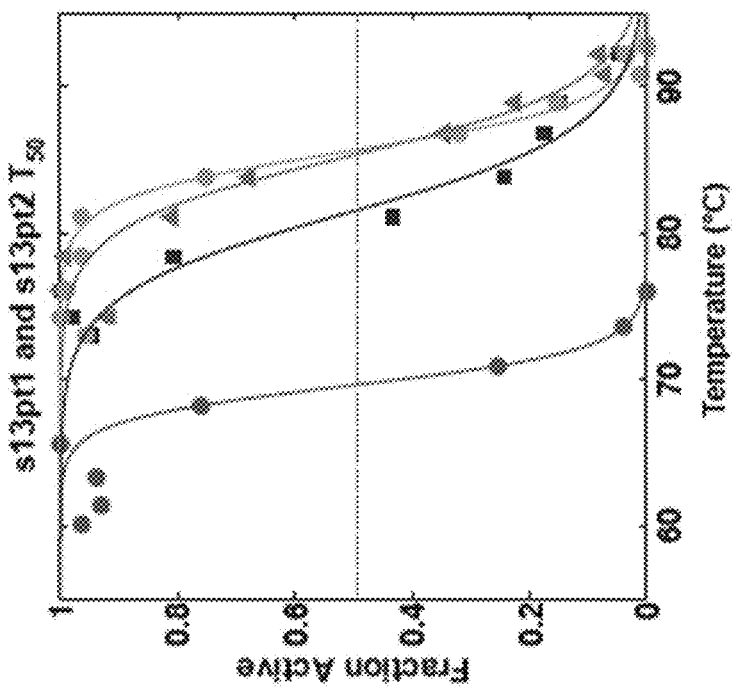
FIG. 20A is a $T_{50}$ plot for the s13pt1 and s13pt2 combination mutants, where the fraction active reflects the amount of the total protein that is active after a 10 minute heat treatment from 60-100° C., where WT (green circles), 9-point mutant (blue squares), s18pt1 mutant (red triangles), and s13pt2 mutant (yellow circles) are shown (with mutant residue numbering based on SEQ ID NO: 6), according to embodiments of the present invention.
Figure 20B:
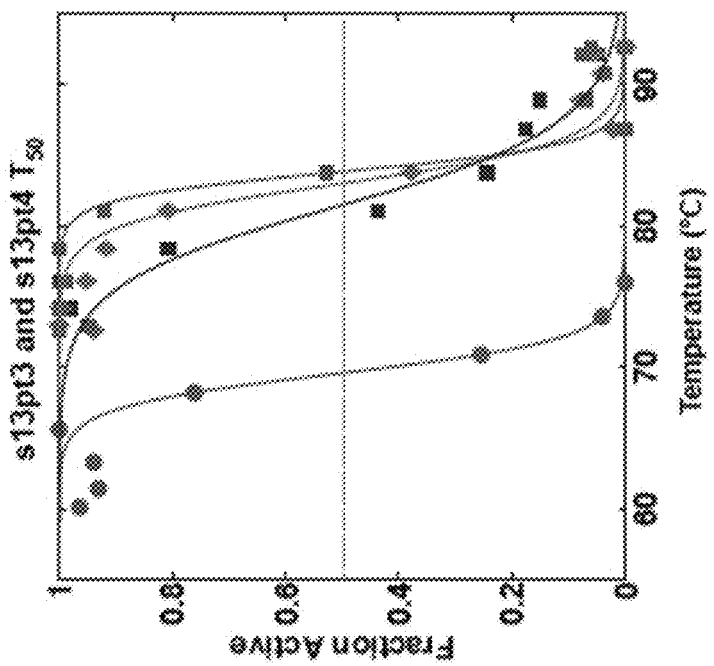
FIG. 20B is a $T_{50}$ plot for the s13pt3 and s13pt4 combination mutants, where the fraction active reflects the amount of the total protein that is active after a 10 minute heat treatment from 60-100° C., where WT (green circles), 9-point mutant (blue squares), s18pt3 mutant (turquoise diamonds), and s13pt4 mutant (purple squares) are shown, according to embodiments of the present invention.
Figures 20C, 20D:
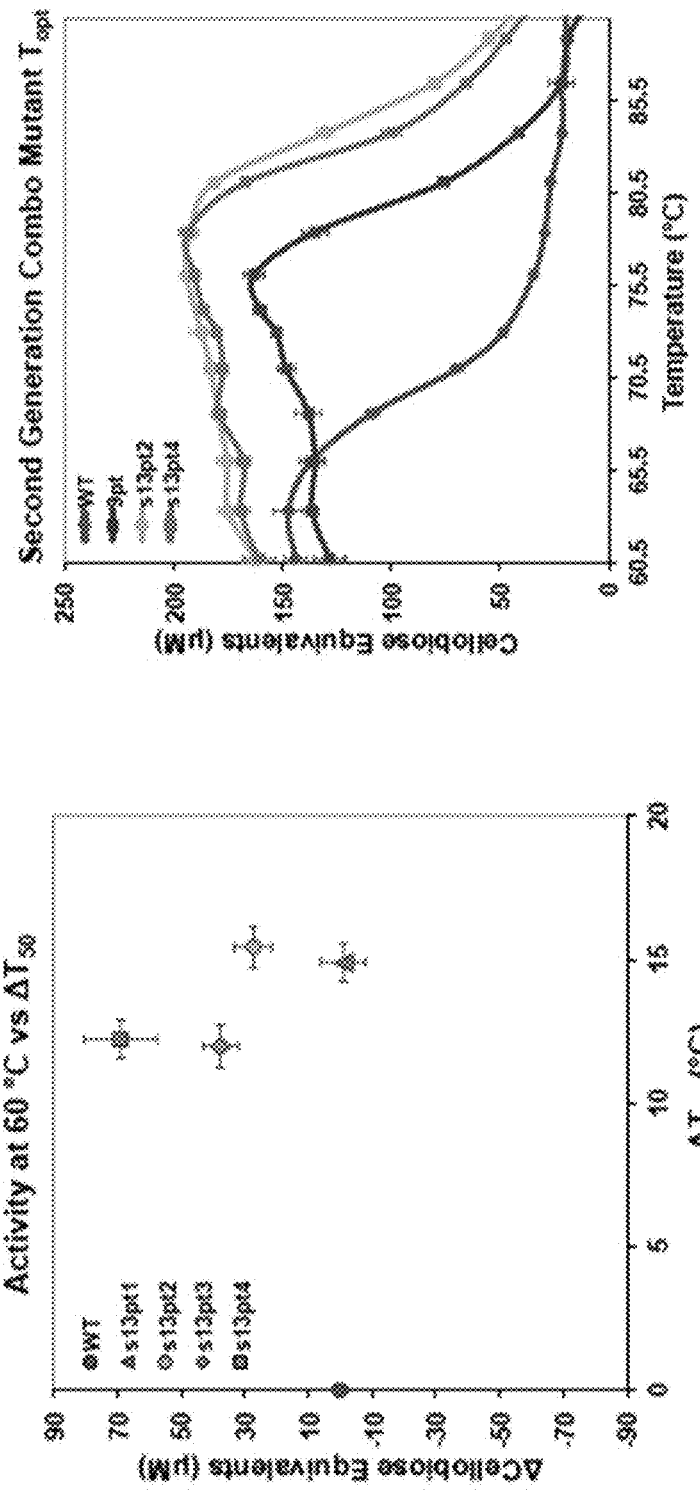
FIG. 20C is a graph showing the A cellulase activity (compared to wild type Cel5a) of the indicated combination mutant (with mutant residue numbering based on SEQ ID NO: 6) versus the $\Delta T_{50}$ (compared to wild type Cel5a) at 60° C. from FIGS. 20A, 20B, according to embodiments of the present invention.
FIG. 20D is a graph showing the amount of cellulase activity versus hydrolysis temperature for WT (green circles), s13pt2 mutant (yellow circles), and s13pt4 mutant (purple squares) (with mutant residue numbering based on SEQ ID NO: 6) as described herein, according to embodiments of the present invention.

The second-generation combination mutants performed as well or better than WT on all tested metrics. All four constructs show enhancements in thermostability with s13pt2 demonstrating the highest increase ($\Delta T_{50}$=15.4° C.) (Table VI, FIGS. 20A, 20B, 20C, 20D). Activity at 60° C. improved over WT for all constructs except s13pt1 (FIG. 20C). In this case, activity declined slightly by 1.0 µM of cellobiose. The combination mutants exhibit dramatic improvements in $T_{opt}$. In a two-hour activity test, s13pt1/2 and s13pt3/4 optimally function at 78 ($\Delta T_{opt}$=14° C.) and 75 degrees ($\Delta T_{opt}$=11° C.), respectively. Additionally, all of the mutants show ~4-6 fold increases in expression level over WT.

Figure 21A:
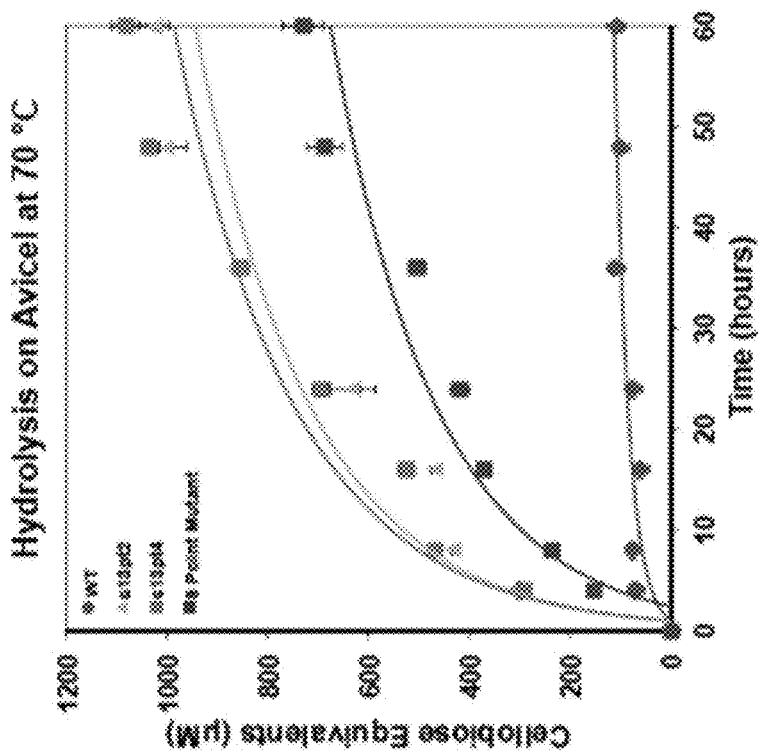
FIG. 21A is a graph showing the amount of cellulase activity over 60 hours for WT (green circles), 9-point mutant (blue squares), s13pt2 mutant (yellow circles), and s13pt4 mutant (purple squares) (with mutant residue numbering based on SEQ ID NO: 6) at 60° C., according to embodiments of the present invention.
Figure 21B:
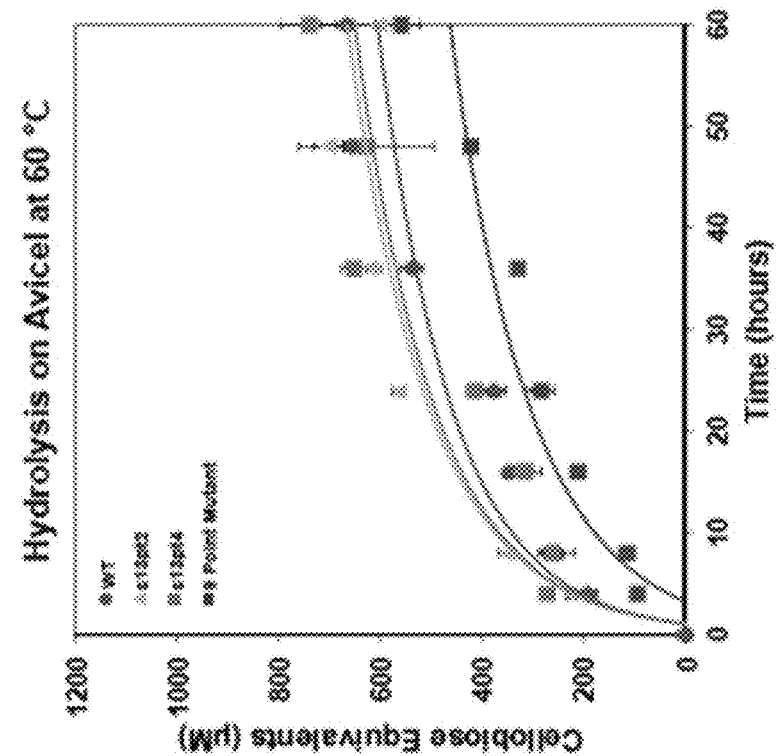
FIG. 21B is a graph showing the amount of cellulase activity over 60 hours for WT (green circles), 9-point mutant (blue squares), s13pt2 mutant (yellow circles), and s13pt4 mutant (purple squares) (with mutant residue numbering based on SEQ ID NO: 6) at 70° C., according to embodiments of the present invention.

To approximate industrial reactions, 60-hour hydrolysis experiments were conducted on the constructs with the highest activity (s13pt4) and thermostability (s13pt2). At 60° C., both combination mutants performed similarly to WT (FIG. 21A). This improvement dramatically increased at 70° C. (FIG. 21B). Compared to the WT performance at the same temperature, s13pt4 and s13pt2 exhibit ~9.5-10 fold increases in activity. Moreover, the combination mutants improve yield by 358-414 µM cellobiose equivalents (~60% increase) over the maximal amount possible using the WT enzyme.

Figure 21C:
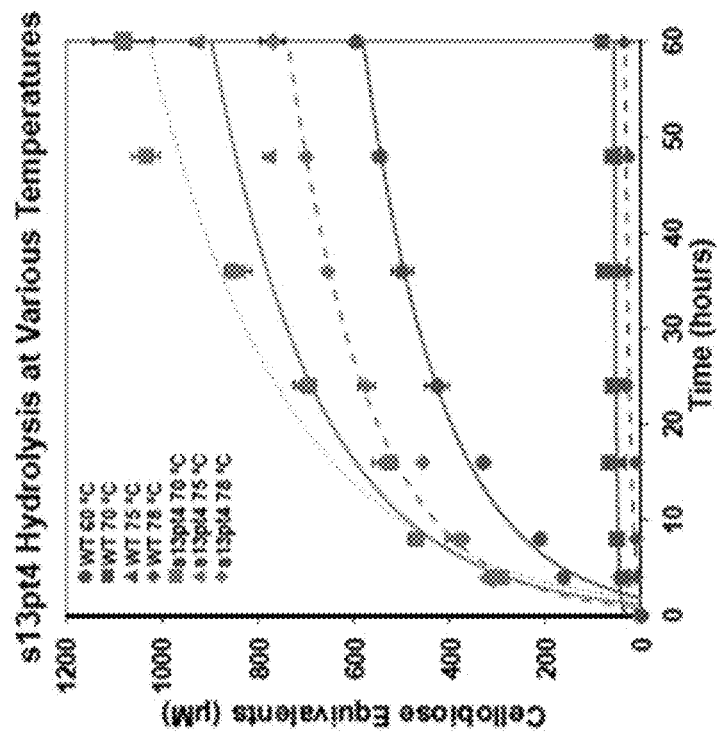
FIG. 21C is a graph showing the amount of cellulase activity over 60 hours for WT (green circles) and s13pt2 mutant (yellow circles) (with mutant residue numbering based on SEQ ID NO: 6) at 60° C. and/or 70° C., 75° C., and 78° C. as indicated, according to embodiments of the present invention.
Figure 21D:
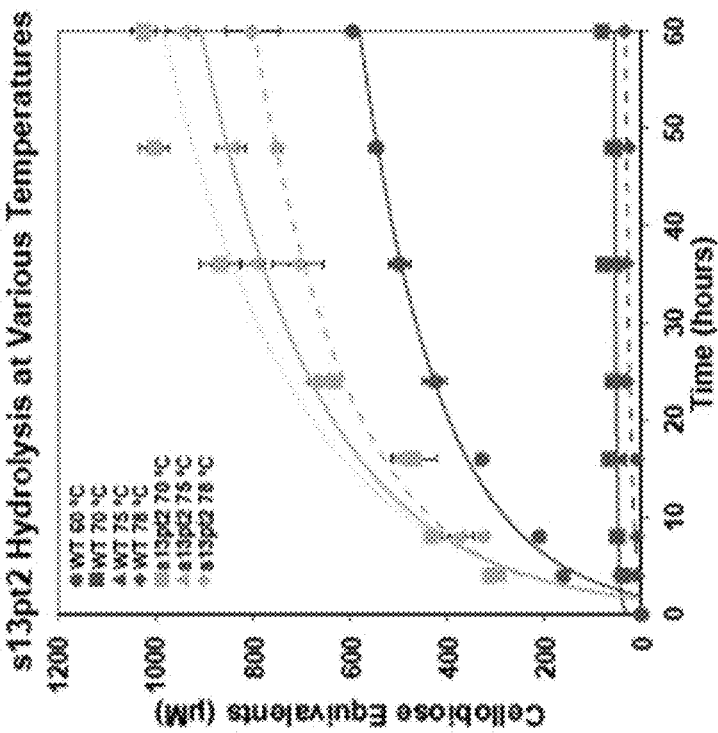
FIG. 21D is a graph showing the amount of cellulase activity over 60 hours for WT (green circles) and s13pt4 mutant (purple squares) (with mutant residue numbering based on SEQ ID NO: 6) at 60° C. and/or 70° C., 75° C., and 78° C. as indicated, according to embodiments of the present invention.

As shown, these combination mutants optimally perform at 75-78° C. in the 2-hour hydrolysis experiments. A long-term hydrolysis was tested to see if these mutant enzymes improved at higher temperatures. However, after 60-hours of hydrolysis, less activity was observed at 75 and 78° C. than at 70° C. (FIGS. 21C, 21D).

Cel5a Plasmid Construction.

Cel5a mutants were constructed as described in Example 1.

Thermostability/Activity Screen.

Thermostability and activity screens were performed as described in Example 1.

The Park-Johnson Assay was performed as described in Example 1.

Enzyme Purification.

Cel5a proteins were cultured and purified as described in Example 1.

$T_{50}$ Assay was performed as described in Example 1.

$T_{opt}$ Assay. Determination of the temperature yielding the maximum activity proceeded through incubating enzyme with Avicel for two hours at a gradient of temperatures, then determining sugar release with the Park-Johnson assay. In a 96-well PCR plate, 40 µL of purified enzyme were combined with 60 µL of 1.5% Avicel suspended in cellulase buffer (100 mL 50 mM sodium acetate, pH 5.0). Samples were incubated for 2 hours across a 20° C. gradient centered around a temperature projected to capture the peak of activity based on $T_{50}$ values. Activity was assessed from 25 µL of supernatant using the Park-Johnson assay.

Single-Point Activity Assay was performed as described in Example 1.

60-Hour Activity Assay.

To assess activity over a constant temperature for 60 hours, enzyme and substrate mixtures were combined in individual PCR tubes and frozen to arrest hydrolysis. In each tube, 40 µL of purified enzyme at a concentration of 0.5 µM was combined with 60 µL of 1.67% Avicel suspended in cellulase buffer (100 mL 50 mM sodium acetate, pH 5.0). Incubation occurred in a PCR block preheated before adding samples to prevent background activity. Time points were collected at 0, 4, 8, 16, 24, 36, 48, and 60 hours. Following hydrolysis, the reactions were thawed and moved to a 96-well plate to facilitate centrifugation. Supernatants were robotically collected. Cellobiose standards containing 0.0, 166.6, 333.3, 500.0, 833.3, 1000.0, 1500.0, and 2000.0 µM of cellobiose and 50 µL of the reaction supernatants were assessed for reducing sugar concentrations via the Nelson-Somogyi assay as described in Smogyi, 1952, *J. Biol. Chem.*, 195: 19-23 and Nelson, 1944, *J. Biol. Chem.*, 153: 375-379, the entire contents of both of which are herein incorporated by reference. All experiments were performed in triplicate.

Example 6

A Thermostable Cel5a Endoglucanase

Out of the point mutations identified in Examples 1-4, sixteen thermostabilizing mutations that did not compromise activity measured at 60° C. were combined into a single variant. If two suitable mutations occupied the same site, the more thermostabilizing of the two was selected. This combination HjCel5a mutant was termed: OptCel5a, which includes: T57N, E53D, S79P, T80E, V101I, S133R, N155E, G189S, F191V, T233V, G239E, V265T, D271Y, G293A, S309W, and S318P point mutations, with mutant residue numbering based on SEQ ID NO: 6. The DNA sequence for OptCel5a is set forth in SEQ ID NO: 3.

Figure 22A:
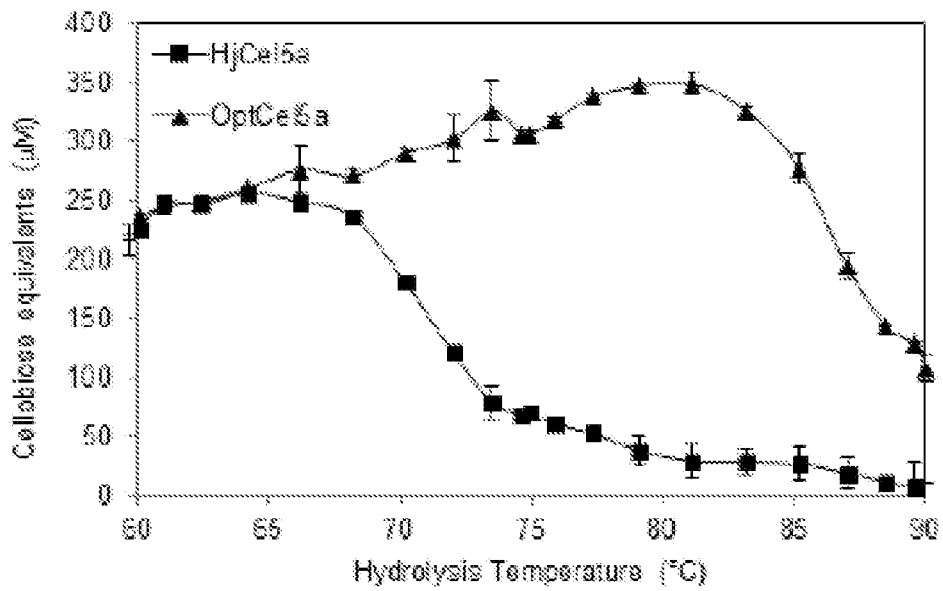
FIG. 22A is a graph showing the amount of cellulase activity versus hydrolysis temperature for WT (HjCel5a) (squares) and OptCel5a combination mutant (triangles) (with mutant residue numbering based on SEQ ID NO: 6) as described herein, according to embodiments of the present invention.

OptCel5a was transformed into the BY4742 Δkre2 strain of *Saccharomyces cerevisiae*, a glycosylation-deficient strain that secretes proteins that have similar glycosylation patterns to *H. jecorina* enzymes (Heinzelman et al. 2009, *PNAS*, 106: 5610-5615, the entire contents of which are herein incorporated by reference). When expressed and purified, OptCel5a has an optimal temperature of 81.1° C. when used to hydrolyze crystalline cellulose (Avicel) for 2 h (FIG. 22A). This makes OptCel5a more than 17° C. more thermostable than wild type HjCel5a, more than 7° C. more stable than the 110F chimera 110F (Example 4, FIG. 18A), and 6° C. more stable than s13pt4 (Example 5, FIGS. 20C, 20D).

Figure 22B:
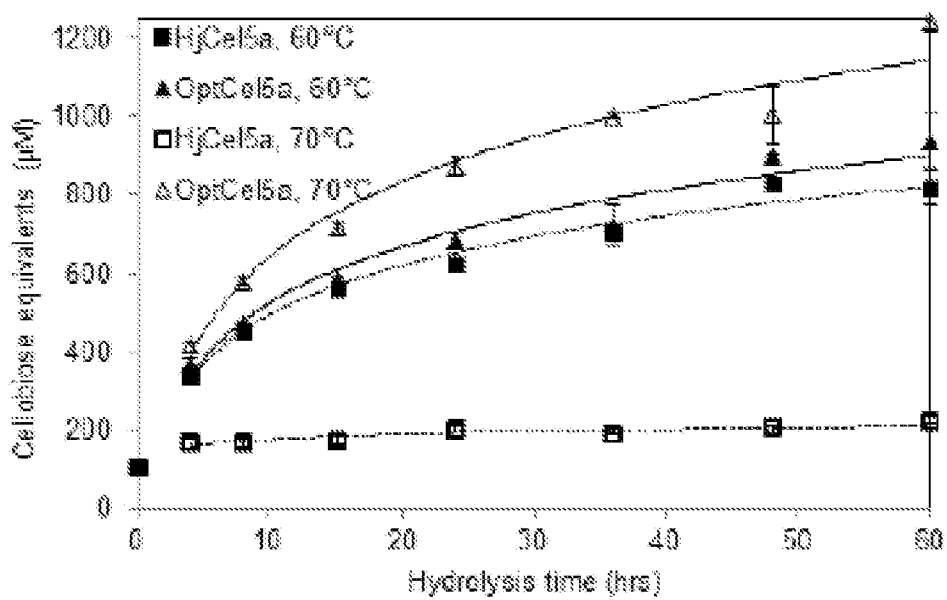
FIG. 22B is a graph showing the amount of cellulase activity over 60 hours for WT (HjCel5a)(squares) and 110F Cel5a combination mutant (triangles) (with mutant residue numbering based on SEQ ID NO: 6) at 60° C. (closed) and 70° C. (open) as indicated, according to embodiments of the present invention.

The activity of OptCel5a and wild type HjCel5a was assayed over a 60 h hydrolysis at both 60° C. and 70° C. OptCel5a had highest activity at 70° C., hydrolyzing more than 1.5 times as much cellulose as HjCel5a at its optimal temperature of 60° C. (FIG. 22B). OptCel5a is therefore compatible with the previously engineered thermostable Cel6a and Cel7a, which both operate optimally at 70° C. in 60 h hydrolysis experiments (Wu and Arnold, 2013, *Biotech. and Bioeng.*, 110:1874-1883, the entire contents of which are herein incorporated by reference).

Plasmids and Strains.

The gene encoding wild type Cel5a (including its cellulose binding module) was synthesized with *S. cerevisiae* codon optimization (DNA 2.0). Plasmids were transformed into the BY4742 Δkre2 strain of yeast (BY4742; Mat a; his3D1; leu2D0; lys2D0; ura3D0; YDR483w::kanMX4) obtained from EUROSCARF.

Enzyme Purification.

Yeast colonies expressing Cel5a with C-terminal $His_6$ tag and was grown at 30° C.: first overnight in 5 mL SD-Ura medium, expanded into 50 mL SD-Ura (+50 μg/mL kanamycin) medium for 24 h, and then expanded into 1 L YPD (+50 μg/mL kanamycin) medium for an additional 48 h. Cultures were centrifuged at 4500 g for 20 min, and the supernatant was filtered with 0.2 mm PES filter unit from Nalgene. Protein was purified using 5 mL HisTrap columns (GE Healthcare). Purified cellulases were buffered-exchanged to 50 mM sodium acetate buffer pH 5.0 using Vivaspin 20 ultrafiltration spin tubes (GE Healthcare). Protein concentrations were determined using $A_{280}$, with extinction coefficients calculated using ProtParam on the ExPASy server (Gasteiger et al. 2005, supra).

Thermostability Measurements. 100 μL samples in 50 mM sodium acetate buffer, pH 5.0 containing 0.2 μM Cel5a and 1% (w/v) Avicel were incubated at a range of temperatures for 2 h in an Eppendorf Mastercycler. A modified Park-Johnson reducing sugar assay was used to measure activity (Park and Johnson, 1949, *JBC*, 181:149-151, the entire contents of which are herein incorporated by reference). Briefly, reaction mixtures were spun at 1000 g for 5 min to remove Avicel. 50 μL of supernatant was removed and transferred to a mixture of 100 μL ferricyanide reagent (0.5 g/L $K_3Fe(CN)_6$, 34.84 g/L $K_2HPO_4$, pH 10.6) and 50 μL carbonate-cyanide reagent (5.3 g/L $Na_2CO_3$, 0.65 g/L KCN). The reaction was heated at 95° C. for 15 min in an Eppendorf Mastercycler, and then cooled on ice for 5 min. 180 μL of the reaction was removed and mixed with 90 μL ferric iron solution (2.5 g/L $FeCl_3$, 10 g/L polyvinyl pyrrolidone, 2 N $H_2SO_4$). After 2 min, absorbance at 595 nm was taken, using solutions of 0 μM to 300 μM cellobiose as standards.

Cellulase Activity Measurements.

All cellulase activity measurements were conducted in 50 mM sodium acetate buffer, pH 5.0. Constant temperature was maintained using an Eppendorf Mastercycler. To determine activity-temperature profiles of Cel5a, samples containing 0.2 μM of purified Cel5a and 1% (w/v) Avicel were incubated at 60 and 70° C. for 60 h. After hydrolysis, reaction supernatants were sampled for reducing sugar concentrations via a modified Nelson-Somogyi assay (Green et al. 1989, *Anal. Biochem.*, 182: 197-199, the entire contents of which are herein incorporated by reference). Briefly, 50 μL of reaction solution was added to 40 μL carbonate-tartrate solution (144 g/L $Na_2SO_4$, 12 g/L potassium tartrate tetrahydrate, 24 g/L $Na_2CO_3$, 16 g/L $NaHCO_3$) and 10 μL copper solution (180 g/L $Na_2SO_4$, 20 g/L $CuSO_4.5H_2O$) and heated to 95° C. for 15 min in an Eppendorf Mastercycler. The reaction was placed on ice for 5 min and then mixed with 50 μL arsenomolybdate solution (50 g/L $(NH_4)_2MoO_4$, 1.5 N $H_2SO_4$, 6 g/L $NaH_2AsO_4$). After mixing, absorbance at 520 nm was read, using 0 to 2 mM cellobiose solutions as standards.

Cellulose hydrolysis to determine the activity of optimized engineered and wild type cellulase mixtures was carried out on 1%, 3%, and 5% Avicel at 60° C. and 70° C. Samples were taken at 0 h, 4 h, 8 h, 15 h, 24 h, 36 h, 48 h, and 60 h, and reducing sugar concentration was quantified as described above.

Data Analysis.

Cellulase activity and thermostability data were plotted using Microsoft Excel. Synergy plots were made in Matlab (The Mathworks, Inc.), using the Ternplot package developed by Carl Sandrock.

Example 7

Synergy of Cel5a, Cel6a, and Cel7a Engineered Cellulases

To approximate and improve cellulase activity for industrial use, the cellobiohydrolases Cel6a and Cel7a and endoglucanase Cel5a mixtures of the wild type enzymes were compared with engineered-thermostable cellulase mixtures. The engineered-thermostable mixture includes OptCel5a (Example 6) (SEQ ID NO: 3) as the Cel5a variant, 3C6P (SEQ ID NO: 4) as the Cel6a variant (Wu and Arnold, 2013, supra), and TS8 (SEQ ID NO: 5) as the Cel7a variant (Komor et al. 2012, supra). Each of these enzymes has an optimal activity at or greater than 70° C. when measured over 60 hours (h) on Avicel. The wild type mixture, Cel5a from *H. jecorina*, Cel6a from *Humicola insolens*, and Cel7a from *Talaromyces emersonii* are the most thermostable reported homologues of each enzyme. In some embodiments, variant Cel5a, Cel6a, and Cel7a homologues from other organisms may be used. As previously reported, the wild type cellulase mixture exhibits optimal activity at 60° C. over 60 h (Wu and Arnold, 2013, supra).

Figure 23A:
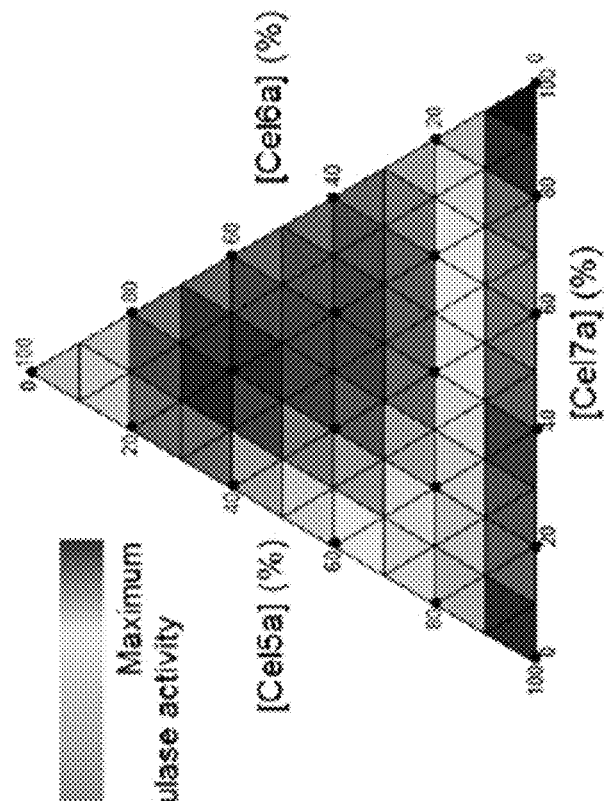
FIG. 23A is a synergy diagram for cellulase activity showing the contributions of WT Cel5a, Cel6a, and Cel7a when used as a mixture, as described herein, where each vertex represents 100% concentration of an individual cellulase, each edge represents a mixture of two cellulases and each edge indicates the concentration of the labeled cellulase ranging from 0% to 100% of the total mixture, and the interior of the triangle is a mixture of all three cellulases, with red representing maximum activity and blue representing minimum activity, according to embodiments of the present invention.
Figure 23B:
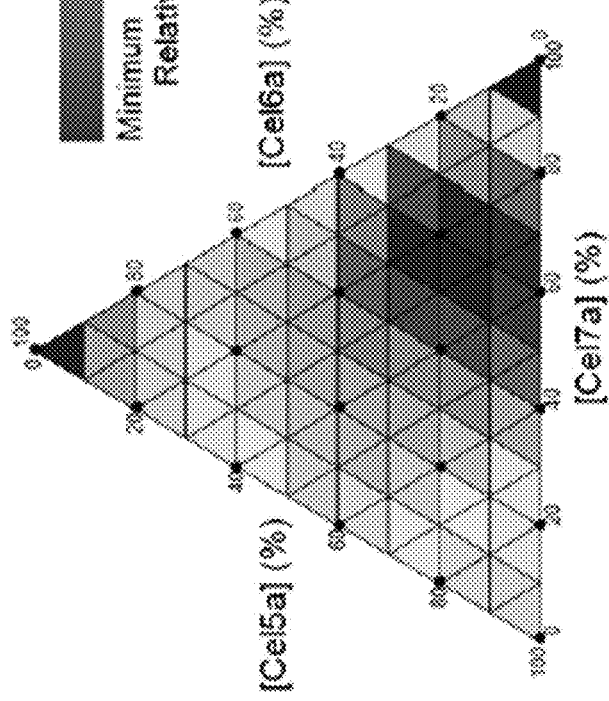
FIG. 23B is a synergy diagram for cellulase activity showing the contributions of OptCel5a, a variant Cel6a, and a variant Cel7a when used as a mixture, as described herein, where each vertex represents 100% concentration of an individual cellulase and each edge represents a mixture of two cellulases and indicates the concentration of the labeled cellulase ranging from 0% to 100% of the total mixture, and the interior of the triangle is a mixture of all three cellulases, with red representing maximum activity and blue representing minimum activity, according to embodiments of the present invention.

In these experiments, the total cellulase concentration remained fixed at 0.5 μM while the relative concentrations of each cellulase varied in steps of 0.1 μM. The resulting data were used to produce a ternary synergy diagram (Baker et al. 1998, *Biotechnology for Fuels and Chemicals*; Springer, pp. 395-403, the entire contents of which are herein incorporated by reference). Reactions on Avicel were conducted over 60 h at 60° C. for wild type and 70° C. for the engineered enzymes, conditions consistent with previous synergy studies (Baker et al. 1998, supra; Meyer et al. 2009, *J. of Cereal Science*, 50:337-344, the entire contents of which are herein incorporated by reference; Wu and Arnold 2013, supra) and realistic industrial conditions. As shown in FIGS. 23A, 23B, both enzyme mixtures exhibited substantial synergy, with the mixtures more active than any of the enzymes alone. The degree of synergy, obtained by dividing the activity of the mixture by the sum of the activities of the individual cellulases (Zhang and Lynd 2004, *Biotech. and Bioeng.*, 88:797-824, the entire contents of which are herein incorporated by reference), ranged from 1.0 to 1.6 for the wild type enzymes, and from 1.0 to 2.1 for the engineered enzymes.

In both wild type and engineered mixtures, the highest cellulose hydrolysis activity occurred with relatively small amounts of endoglucanase (10-20% of total mixture), a finding observed in other synergy studies (Van Dyk and Pletschke 2012, *Biotechnol. Advances*, 30: 1458-1480, the entire contents of which are herein incorporated by reference). Cellobiohydrolases processively hydrolyze along free cellulose ends, and are responsible for the bulk of hydrolysis. Endoglucanases non-processively produce free cellulose ends, increasing the effective concentration of cellobiohydrolase substrate. Less endoglucanase is required in an optimal mixture because the enzyme assists cellobiohydrolase function.

Figure 23C:
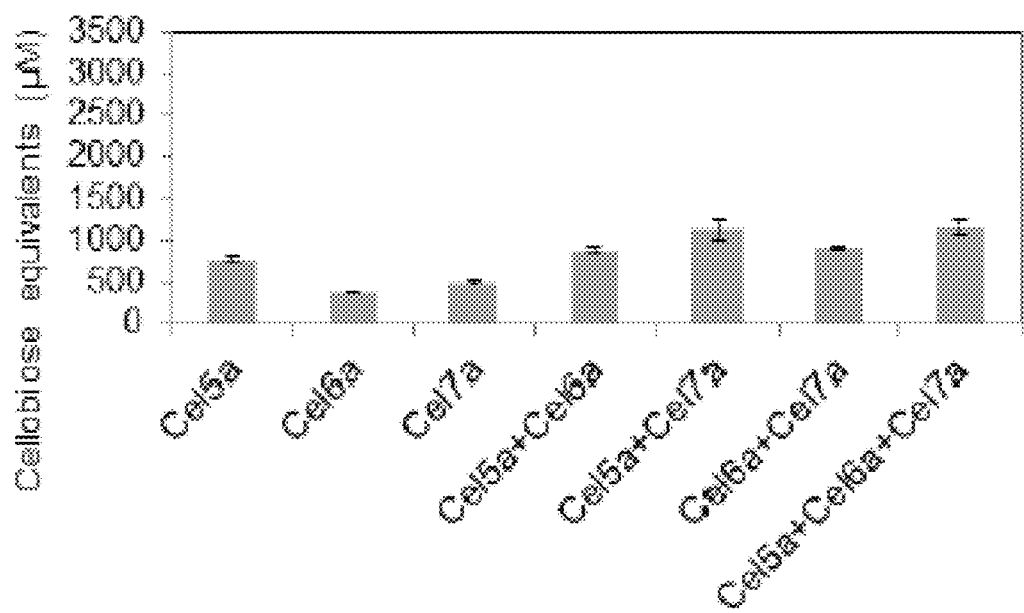
FIG. 23C is a graph showing the absolute cellulase activity for WT Cel5a, Cel6a, and Cel7a as indicated and as measured from the synergy reaction represented in FIG. 23A, according to embodiments of the present invention.
Figure 23D:
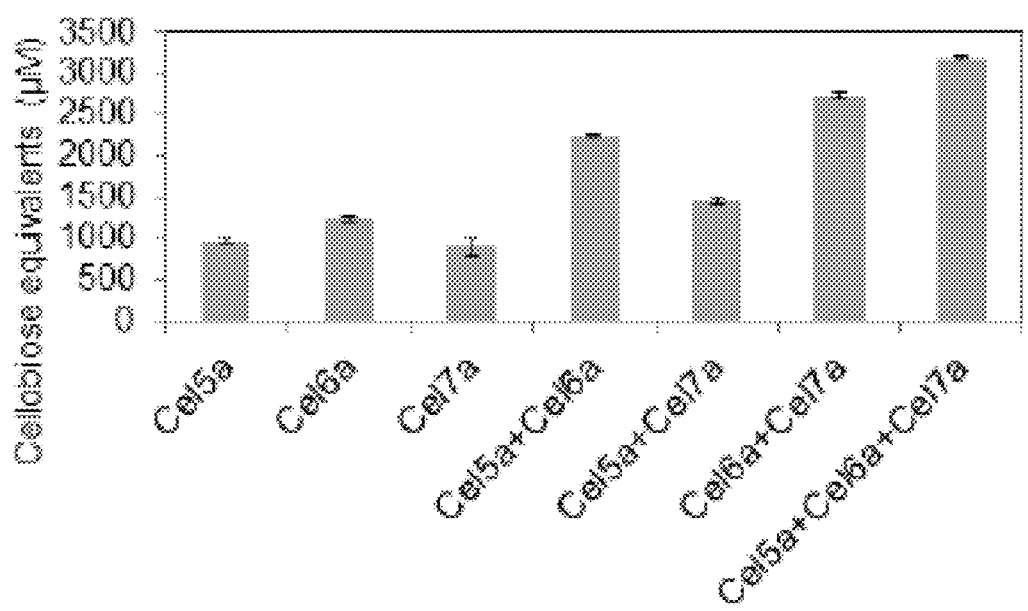
FIG. 23D is a graph showing the absolute cellulase activity for OptCel5a, a variant Cel6a, and a variant Cel7a as indicated and as measured from the synergy reaction represented in FIG. 23B, according to embodiments of the present invention.

Wild type mixtures demonstrating the highest levels of hydrolysis contained mostly Cel7a, while Cel6a was the primary component of the most effective engineered mixtures. As shown in FIGS. 23C, 23D, this change in the optimal relative enzyme loadings reflects the relative activities of Cel6a and Cel7a in the wild type and engineered cases as disclosed (Wu and Arnold 2013, supra). FIGS. 23C, 23D also show the activities of the optimal cellulase mixtures for two and three enzymes. The mixture of wild type enzymes having the most enzymatic activity in this experiment exhibited more than 1.5 fold the activity of any of its constituent enzymes, while the mixture of engineered thermostable enzymes was over 2.5 fold as active. The engineered thermostable mixture also exhibited 1.2 times the activity of a mixture containing only engineered Cel6a and Cel7a with an equal total enzyme concentration.

An Optimized Mixture of Engineered Cellulases Accelerates Cellulose Hydrolysis.

Figure 24A:
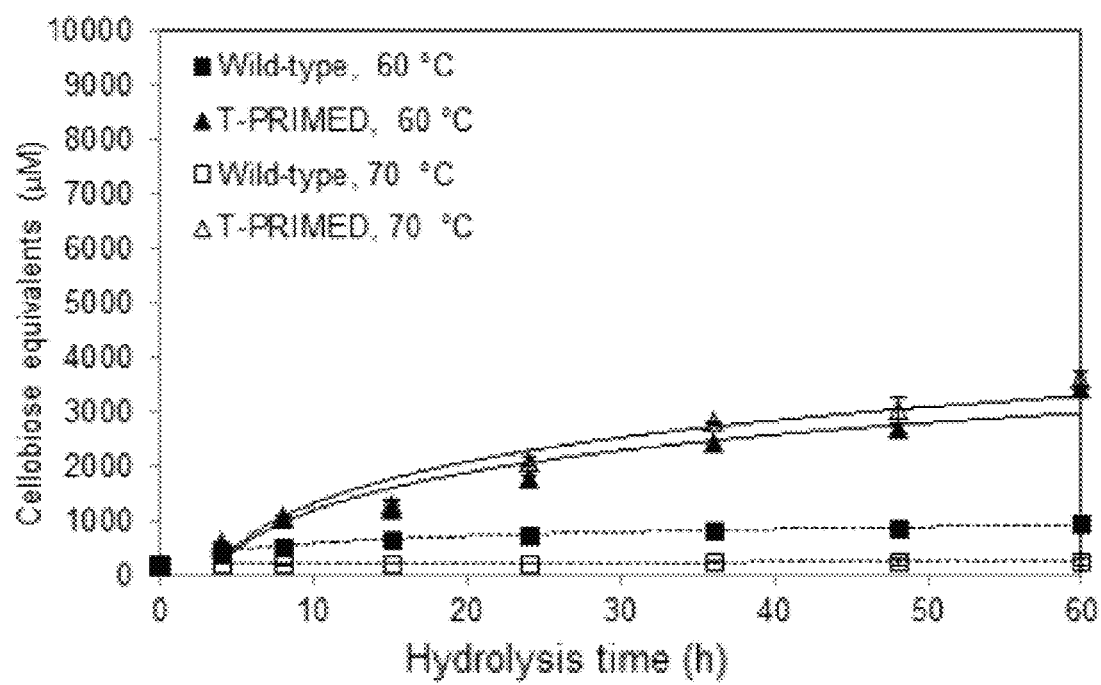
FIG. 24A is a graph showing the amount of cellulase activity over 60 hours for WT (HjCel5a)(squares) and T-PRIMED Cel5a combination mutant (triangles) (with mutant residue numbering based on SEQ ID NO: 6) at 60° C. (closed) and 70° C. (open) as indicated, on 1% w/v Avicel, according to embodiments of the present invention.
Figure 24B:
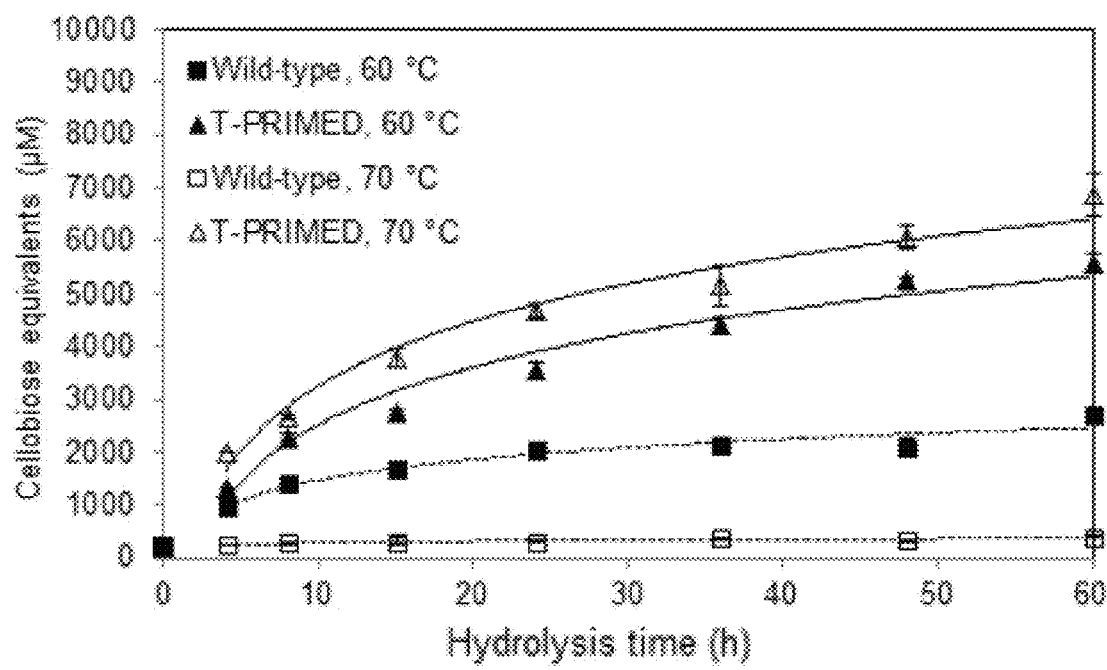
FIG. 24B is a graph showing the amount of cellulase activity over 60 hours for WT (HjCel5a)(squares) and T-PRIMED Cel5a combination mutant (triangles) (with mutant residue numbering based on SEQ ID NO: 6) at 60° C. (closed) and 70° C. (open) as indicated, on 3% w/v Avicel, according to embodiments of the present invention.
Figure 24C:
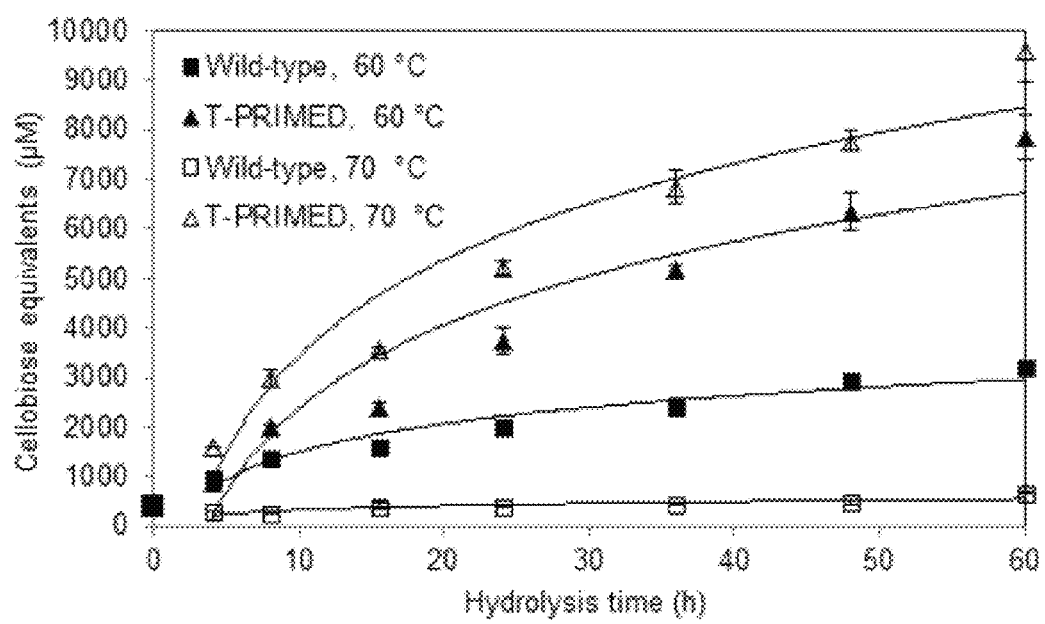
FIG. 24C is a graph showing the amount of cellulase activity over 60 hours for WT (HjCel5a)(squares) and T-PRIMED Cel5a combination mutant (triangles) (with mutant residue numbering based on SEQ ID NO: 6) at 60° C. (closed) and 70° C. (open) as indicated, on 5% w/v Avicel, according to embodiments of the present invention.
Figure 24D:
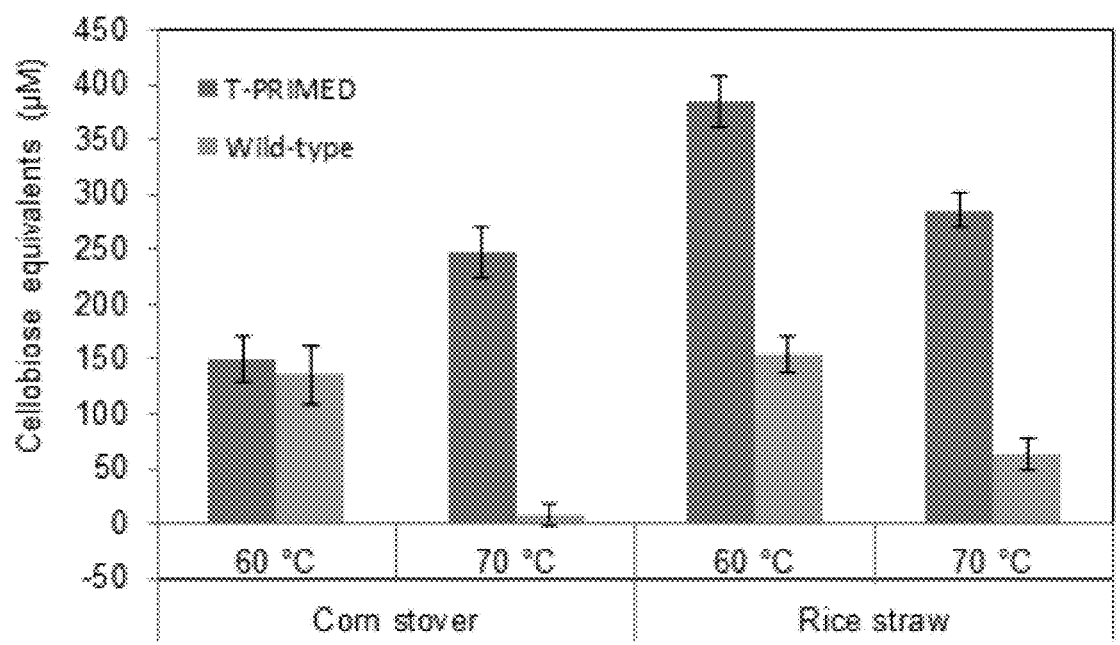
FIG. 24D is a graph showing the amount of cellulase activity for WT (light grey) and T-PRIMED Cel5a (dark grey) (with mutant residue numbering based on SEQ ID NO: 6) at 60° C. and 70° C. on both milled corn stover and dilute-acid treated rice straw as indicated, according to embodiments of the present invention.

The region of maximum activity was analyzed more closely in steps of 0.04 µM and the optimal (i.e., having the highest enzymatic activity) mixture for wild type was determined to be 0.16:0.28:0.56 (Cel5a:Cel6a:Cel7a). The optimal engineered thermostable mixture was determined to be 0.08: 0.56:0.36 (Cel5a:Cel6a:Cel7a). The engineered thermostable mixture having the most enzymatic activity was termed T-PRIMED. The activity of T-PRIMED was assayed over 60 h at both 60° C. and 70° C. and was compared to the activity of the most active wild type mixture. This assay was performed using 1%, 3%, and 5% Avicel to observe the effects of varying cellulose concentrations (FIGS. 24A, 24B, 24C). T-PRIMED exhibits the most activity at 70° C., where it is approximately three times as active as the most active mixture of wild type enzymes at 60° C. The activities of all cellulase mixtures increased at higher cellulose concentrations, with the activity ratios remaining approximately the same.

The activity of the mixtures was also tested on two industrially relevant lignocellulose substrates: milled corn stover and dilute acid-treated rice straw (FIG. 23D). T-PRIMED was more active than the wild type enzymes on both substrates, with 1.8 fold the activity of the wild type mixture on milled corn stover and 2.5 fold on treated rice straw.

Plasmids and Strains.

Genes encoding Cel6a, and Cel7a were cloned into the yeast secretion vector YEp352/PGK91-1-ass as described previously (Komor et al. 2012, supra; Wu and Arnold 2013, supra). The gene encoding wild type Cel5a (including its cellulose binding module) was synthesized with S. cerevisiae codon optimization (DNA 2.0). Sequences of all genes are in Supplementary Information. Plasmids were transformed into the BY4742 Δkre2 strain of yeast (BY4742; Mat a; his3D1; leu2D0; lys2D0; ura3D0; YDR483w::kanMX4) obtained from EUROSCARF.

Enzyme Purification.

Yeast colonies expressing Cel5a and Cel6a with C-terminal $His_6$ tags and Cel7a with an N-terminal $His_8$ tag were grown at 30° C.: first overnight in 5 mL SD-Ura medium, expanded into 50 mL SD-Ura (+50 µg/mL kanamycin) medium for 24 h, and then expanded into 1 L YPD (+50 µg/mL kanamycin) medium for an additional 48 h. Cultures were centrifuged at 4500 g for 20 min, and the supernatant was filtered with 0.2 mm PES filter unit from Nalgene. Protein was purified using 5 mL HisTrap columns (GE Healthcare). Purified cellulases were buffered-exchanged to 50 mM sodium acetate buffer pH 5.0 using Vivaspin 20 ultrafiltration spin tubes (GE Healthcare). Protein concentrations were determined using $A_{280}$, with extinction coefficients calculated using ProtParam on the ExPASy server (Gasteiger et al. 2005, supra).

Thermostability Measurements.

100 µL samples in 50 mM sodium acetate buffer, pH 5.0 containing 0.2 µM Cel5a and 1% (w/v) Avicel were incubated at a range of temperatures for 2 h in an Eppendorf Mastercycler. A modified Park-Johnson reducing sugar assay was used to measure activity (Park and Johnson 1949, supra). Briefly, reaction mixtures were spun at 1000 g for 5 min to remove Avicel. 50 µL of supernatant was removed and transferred to a mixture of 100 µL ferricyanide reagent (0.5 g/L $K_3Fe(CN)_6$, 34.84 g/L $K_2HPO_4$, pH 10.6) and 50 µL carbonate-cyanide reagent (5.3 g/L $Na_2CO_3$, 0.65 g/L KCN). The reaction was heated at 95° C. for 15 min in an Eppendorf Mastercycler, and then cooled on ice for 5 min. 180 µL of the reaction was removed and mixed with 90 µL ferric iron solution (2.5 g/L $FeCl_3$, 10 g/L polyvinyl pyrrolidone, 2 N $H_2SO_4$). After 2 min, absorbance at 595 nm was taken, using solutions of 0 µM to 300 µM cellobiose as standards.

Cellulase Activity Measurements.

All cellulase activity measurements were conducted in 50 mM sodium acetate buffer, pH 5.0. Constant temperature was maintained using an Eppendorf Mastercycler. To determine activity-temperature profiles of Cel5a, samples containing 0.2 µM of purified Cel5a and 1% (w/v) Avicel were incubated at 60 and 70° C. for 60 h. To determine the activity of the Cel5a, Cel6a, and Cel7a mixtures, purified Cel5a, Cel6a, and Cel7a were combined at different ratios to a final concentration of 0.5 µM along, with 1% Avicel in 100 µL and incubated 60° C. and 70° C. for 60 h. After hydrolysis, reaction supernatants were sampled for reducing sugar concentrations via a modified Nelson-Somogyi assay (Green et al. 1989, supra). Briefly, 50 µL of reaction solution was added to 40 µL carbonate-tartrate solution (144 g/L $Na_2SO_4$, 12 g/L potassium tartrate tetrahydrate, 24 g/L $Na_2CO_3$, 16 g/L $NaHCO_3$) and 10 µL copper solution (180 g/L $Na_2SO_4$, 20 g/L $CuSO_4.5H_2O$) and heated to 95° C. for 15 min in an Eppendorf Mastercycler. The reaction was placed on ice for 5 min and then mixed with 50 µL arsenomolybdate solution (50 g/L $(NH_4)_2MoO_4$, 1.5 N $H_2SO_4$, 6 g/L $NaH_2AsO_4$). After mixing, absorbance at 520 nm was read, using 0 to 2 mM cellobiose solutions as standards.

Cellulose hydrolysis to determine the activity of optimized engineered and wild type cellulase mixtures was carried out on 1%, 3%, and 5% Avicel at 60° C. and 70° C. Samples were taken at 0 h, 4 h, 8 h, 15 h, 24 h, 36 h, 48 h, and 60 h, and reducing sugar concentration was quantified as above.

Pre-treated lignocellulose from corn stover was obtained from the National Renewable Energy Laboratory in Golden, Colo. Pre-treated lignocellulose from rice straw was prepared as described by Hsu et al. 2010, *Bioresource Technology*, 101: 4907-4913, the entire contents of which are herein incorporated by reference. Activity assays were carried out for optimized engineered and wild type cellulase mixtures on 3% substrate at 60° C. and 70° C. for 60 h. Released cellobiose at the end of 60 h was quantified as above.

Data Analysis.

Cellulase activity and thermostability data were plotted using Microsoft Excel. Synergy plots were made in Matlab (The Mathworks, Inc.), using the Ternplot package developed by C. Sandrock.

As disclosed throughout as evidenced by, for example, the cellulase activity of a variant Cel5a shown in FIGS. 22A, 22B, a variant Cel5a enzyme has improved thermostability and activity compared to wild type. Additionally, as evidenced by FIGS. 23D, 24A, 24B, 24C, and 24D, a composition including a variant Cel5a enzyme, and variant Cel6a and variant Cel7a cellobiohydrolases has improved thermostability and activity compared to wild type.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A composition, comprising:
a variant Cel5a endoglucanase having a temperature at which half of the maximal protein activity remains ($T_{50}$) higher than a $T_{50}$ of wild type Cel5a endoglucanase and having increased enzymatic activity relative to enzymatic activity of the wild type Cel5a endoglucanase, the variant Cel5a endoglucanase comprising point mutations in a wild type Cel5a amino acid sequence of SEQ ID NO: 7 selected from the group consisting of
(a) G293A and S318P/Q/E and
(b) G293A and S318P/Q/E and one or more residues selected from the group consisting of E53D, T57N, S79P, T80E, V101I, S133R, N153D, N155E, T156E, G189S, F191V, T233V, G239E, V265T, D271Y, and S309W/L, in which the amino acid residue numbering is based on the numbering of SEQ ID NO: 6; and
a cellobiohydrolase selected from the group consisting of Cel6a encoded by SEQ ID NO: 4, Cel7a encoded by SEQ ID NO: 5, and combinations thereof.

2. The composition of claim 1, wherein the variant Cel5a endoglucanase has a $T_{50}$ above 70° C.

3. The composition of claim 1, wherein the variant Cel5a endoglucanase has a $T_{50}$ of about 1° C. to about 17° C. above the $T_{50}$ of the wild type Cel5a.

4. The composition of claim 1, wherein the increase in enzymatic activity is a net activity increase in amount of digested cellulose relative to the wild type Cel5a enzymatic activity.

5. The composition of claim 4, wherein the enzymatic activity is measured using a cellobiose activity assay.

6. The composition of claim 1, wherein the variant Cel5a endoglucanase comprises a combination of point mutations in the Cel5a amino acid sequence, the combination of point mutations being selected from the group of combinations consisting of:
 E53D, T57N, S79P, T80E, V101I, S133R, N155E, G189S, G239E, D271Y, G293A, S309L, and S318P;
 E53D, T57N, S79P, T80E, V101I, S133R, N155E, G189S, G239E, D271Y, G293A, S309W, and S318P;
 E53D, T57N, S79P, T80E, V101I, S133R, N155E, G189S, G239E, D271Y, G293A, S309L, and S318E;
 E53D, T57N, S79P, T80E, V101I, S133R, N155E, G189S, G239E, D271Y, G293A, S309W, and S318E; and
 E53D, T57N, S79P, T80E, V101I, S133R, N155E, G189S, F191V, T233V, G239E, V265T, D271Y, G293A, S309W, and S318P.

7. The composition of claim 1, wherein the variant Cel5a endoglucanase further comprises a point mutation selected from the group consisting of D13E, T18P, G64A, N76P, S79P/Q/E, T80E/Q, I82L/M, V101I/L, A122E, S133R, S139P, N155E/Q, T156E, G189S/A/E/K, K219Q/A, G239E/N/D, V265T, D271 Y/F, Y278F, and S309W/F/L.

8. A method of hydrolyzing cellulose, comprising hydrolyzing the cellulose with the composition of claim 1.

9. The method of claim 8, wherein the hydrolyzing occurs at a temperature of about 60° C. to about 70° C.

10. A method of expressing a variant Cel5a endoglucanase protein having increased thermostability compared to wild type Cel5a endoglucanase, the method comprising expressing the composition of claim 1 in a host organism.

11. The method of claim 10, wherein the host organism belongs to a genus selected from the group consisting of *Saccharomyces, Pichia, Trichoderma*, and *Aspergillus*.

12. A composition comprising a variant Cel5a endoglucanase having a temperature at which half of the maximal protein activity remains ($T_{50}$) higher than a $T_{50}$ of wild type Cel5a endoglucanase, increased enzymatic activity relative to the wild type Cel5a endoglucanase, and increased protein expression in a host organism relative to the wild type Cel5a endoglucanase, the variant Cel5a endoglucanase having a combination of mutations in a wild type Cel5a amino acid sequence of SEQ ID NO: 7, in which the amino acid residue numbering is based on the numbering of SEQ ID NO: 6, the combination of mutations being selected from the group of combinations consisting of:
 E53D, T57N, S79P, T80E, V101I, S133R, N155E, G189S, G239E, D271Y, G293A, S309L, and S318P;
 E53D, T57N, S79P, T80E, V101I, S133R, N155E, G189S, G239E, D271Y, G293A, S309W, and S318P;
 E53D, T57N, S79P, T80E, V101I, S133R, N155E, G189S, G239E, D271Y, G293A, S309L, and S318E;
 E53D, T57N, S79P, T80E, V101I, S133R, N155E, G189S, G239E, D271Y, G293A, S309W, and S318E; and
 E53D, T57N, S79P, T80E, V101I, S133R, N155E, G189S, F191V, T233V, G239E, V265T, D271Y, G293A, S309W, and S318P; and
 a cellobiohydrolase selected from the group consisting of Cel6a encoded by SEQ ID NO: 4, Cel7a encoded by SEQ ID NO: 5, and combinations thereof.

* * * * *

SEQUENCE LISTING

<160> NUMBER OF SEQ ID NOS: 7

<210> SEQ ID NO 1
<211> LENGTH: 967
<212> TYPE: DNA
<213> ORGANISM: Hypocrea jecorina

<400> SEQUENCE: 1

| | | | | | |
|---|---|---|---|---|---|
| ggcgttagat | ttgccggtgt | taatattgct | ggttttgact | tcggttgcac | taccgatggc | 60 |
| acttgtgtta | cttctaaggt | ctatcctccg | cttaagaact | ttacgggttc | caacaactat | 120 |
| cctgatgata | gggcagatgc | aacattttgt | taatgaagac | ggtatgacaa | tatttcgttt | 180 |
| gcctgttgga | tggcaatatc | tggtcaacaa | taacctggga | ggtaatttag | atagtacctc | 240 |
| tatctccaaa | tatacaattg | gtccaaggtt | gtctatcctt | aggtgcatat | tgtattgtcg | 300 |
| atatacataa | ttatgctaga | tggaatggcg | gtattattgg | tcaaggcggt | ccaacaaacg | 360 |
| cgcaatttac | ttcattgtga | gcagttggct | agtaaatacg | cgtcacagtc | cagggtttgg | 420 |
| tttggaatta | tgaatgagcc | acacgatgtt | aacattaata | cctgggctgc | taccgttcaa | 480 |
| gaagttgtca | cagcaattag | aaatgtgggc | tacgtcccag | tttatcagtc | tacctggtaa | 540 |
| tgattggcaa | tctgctggtg | ctttcatttc | tgacggcagt | gccgctgcgt | tgtcgcaagt | 600 |
| aactaatcca | gatggctcca | caactaatct | aattttcgac | gtgcataagt | atttggattc | 660 |
| ggataatagt | ggtactcatg | cagagtgtac | tactaacaat | atcgatggtg | cctagcccgt | 720 |
| tggcaacctg | gttacgtcaa | aacaatagac | aagcaatatt | gacggaaacc | ggtggtggta | 780 |
| atgtacaaag | ttgtattcag | gatatgtgtc | aacaaataca | gtaccttaac | caaaactcaa | 840 |
| gtttacttag | gctacgttgg | ctggggtgct | ggttccttcg | acagtactta | cgttttgact | 900 |
| gagacaccta | catccagtgg | taatagttgg | accgatactt | ctttggtatc | ttcttgctta | 960 |
| gctagaa | | | | | | 967 |

<210> SEQ ID NO 2
<211> LENGTH: 217
<212> TYPE: DNA
<213> ORGANISM: Artificial Sequence
<220> FEATURE:
<223> OTHER INFORMATION: Added sequence to Cel5a

<400> SEQUENCE: 2

| | | | | | |
|---|---|---|---|---|---|
| ggctagacaa | caaacagtat | ggggtcaatg | tggtggtatt | ggatggtctg | gtccgacaaa | 60 |
| ctgtgctcca | ggctcggcat | gttcgacact | aaatccatat | tacgctcaat | gtatccctgg | 120 |
| cgctaccact | ataacaactt | ctactagacc | accttctggt | ccgacgacaa | ctacaagggc | 180 |
| tacctcaacc | tcttcctcta | caccccctac | ttccagc | | | 217 |

<210> SEQ ID NO 3
<211> LENGTH: 967
<212> TYPE: DNA
<213> ORGANISM: Hypocrea jecorina

<400> SEQUENCE: 3

| | | | | | |
|---|---|---|---|---|---|
| ggcgttagat | ttgccggtgt | taatattgct | ggttttgact | tcggttgcac | taccgatggc | 60 |
| acttgtgtta | cttctaaggt | ctatcctccg | cttaagaact | ttacgggatc | caacaactat | 120 |
| cctgatgata | gggcagatgc | aacattttgt | taatgatgac | ggtatgaata | tatttcgttt | 180 |
| gcctgttgga | tggcaatatc | tggtcaacaa | taacctggga | ggtaatttag | atcctgagtc | 240 |
| tatctccaaa | tatacaattg | gtccaaggtt | gtctatcctt | aggtgcatat | tgtattatcg | 300 |

| | |
|---|---|
| atatacataa ttatgctaga tggaatggcg gtattattgg tcaaggcggt ccaacaaacg | 360 |
| cgcaatttac ttcattgtga gcagttggct aggaaatacg cgtcacagtc cagggtttgg | 420 |
| tttggaatta tgaatgagcc acacgatgtt aacattgaga cctgggctgc taccgttcaa | 480 |
| gaagttgtca cagcaattag aaatgtgggc tacgtcccag tttatcagtc tacctggtaa | 540 |
| tgattggcaa tctgctagtg ctgttatttc tgacggcagt gccgctgcgt tgtcgcaagt | 600 |
| aactaatcca gatggctcca caactaatct aattttcgac gtgcataagt atttggattc | 660 |
| ggataatagt ggtactcatg cagagtgtgt tactaacaat atcgatgagg cctagcccgc | 720 |
| tagcaacctg gttacgtcaa aacaatagac aagcaatatt gacggaaacc ggtggtggta | 780 |
| atactcaaag ttgtattcag tatatgtgtc aacaaataca gtaccttaac caaaactcaa | 840 |
| gtttacttag gctacgttgg ctgggctgct ggttccttcg acagtactta cgttttgact | 900 |
| gagacaccta catggagtgg taatagttgg accgatactc ctttggtatc ttcttgctta | 960 |
| gctagaa | 967 |

<210> SEQ ID NO 4
<211> LENGTH: 1383
<212> TYPE: DNA
<213> ORGANISM: Humicola insolens

<400> SEQUENCE: 4

| | |
|---|---|
| agagggtat ctttggataa aagggctagc tgctcaagcg tctggggcca atgtggtggc | 60 |
| cagaattggt cgggtccgac ctgctgtgct tccggaagca catgcgtcta cttcaacgac | 120 |
| tattactccc agtgtcttcc cggcgctgca agctcaagct cgtccacgcg cgccgcgtcg | 180 |
| acgacttctc gagtatcccc cacaacatcc cggtcgagct ccgcgacgcc tccacctggt | 240 |
| tctactacta ccagagtacc tccagtcgga tcgggaaccg ctacgtattc aggtaacccc | 300 |
| tttgaaggtg ttcagctgtg ggctaataac tattatagat ctgaggtaca tacactggcc | 360 |
| attccgcaaa ttacagaccc cgcgttgcgt gccgcagcta gtgctgcggc tgaggtgcca | 420 |
| agttttttgt ggctggatac tttggacaaa accccttaa tggaacaaac gttggctgat | 480 |
| atacgtactg cgaataaaaa cggcggcaat tatgctggac aatttgtggt ttatgacctg | 540 |
| ccggatagag attgtgctgc actagcgagc aacggggagt acagcattgc ggatggcggt | 600 |
| gtcgcaaagt acaaaaacta tatagatact atcaggcaaa tagttgtcga atacagtgat | 660 |
| attcgtacgc tgcttgtaat cgaacccgat tccttagcga acttggtgac aaatctaggt | 720 |
| actccgaagt gtgcgaacgc gcagagtgct tatcttgagt gcatcaatta tgcagtcacc | 780 |
| cagttgaatt tgccaaacgt tgcaatgtat cttgatgctg gtcatgccgg tggttgggt | 840 |
| tggccagcaa atctggatcc cgctgcgcag ctgtttgcaa atgtttacaa aaatgcctca | 900 |
| agtcctagag cgctgagggg tcttgcaaca atgttgcta attacaacgc ttggtcaata | 960 |
| gcgagtcccc caccgtacac aagccctaac ccaaactacg atgagaagca ttacatagaa | 1020 |
| gcatttgctc ctttgcttcg taaccaaggt tttgatgcaa agtttatcgt cgataccgga | 1080 |
| agaaacggca agcagccgac agggcagcta gaatggggc actggtgcaa tgtcaagggt | 1140 |
| acgggtttcg gtgttagacc cacggctaac actgggcatg agttggttga tgcattcgtt | 1200 |
| tgggtaaaac ccggaggaga gtcagatgga acgagtgatc cttctgctcc aaggttcgat | 1260 |
| cctcattgcg cattaccaga tgcttttcag ccagcacctc aagcaggagc ttggttccaa | 1320 |
| gcttattttg tacaattact gactaacgcc aatcctagtt ttctacatca ccatcaccac | 1380 | cat 1383

<210> SEQ ID NO 5
<211> LENGTH: 1536
<212> TYPE: DNA
<213> ORGANISM: Talaromyces emersonii

<400> SEQUENCE: 5

```
gctagccatc accatcacca ccatcaccat cagcaggctt gctccctcac cgctgagaac    60
caccctcctc tcacctggaa gcgctgcacc tctggcggca gctgctcgac cgtgaacggc   120
gccgtcgttc ttgatgcgaa ctggcgttgg gtgcacgatg tgaacggata caccaactgc   180
tacacgggca ataccgggga ccccacgctt tgccctgacg acgaaacctg cgcccagaac   240
tgttgcctgg acggcgcgga ctactcttcg acctatggta tcaccaccag cggtgactcc   300
ctgaagctca agttcgtcac caagcaccag tacggcacca acgtcggctc ccgtgtctat   360
ctgctgcagg acgactcgac ctatcagatc ttcaagcttc tgaaccgcga gttcagcttt   420
gacgtcgatg tctccaatct tccgtgcgga ttgaacggcg ctctgtactt tgtcgccatg   480
gacgccgacg gcggcgtgtc caagtaccct ggcaacaagg caggcgctaa gtatggcact   540
ggttactgcg actctcagtg ccctcggat ctcaagttca tcaacggtca ggccaatgtt   600
gaaggctggc agccgtctgc caacgaccca aatgccggcg ttggtgacca cggctcctgc   660
tgtgcggaga tggatgtctg ggaagcaaac agcatctcca atgcggtcac tccgcacccg   720
tgcgacacgc caggccagac gatgtgctct ggagatgact gcggtggcac atactctaac   780
gatcgctacg cgggaacctg cgatcctgac ggctgtgact tcaacccctta ccgcatgggc   840
aacacttctt tctacgggcc tggcaagatc atcgatacca ccaagccctt cactgtcgtg   900
acgcagttcc tcactgatga tggtacggat actggaactc tcagcgagat caagcgcttc   960
tacgtgcaga acggcaaggt catccccaac cctgagtcca agatcgccgg cgtctccggc  1020
aactcgatca cgacggagtt ctgcactgct cagaagcagg cctttggcga cacggacgtc  1080
ttctctcagc acggtggcct ggccaagatg ggagcggcca tgcagcaggg tatggtcctg  1140
gtgatgagcc tgtgggacga tcactatgcc aacatgctct ggctggacag catctacccg  1200
actgatgcgg acccggacac ccctggcgtc gcgcgcggta cttgccccac gacctccggc  1260
gtcccggccg acgttgagtc gcagtacccc aattcatatg ttatcttctc caacatcaag  1320
gtcggaccca tcaactcgac cttcaccgcc aaccctcccg gcggaaaccc gcctggcacc  1380
accaccaccc gccgcccagc cactaccact ggaagctctc ccggacctac ccagtctcac  1440
tacggccagt gcggcggtat tggctacagc ggccccacgg tctgcgccag cggcacaact  1500
tgccaggtcc tgaacccctta ctactctcag tgcctg                           1536
```

<210> SEQ ID NO 6
<211> LENGTH: 339
<212> TYPE: PRT
<213> ORGANISM: Hypocrea jecorina

<400> SEQUENCE: 6

```
Gly Val Arg Phe Ala Gly Val Asn Ile Ala Gly Phe Asp Phe Gly Cys
1               5                   10                  15

Thr Thr Asp Gly Thr Cys Val Thr Ser Lys Val Tyr Pro Pro Leu Lys
                20                  25                  30

Asn Phe Thr Gly Ser Asn Asn Tyr Pro Asp Gly Ile Gly Gln Met Gln
            35                  40                  45
```

-continued

His Phe Val Asn Glu Asp Gly Met Thr Ile Phe Arg Leu Pro Val Gly
 50                  55                  60

Trp Gln Tyr Leu Val Asn Asn Leu Gly Gly Asn Leu Asp Ser Thr
 65                  70                  75                  80

Ser Ile Ser Lys Tyr Asp Gln Leu Val Gln Gly Cys Leu Ser Leu Gly
                 85                  90                  95

Ala Tyr Cys Ile Val Asp Ile His Asn Tyr Ala Arg Trp Asn Gly Gly
            100                 105                 110

Ile Ile Gly Gln Gly Gly Pro Thr Asn Ala Gln Phe Thr Ser Leu Trp
            115                 120                 125

Ser Gln Leu Ala Ser Lys Tyr Ala Ser Gln Ser Arg Val Trp Phe Gly
130                 135                 140

Ile Met Asn Glu Pro His Asp Val Asn Ile Asn Thr Trp Ala Ala Thr
145                 150                 155                 160

Val Gln Glu Val Val Thr Ala Ile Arg Asn Ala Gly Ala Thr Ser Gln
                165                 170                 175

Phe Ile Ser Leu Pro Gly Asn Asp Trp Gln Ser Ala Gly Ala Phe Ile
            180                 185                 190

Ser Asp Gly Ser Ala Ala Ala Leu Ser Gln Val Thr Asn Pro Asp Gly
            195                 200                 205

Ser Thr Thr Asn Leu Ile Phe Asp Val His Lys Tyr Leu Asp Ser Asp
210                 215                 220

Asn Ser Gly Thr His Ala Glu Cys Thr Thr Asn Asn Ile Asp Gly Ala
225                 230                 235                 240

Phe Ser Pro Leu Ala Thr Trp Leu Arg Gln Asn Asn Arg Gln Ala Ile
                245                 250                 255

Leu Thr Glu Thr Gly Gly Gly Asn Val Gln Ser Cys Ile Gln Asp Met
            260                 265                 270

Cys Gln Gln Ile Gln Tyr Leu Asn Gln Asn Ser Asp Val Tyr Leu Gly
            275                 280                 285

Tyr Val Gly Trp Gly Ala Gly Ser Phe Asp Ser Thr Tyr Val Leu Thr
            290                 295                 300

Glu Thr Pro Thr Ser Ser Gly Asn Ser Trp Thr Asp Thr Ser Leu Val
305                 310                 315                 320

Ser Ser Cys Leu Ala Arg Lys Gly Gly Ser Gly Ser Gly His His His
                325                 330                 335

His His His

<210> SEQ ID NO 7
<211> LENGTH: 418
<212> TYPE: PRT
<213> ORGANISM: Hypocrea jecorina

<400> SEQUENCE: 7

Met Asn Lys Ser Val Ala Pro Leu Leu Leu Ala Ala Ser Ile Leu Tyr
 1               5                  10                  15

Gly Gly Ala Ala Ala Gln Gln Thr Val Trp Gly Gln Cys Gly Gly Ile
                 20                  25                  30

Gly Trp Ser Gly Pro Thr Asn Cys Ala Pro Gly Ser Ala Cys Ser Thr
             35                  40                  45

Leu Asn Pro Tyr Tyr Ala Gln Cys Ile Pro Gly Ala Thr Thr Ile Thr
         50                  55                  60

Thr Ser Thr Arg Pro Pro Ser Gly Pro Thr Thr Thr Arg Ala Thr
 65                  70                  75                  80

```
Ser Thr Ser Ser Ser Thr Pro Pro Thr Ser Ser Gly Val Arg Phe Ala
                85              90              95

Gly Val Asn Ile Ala Gly Phe Asp Phe Gly Cys Thr Thr Asp Gly Thr
            100             105             110

Cys Val Thr Ser Lys Val Tyr Pro Pro Leu Lys Asn Phe Thr Gly Ser
            115             120             125

Asn Asn Tyr Pro Asp Gly Ile Gly Gln Met Gln His Phe Val Asn Asp
        130             135             140

Asp Gly Met Thr Ile Phe Arg Leu Pro Val Gly Trp Gln Tyr Leu Val
145             150             155             160

Asn Asn Asn Leu Gly Gly Asn Leu Asp Ser Thr Ser Ile Ser Lys Tyr
                165             170             175

Asp Gln Leu Val Gln Gly Cys Leu Ser Leu Gly Ala Tyr Cys Ile Val
            180             185             190

Asp Ile His Asn Tyr Ala Arg Trp Asn Gly Gly Ile Ile Gly Gln Gly
        195             200             205

Gly Pro Thr Asn Ala Gln Phe Thr Ser Leu Trp Ser Gln Leu Ala Ser
    210             215             220

Lys Tyr Ala Ser Gln Ser Arg Val Trp Phe Gly Ile Met Asn Glu Pro
225             230             235             240

His Asp Val Asn Ile Asn Thr Trp Ala Ala Thr Val Gln Glu Val Val
                245             250             255

Thr Ala Ile Arg Asn Ala Gly Ala Thr Ser Gln Phe Ile Ser Leu Pro
            260             265             270

Gly Asn Asp Trp Gln Ser Ala Gly Ala Phe Ile Ser Asp Gly Ser Ala
            275             280             285

Ala Ala Leu Ser Gln Val Thr Asn Pro Asp Gly Ser Thr Thr Asn Leu
    290             295             300

Ile Phe Asp Val His Lys Tyr Leu Asp Ser Asp Asn Ser Gly Thr His
305             310             315             320

Ala Glu Cys Thr Thr Asn Asn Ile Asp Gly Ala Phe Ser Pro Leu Ala
            325             330             335

Thr Trp Leu Arg Gln Asn Asn Arg Gln Ala Ile Leu Thr Glu Thr Gly
            340             345             350

Gly Gly Asn Val Gln Ser Cys Ile Gln Asp Met Cys Gln Gln Ile Gln
            355             360             365

Tyr Leu Asn Gln Asn Ser Asp Val Tyr Leu Gly Tyr Val Gly Trp Gly
        370             375             380

Ala Gly Ser Phe Asp Ser Thr Tyr Val Leu Thr Glu Thr Pro Thr Gly
385             390             395             400

Ser Gly Asn Ser Trp Thr Asp Thr Ser Leu Val Ser Ser Cys Leu Ala
                405             410             415

Arg Lys
```